United States Patent
Lombardi et al.

(10) Patent No.: US 12,178,420 B1
(45) Date of Patent: Dec. 31, 2024

(54) SYSTEMS AND METHODS FOR DELIVERING IMPLANTABLE OCCLUDER DEVICES FOR TREATING ATRIAL SEPTAL DEFECTS

(71) Applicant: atHeart Medical AG, Baar (CH)

(72) Inventors: Fabien Lombardi, Lucerne (CH); Andreas Mellmann, Sigmaringen (DE); Stefano Buzzi, Birmensdorf (CH); Stefan Marty, Ebikon (CH)

(73) Assignee: atHeart Medical AG, Baar (CH)

( * ) Notice: Subject to any disclaimer, the term of this patent is extended or adjusted under 35 U.S.C. 154(b) by 0 days.

(21) Appl. No.: 18/614,537

(22) Filed: Mar. 22, 2024

Related U.S. Application Data

(60) Provisional application No. 63/563,834, filed on Mar. 11, 2024, provisional application No. 63/591,727, filed on Oct. 19, 2023.

(51) Int. Cl.
*A61B 17/00* (2006.01)

(52) U.S. Cl.
CPC .............. *A61B 17/0057* (2013.01); *A61B 2017/00004* (2013.01); *A61B 2017/00367* (2013.01); *A61B 2017/00606* (2013.01); *A61B 2017/00623* (2013.01); *A61B 2017/00867* (2013.01); *A61B 2017/00893* (2013.01)

(58) Field of Classification Search
CPC ........... A61B 2017/00004; A61B 2017/00367; A61B 2017/00606; A61B 2017/00623; A61B 2017/00867
See application file for complete search history.

(56) References Cited

U.S. PATENT DOCUMENTS

| | | | |
|---|---|---|---|
| 3,773,034 A | 11/1973 | Burns et al. | |
| 4,834,069 A | 5/1989 | Umeda | |
| 4,998,923 A | 3/1991 | Samson et al. | |
| 5,325,845 A | 7/1994 | Adair | |
| 5,462,527 A | 10/1995 | Stevens-Wright et al. | |
| 5,690,644 A | 11/1997 | Yurek et al. | |

(Continued)

FOREIGN PATENT DOCUMENTS

| | | |
|---|---|---|
| EP | 1052944 B1 | 9/2007 |
| EP | 2019633 B1 | 8/2012 |

(Continued)

*Primary Examiner* — Alexander J Orkin
(74) *Attorney, Agent, or Firm* — Greenberg Traurig, LLP; Christopher C. Bolten; Albert K. Heng

(57) ABSTRACT

Systems and methods for delivering an implantable occluder device, e.g., an atrial septal defect occluder having a bioresorbable frame, to the atrial septum of a patient are provided. The system may include an outer shaft configured to be removably coupled to a proximal end of the occluder, an inner shaft slidably disposed within the outer shaft and configured to be removably coupled to a distal end of the occluder, and an outer sheath slidably disposed over the outer shaft and having an expandable distal region configured to transition between a collapsed delivery configuration defining an atraumatic tip, and an expanded configuration to facilitate passage of the occluder therethrough. The system may include a handle having slidable and rotatable actuators operatively coupled to the outer shaft, inner shaft, and outer sheath for deploying and releasing the occluder at the atrial septum.

30 Claims, 41 Drawing Sheets

(56) References Cited

U.S. PATENT DOCUMENTS

| | | |
|---|---|---|
| 5,772,578 A | 6/1998 | Heimberger et al. |
| 5,853,422 A | 12/1998 | Huebsch et al. |
| 5,944,738 A | 8/1999 | Amplatz et al. |
| 6,012,494 A | 1/2000 | Balazs |
| 6,024,756 A | 2/2000 | Huebsch et al. |
| 6,059,813 A | 5/2000 | Vrba et al. |
| 6,488,706 B1 | 12/2002 | Solymar |
| 6,585,718 B2 | 7/2003 | Hayzelden et al. |
| 6,749,560 B1 | 6/2004 | Konstorum et al. |
| D493,223 S | 7/2004 | Solymar |
| 6,780,151 B2 | 8/2004 | Grabover et al. |
| 6,949,116 B2 | 9/2005 | Solymar et al. |
| 7,087,072 B2 | 8/2006 | Marino et al. |
| 7,147,656 B2 | 12/2006 | Andreas et al. |
| 7,338,514 B2 | 3/2008 | Wahr et al. |
| 7,582,104 B2 | 9/2009 | Corcoran et al. |
| 7,658,748 B2 | 2/2010 | Marino et al. |
| 7,678,123 B2 | 3/2010 | Chanduszko |
| 7,682,319 B2 | 3/2010 | Martin et al. |
| 7,691,115 B2 | 4/2010 | Corcoran et al. |
| 7,691,128 B2 | 4/2010 | Blaeser et al. |
| 7,717,937 B2 | 5/2010 | Wahr et al. |
| 7,794,487 B2 | 9/2010 | Majercak et al. |
| 7,871,419 B2 | 1/2011 | Devellian et al. |
| 7,927,351 B2 | 4/2011 | Corcoran et al. |
| 8,162,974 B2 | 4/2012 | Eskuri et al. |
| 8,257,389 B2 | 9/2012 | Chanduszko et al. |
| 8,277,480 B2 | 10/2012 | Callaghan et al. |
| 8,372,112 B2 | 2/2013 | Christianson et al. |
| 8,480,706 B2 | 7/2013 | Chanduszko et al. |
| 8,551,135 B2 | 10/2013 | Kladakis et al. |
| 8,636,765 B2 | 1/2014 | Callaghan et al. |
| 8,721,714 B2 | 5/2014 | Kelley |
| 8,764,848 B2 | 7/2014 | Callaghan et al. |
| 8,932,311 B2 | 1/2015 | Melzer et al. |
| 9,005,242 B2 | 4/2015 | Cahill |
| 9,017,373 B2 | 4/2015 | Chanduszko et al. |
| 9,017,377 B2 | 4/2015 | Steiner et al. |
| 9,149,263 B2 | 10/2015 | Chanduszko |
| 9,381,006 B2 | 7/2016 | Masters |
| 9,636,095 B2 | 5/2017 | Stoop et al. |
| 9,649,097 B2 | 5/2017 | Weishaupt et al. |
| 9,861,346 B2 | 1/2018 | Callaghan |
| 9,949,728 B2 | 4/2018 | Cahill |
| 10,219,795 B2 | 3/2019 | Widmer et al. |
| 10,251,740 B2 | 4/2019 | Eigler et al. |
| 10,485,525 B2 | 11/2019 | Cahill |
| 10,820,907 B2 | 11/2020 | Mellmann et al. |
| 11,229,539 B2 | 1/2022 | Cully et al. |
| 11,540,933 B2 | 1/2023 | Honeyfield et al. |
| 11,622,674 B2 | 4/2023 | Jensen |
| 2002/0165461 A1 | 11/2002 | Hayzelden et al. |
| 2004/0181237 A1* | 9/2004 | Forde ............... A61B 17/12122 623/1.11 |
| 2006/0106415 A1 | 5/2006 | Gabbay |
| 2006/0122647 A1* | 6/2006 | Callaghan .......... A61B 17/0057 606/213 |
| 2006/0135961 A1 | 6/2006 | Rosenman et al. |
| 2007/0088382 A1 | 4/2007 | Bei et al. |
| 2007/0293890 A1 | 12/2007 | Corcoran et al. |
| 2008/0015633 A1* | 1/2008 | Abbott ............... A61B 17/0644 606/207 |
| 2008/0077180 A1 | 3/2008 | Kladakis et al. |
| 2008/0154303 A1* | 6/2008 | Yassinzadeh ...... A61B 17/0057 606/213 |
| 2008/0249558 A1* | 10/2008 | Cahill ................ A61B 17/3439 606/1 |
| 2009/0248141 A1 | 10/2009 | Shandas et al. |
| 2011/0082495 A1 | 4/2011 | Ruiz |
| 2015/0005810 A1 | 1/2015 | Center et al. |
| 2015/0105819 A1* | 4/2015 | Becking ............... A61B 17/221 606/200 |
| 2015/0359547 A1* | 12/2015 | Vale .................. A61M 25/0082 606/115 |
| 2017/0043066 A1 | 2/2017 | Laub |
| 2017/0143318 A1 | 5/2017 | Hu |
| 2017/0258475 A1* | 9/2017 | Mellmann ........ A61B 17/12145 |
| 2017/0281344 A1 | 10/2017 | Costello |
| 2020/0222034 A1* | 7/2020 | Liu .................... A61B 17/0057 |
| 2021/0022859 A1 | 1/2021 | Crosbie et al. |
| 2023/0008013 A1 | 1/2023 | Wang et al. |
| 2023/0116901 A1 | 4/2023 | Conlon |
| 2023/0137418 A1 | 5/2023 | Kelly et al. |

FOREIGN PATENT DOCUMENTS

| | | |
|---|---|---|
| EP | 1651116 B1 | 6/2013 |
| EP | 1572003 B1 | 3/2017 |
| WO | WO-2005092203 A1 | 10/2005 |
| WO | WO-2005110240 A1 | 11/2005 |

* cited by examiner

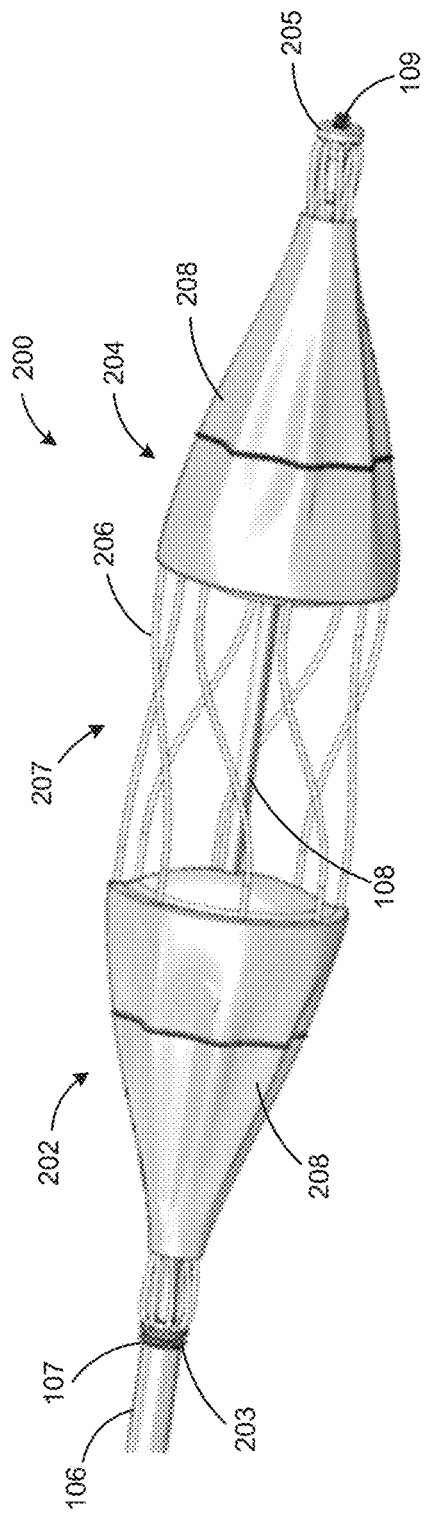
FIG. 2A
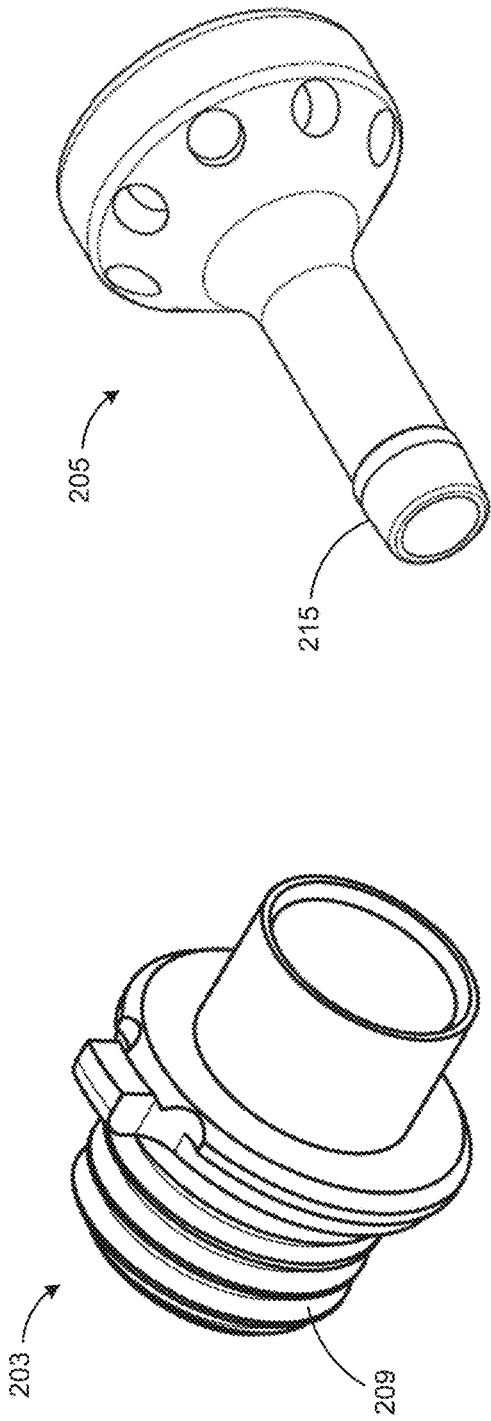
FIG. 2B
FIG. 2C

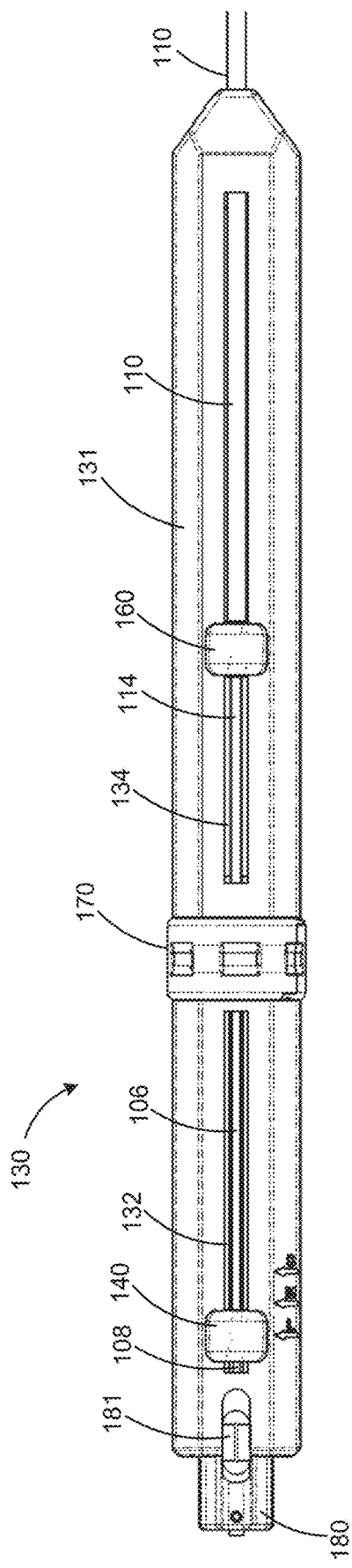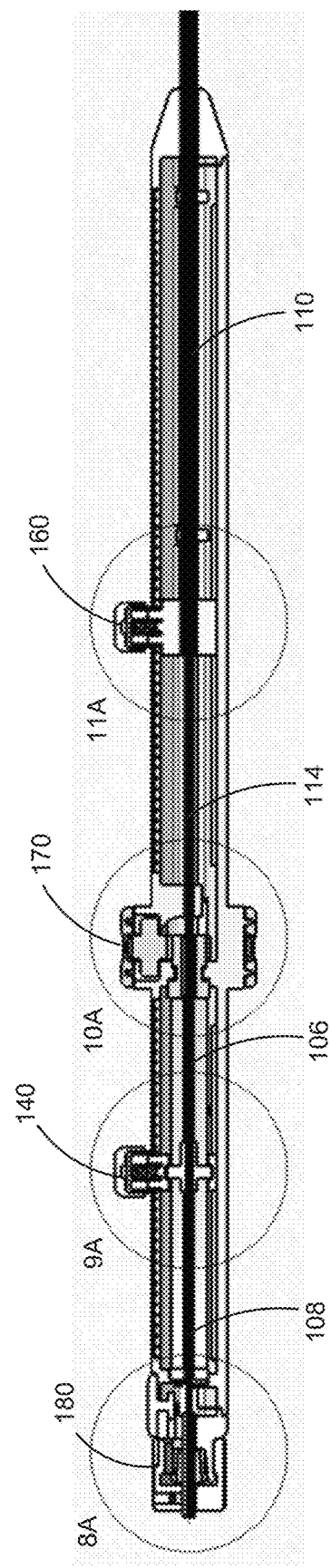
FIG. 7A
FIG. 7B

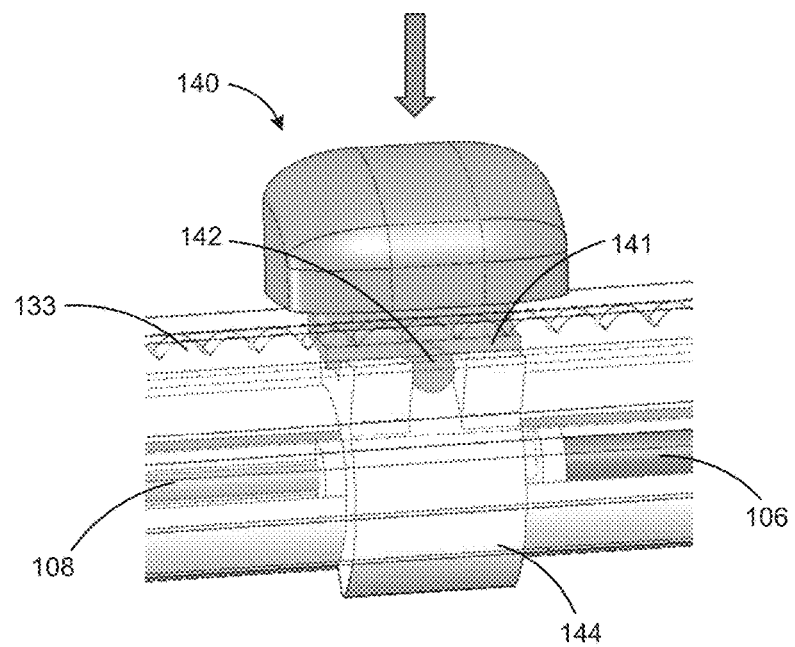
FIG. 9D
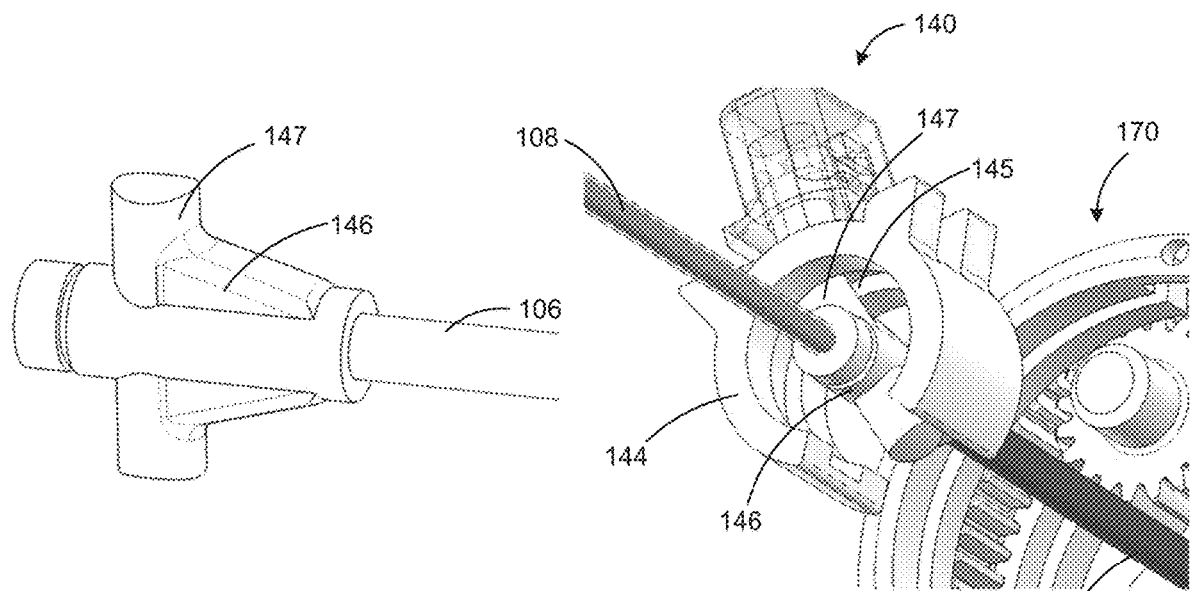
FIG. 9E
FIG. 9F

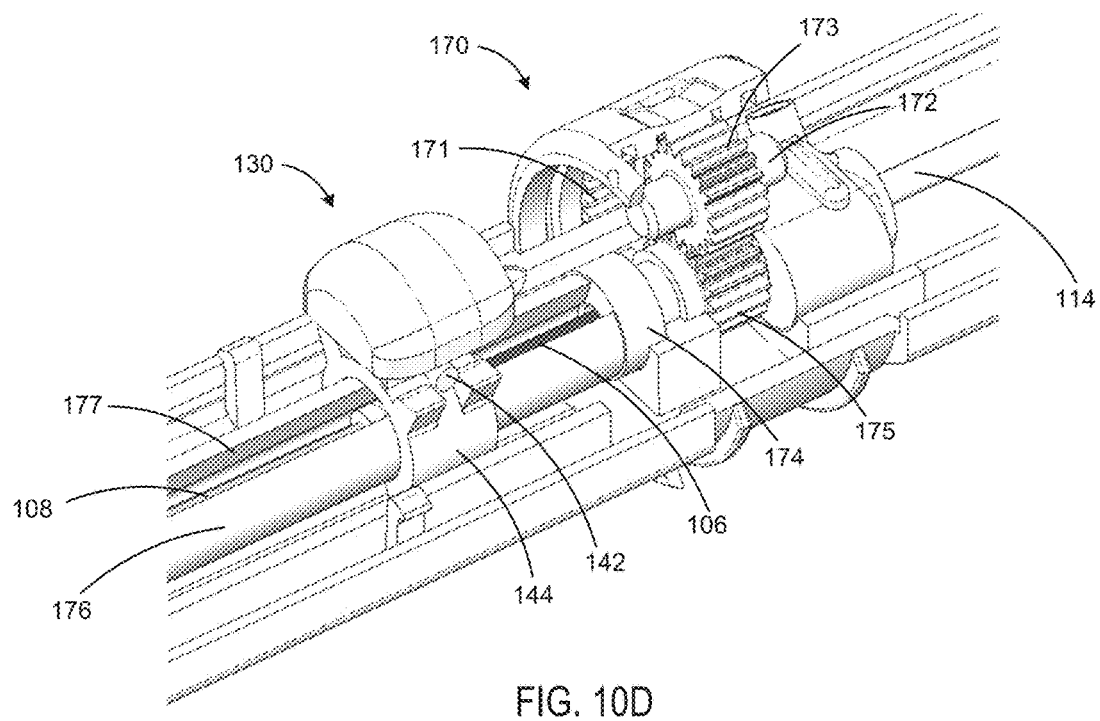
FIG. 10D
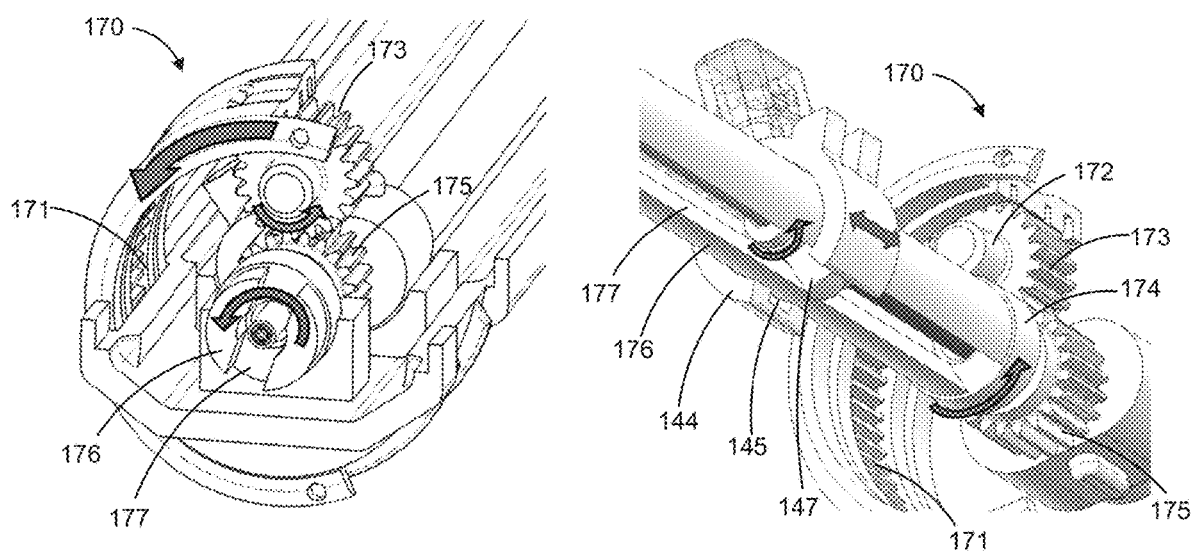
FIG. 10E
FIG. 10F

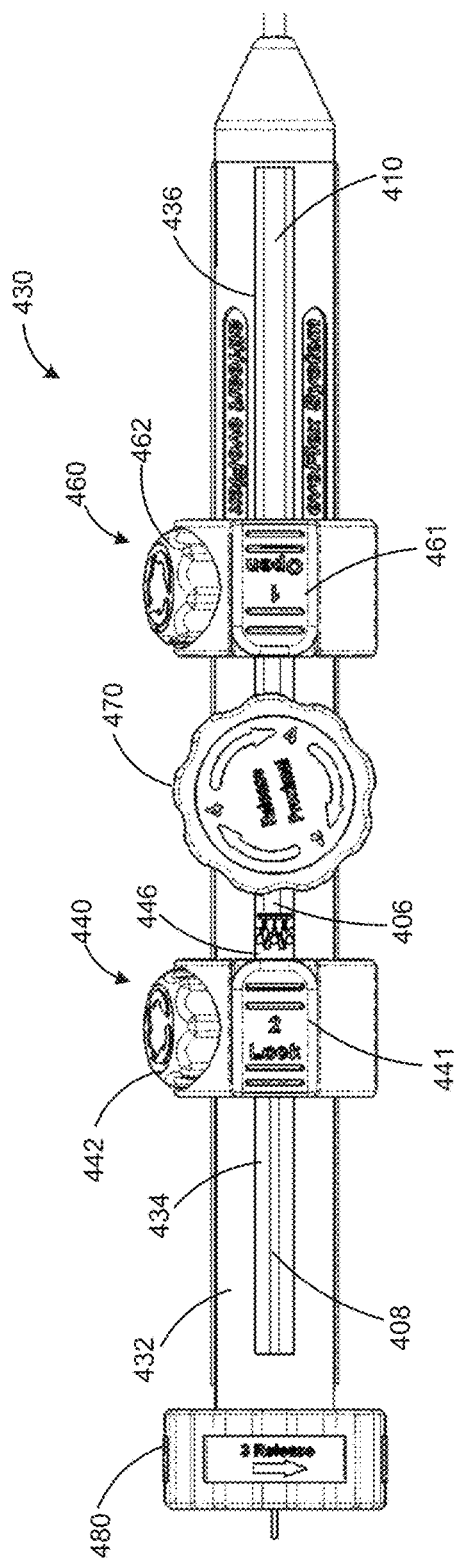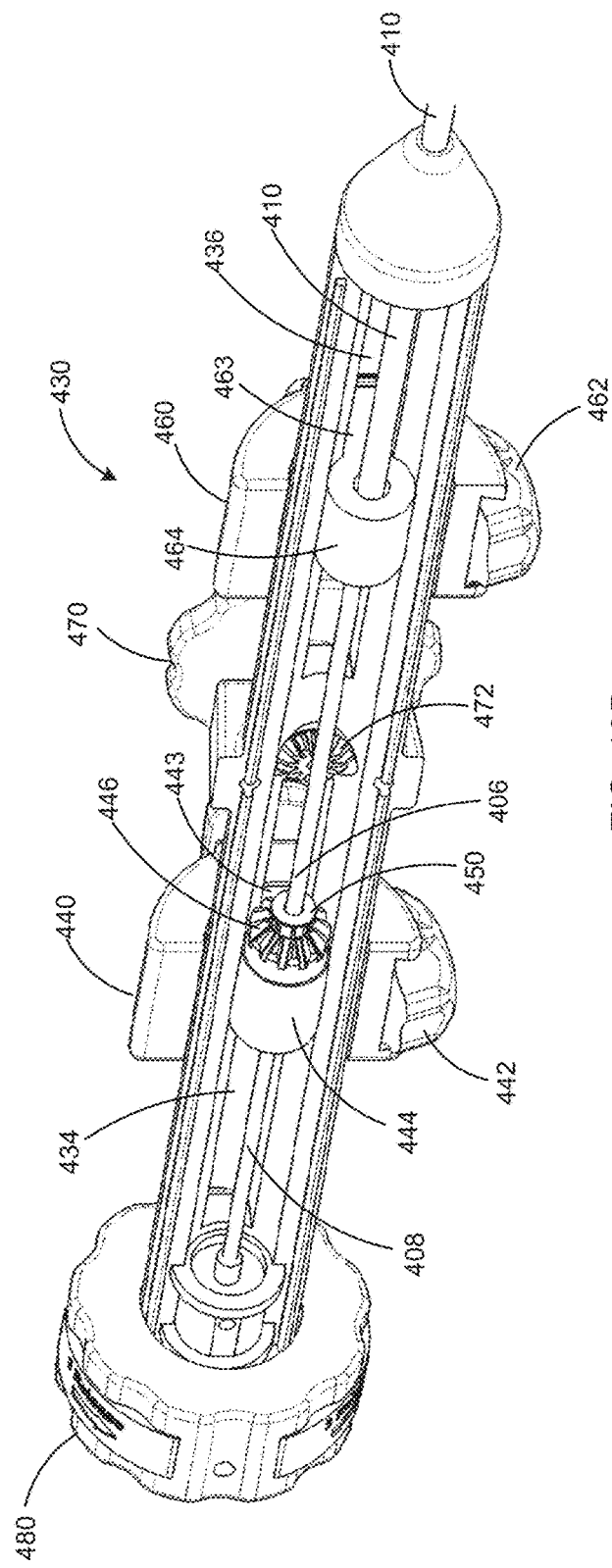
FIG. 19A
FIG. 19B

SYSTEMS AND METHODS FOR DELIVERING IMPLANTABLE OCCLUDER DEVICES FOR TREATING ATRIAL SEPTAL DEFECTS

CROSS-REFERENCE TO RELATED APPLICATIONS

This application claims the benefit of priority to U.S. Provisional Patent Appl. No. 63/563,834, filed Mar. 11, 2024, and U.S. Provisional Patent Appl. No. 63/591,727, filed Oct. 19, 2023, the entire contents of each of which are incorporated herein by reference.

FIELD OF USE

This technology is directed to systems and methods for delivering implantable occluder devices to the atrial septum, particularly in patients with heart pathologies such as atrial septal defects (ASD).

BACKGROUND

An atrial septal defect (ASD) is a congenital heart defect that can occur when the septum, the wall that separates the left and right atria in the heart, does not form or close properly. Commonly referred to as "hole in the heart," an ASD causes oxygen-rich blood to mix in the oxygen-poor chamber, which would not otherwise occur. This increases blood flow to the lungs and over time, may lead to high blood pressure, arrhythmia, heart failure or an increased risk of stroke.

ASDs vary in size. Some ASDs may close on their own early in life, while others require an intervention. Today, the vast majority are performed through minimally invasive catheter-based interventions, which consist of implanting an atrial septal occluder through a transcatheter procedure to close the defect. Current ASD occluder devices have dense metal frames that permanently clamp the septum. The long-term presence of metal in the heart may lead to potential complications and may limit future interventions that require crossing the interatrial septum.

In view of the foregoing drawbacks of previously known systems and methods, there exists a need for an improved ASD occluder device, and a delivery system for delivering the occluder device to the atrial septum.

SUMMARY

The present disclosure overcomes the drawbacks of previously-known systems and methods by providing an apparatus for delivering an occluder to an atrial septum of a patient, the occluder configured to transition between a collapsed delivery state and an expanded deployed state. For example, the apparatus may include an inner shaft having a proximal region and a distal region comprising a first engagement portion configured to be removably coupled to a distal end of the occluder, and an outer shaft slidably disposed over the inner shaft. The outer shaft may have a proximal region and a distal region comprising a second engagement portion configured to be removably coupled to a proximal end of the occluder. The apparatus further may include an outer sheath slidably disposed over the outer shaft. The outer sheath may have a proximal region, a distal region, and a lumen sized and shaped to receive the occluder in the collapsed delivery state. The distal region of the outer sheath may comprise an expandable structure and may be configured to transition from a collapsed delivery configuration defining an atraumatic tip to an expanded configuration upon application of force to the distal region of the outer sheath, the expanded configuration sized and shaped to receive the occluder therethrough.

The inner shaft may have a lumen sized and shaped to receive a guidewire therethrough. Moreover, an outer surface of the first engagement portion may comprise a threaded surface configured to be removably coupled to a threaded surface of the distal end of the occluder. Accordingly, the outer shaft may be configured to be rotated to decouple the threaded surface of the first engagement portion from the threaded surface of the distal end of the occluder. In addition, an inner surface of the second engagement portion may comprise a threaded surface configured to be removably coupled to a threaded surface of the proximal end of the occluder. Accordingly, the inner shaft may be configured to be rotated to decouple the threaded surface of the second engagement portion from the threaded surface of the proximal end of the occluder. Relative movement between the inner and outer shafts may cause the occluder to transition between the collapsed delivery state and the expanded deployed state. In the collapsed delivery configuration, a cross-sectional area of the distal portion of the distal region of the outer sheath may decrease from a proximal end of the distal portion towards a distal end of the distal portion to thereby define the atraumatic tip. Moreover, the distal portion of the distal region of the outer sheath may be biased towards the collapsed delivery configuration.

In some embodiments, the apparatus further may include a fixed shaft disposed within the lumen of the outer sheath, and the expandable structure may comprise a braided structure having a first end region coupled to the distal region of the outer sheath, and a second end region coupled to a distal region of the fixed shaft, such that the braided structure folds within itself at an inversion point, to thereby divide the braided structure into an outer region and an inner region. Accordingly, relative movement between the outer sheath and the fixed shaft may cause the inversion point to move axially along a longitudinal axis of the apparatus. For example, the braided structure may comprise Nitinol. Moreover, at least a portion of the braided structure adjacent the inversion point may be configured to expand radially outward to an expanded state upon application of force to the at least the portion of the braided structure responsive to distal movement of the outer sheath relative to the fixed shaft. Further, the at least the portion of the braided structure may comprise a cone shape in the expanded state.

The inversion point may define an opening configured to facilitate loading of the occluder within the lumen of the outer sheath in the collapsed delivery state as the outer sheath moves distally relative to the fixed shaft, and the inner region of the braided structure may be configured to contact and envelop the occluder in the collapsed delivery state as the outer sheath moves distally relative to the fixed shaft. The first end region of the braided structure may be coupled to the distal region of the outer sheath along a fixed length of the distal region of the outer sheath, such that the fixed length remains constant as the outer sheath moves relative to the fixed shaft. Moreover, the fixed shaft may comprise an attachment ring disposed at the distal region of the fixed shaft, the attachment ring configured to be coupled to the first end region of the braided structure, and a crimper ring configured to be disposed over the first end region of the braided structure at the distal region of the fixed shaft to maintain coupling between the first end region of the braided structure and the attachment ring. In the collapsed delivery configuration, the inversion point may be aligned with a distal end of the atraumatic tip. In addition, the braided structure may comprise a coating configured to prevent thrombus.

The apparatus further may include a handle operatively coupled to the proximal regions of the inner shaft, the outer shaft, the fixed shaft, and the outer sheath. The handle may comprise a first slidable actuator configured to be actuated to move the outer sheath relative to the fixed shaft to transition the braided structure between an elongated collapsed configuration where the distal regions of the outer and inner shafts are exposed from the outer sheath, and the collapsed delivery configuration where the distal regions of the outer and inner shafts are disposed within the lumen of the outer sheath, a second slidable actuator configured to be actuated to move the outer shaft relative to the inner shaft to transition the occluder between the collapsed delivery state and the expanded deployed state, a third rotatable actuator configured to be actuated to decouple the first engagement portion of the outer shaft from the proximal end of the occluder, and a fourth rotatable actuator configured to be actuated to decouple the second engagement portion of the inner shaft from the distal end of the occluder when the occluder is disposed at the atrial septum. For example, the first slidable actuator may comprise a pusher configured to be actuated to permit axial movement of the first slidable actuator relative to the handle, the pusher comprising a locking pin configured to releasably engage with a groove of a plurality of indexing grooves of the handle when the pusher is in an unactuated state to thereby lock the first slidable actuator relative to the handle, and a compression spring coupled to the pusher, the compression spring configured to bias the pusher towards the unactuated state.

The second slidable actuator may comprise a pusher configured to be actuated to permit axial movement of the second slidable actuator relative to the handle, the pusher comprising a locking pin configured to releasably engage with a groove of a plurality of indexing grooves of the handle when the pusher is in an unactuated state to thereby lock the second slidable actuator relative to the handle, and a compression spring coupled to the pusher, the compression spring configured to bias the pusher towards the unactuated state. Moreover, the second slidable actuator may comprise a frame comprising a track extending circumferentially along an inner surface of the frame, the track extending in a plane perpendicular to a longitudinal axis of the outer shaft, and a connector fixedly coupled to the proximal region of the outer shaft and rotatably disposed within the frame, the connector comprising one or more pins configured to slidably engage with the track of the frame. Accordingly, movement of the one or more pins along the track may cause rotation of the outer shaft.

The third rotatable actuator may comprise a sun gear configured to be rotated in response to rotation of the third rotatable actuator, and a transmission shaft extending proximally from the sun gear and at least partially disposed within a lumen of the frame of the second slidable actuator, the transmission shaft comprising a lumen sized and shaped to slidably receive the outer shaft therethrough, and a track extending longitudinally along a length of the transmission shaft, the track sized and shaped to receive the one or more pins of the connector of the second slidable actuator therethrough. Accordingly, rotation of the transmission shaft may cause the one or more pins to move along the track of the frame via engagement between the track of the transmission shaft and the one or more pins. In addition, the third rotatable actuator may comprise a planet gear having a geared outer surface, the planet gear disposed between an inner geared surface of the third rotatable actuator and a geared outer surface of the sun gear, such that rotation of the third rotatable actuator in a first direction about the handle causes rotation of the planet gear in the first direction via the inner geared surface and the geared outer surface of the planet gear, which causes rotation of the sun gear in a second direction opposite the first direction via the geared outer surfaces of the planet gear and the sun gear. The third rotatable actuator further may include a connector configured to be fixedly coupled to the proximal region of the fixed shaft. In addition, the fourth rotatable actuator may comprise a locking mechanism configured to transition from a locked state where rotation of the fourth rotatable actuator is prevented, and an unlocked state where rotation of the fourth rotatable actuator is permitting. For example, the locking mechanism may comprise a slidable latch.

In some embodiments, the outer sheath may comprise a pre-formed bend configured to facilitate alignment of the occluder with the atrial septum. Alternatively, the outer sheath may comprise a steerable zone configured to be actuated to form a bend along the outer sheath to facilitate alignment of the occluder with the atrial septum. In some embodiments, the apparatus may include a steerable shaft disposed over the outer shaft. The steerable shaft may be configured to be actuated to form one or more bends along a distal region of the steerable shaft to facilitate alignment of the occluder with the atrial septum. For example, the steerable shaft may be configured to be actuated to form a proximal bend and a distal bend along the distal region of the steerable shaft, the proximal and distal bends defining an S-shape. Moreover, the steerable shaft may be fixedly coupled to the outer shaft.

In some embodiments, the expandable structure may comprise a plurality of longitudinally extending struts, such that at least a distal portion of the plurality of longitudinally extending struts may be configured to transition from the collapsed delivery configuration defining an atraumatic tip to the expanded configuration upon application of force to an inner surface of the at least the distal portion of the plurality of longitudinally extending struts, the expanded configuration sized and shaped to receive the occluder therethrough. The distal region of the outer sheath may comprise an expandable membrane encapsulating the plurality of longitudinally extending struts. The distal portion of the plurality of longitudinally extending struts may comprise a transition zone and a distal zone, such that, in the collapsed delivery configuration, the cross-sectional area of the distal portion may decrease along the transition zone in a direction towards the distal zone, and the cross-sectional area of the distal portion may be constant along the distal zone. In addition, in the expanded configuration, a cross-sectional area of the distal portion of the plurality of longitudinally extending struts may increase from a proximal end of the distal portion towards a distal end of the distal portion to thereby receive the occluder therethrough. In some embodiments, the plurality of longitudinally extending struts may comprise a plurality of longitudinally extending U-shaped struts circumferentially disposed about the distal region of the outer sheath to define the lumen of the outer sheath. Relative movement between the occluder and the at least the distal portion of the plurality of longitudinally extending struts may cause the occluder to apply the force to the inner surface of the at least the distal portion of the plurality of longitudinally extending struts to transition the at least the distal portion of the plurality of longitudinally extending struts from the collapsed delivery configuration to the expanded configuration.

The apparatus further may include a handle operatively coupled to the proximal regions of the inner shaft, the outer shaft, and the outer sheath. The handle may include a first slidable actuator configured to be actuated to move the outer sheath relative to the outer shaft to thereby expose and/or recapture the occluder within the lumen of the outer sheath, a second slidable actuator configured to be actuated to move the outer shaft relative to the inner shaft to transition the occluder between the collapsed delivery state and the expanded deployed state, a third rotatable actuator configured to be actuated to decouple the first engagement portion of the outer shaft from the proximal end of the occluder, and a fourth rotatable actuator configured to be actuated to decouple the second engagement portion of the inner shaft from the distal end of the occluder when the occluder is disposed at the atrial septum.

The second slidable actuator may be configured to move between a first position and a second position along the handle, and may comprise a first rotatable bevel gear operatively coupled to the outer shaft and configured to engage with a second rotatable bevel gear of the third rotatable actuator when the second slidable actuator is in the second position, such that rotation of the third rotatable actuator may cause rotation of the outer shaft via the first and second rotatable bevel gears. Additionally, the second slidable actuator further may comprise a splined rotary shaft fixedly coupled to the outer shaft and disposed within a lumen of the first rotatable bevel gear. An inner surface of the lumen of the first rotatable bevel gear may comprise a plurality of grooves configured to engage with a plurality of splines disposed on an outer surface of the splined rotary shaft in a manner that permits relative translational movement between the first rotatable bevel gear and the splined rotary shaft, but prohibits relative rotational movement between the first rotatable bevel gear and the splined rotary shaft to thereby operatively couple the first rotatable bevel gear to the outer shaft.

Moreover, the splined rotary shaft may comprise a lip at its distal end, and the second slidable actuator further may comprise one or more springs coupled to a proximal end of the first rotatable bevel gear. The one or more springs may be configured to push the first rotatable bevel gear against the lip of the splined rotary shaft to maintain contact between the first rotatable bevel gear and the splined rotary shaft. In addition, the second slidable actuator further may comprise a washer having a lumen sized and shaped to receive at least a portion of the splined rotary shaft therethrough. The washer may be configured to prevent relative translational movement between the splined rotary shaft and the second slidable actuator, while permitting relative rotational movement between the splined rotary shaft and the second slidable actuator. In addition, the first slidable actuator may comprise a first locking mechanism configured to be actuated to lock the first slidable actuator relative to the handle, and the second slidable actuator may comprise a second locking mechanism configured to be actuated to lock the second slidable actuator relative to the handle. Moreover, rotation of the fourth rotatable actuator may cause rotation of the inner shaft to thereby decouple the second engagement portion of the inner shaft from the distal end of the occluder when the occluder is disposed at the atrial septum.

In accordance with another aspect of the present disclosure, a system comprising the apparatus and the occluder is provided. The occluder further may include a plurality of bioresorbable filaments extending between the proximal and distal ends of the occluder, and defining a proximal portion, a central portion, and a distal portion of the occluder. For example, the plurality of bioresorbable filaments may be arranged to transition between an elongated configuration in the collapsed delivery state and an expanded configuration in the expanded deployed state where the proximal and distal portions of the occluder expand radially outward and the central portion contracts radially inward. In addition, the occluder may include a biocompatible fabric disposed on at least the proximal and distal portions of the occluder. The proximal and distal portions of the occluder may be configured to sandwich the atrial septum in the expanded deployed state, such that the central portion of the occluder is disposed within the atrial septum.

In accordance with yet another aspect of the present disclosure, an apparatus for delivering an occluder to an atrial septum of a patient is provided. The apparatus may include a first actuator operatively coupled to an outer shaft having a distal region configured to be removably coupled to a proximal end of the occluder, the first actuator configured to move axially between a first position on the handle body where the occluder is in the collapsed delivery state, and a second position on the handle body where the occluder is in the expanded deployed state, and a second actuator disposed on the handle body, the second actuator configured to be actuated to decouple the distal region of the outer shaft from the proximal end of the occluder. For example, the first actuator may comprise a frame comprising a track extending circumferentially along an inner surface of the frame, the track extending in a plane perpendicular to a longitudinal axis of the outer shaft, and a connector fixedly coupled to the proximal region of the outer shaft and rotatably disposed within the frame, the connector comprising one or more pins configured to slidably engage with the track of the frame. Moreover, the second actuator may comprise a sun gear configured to be rotated in response to rotation of the second actuator, and a transmission shaft extending proximally from the sun gear and at least partially disposed within a lumen of the frame of the first actuator, the transmission shaft comprising a lumen sized and shaped to slidably receive the outer shaft therethrough, and a track extending longitudinally along a length of the transmission shaft, the track sized and shaped to receive the one or more pins of the connector of the first actuator therethrough. Accordingly, upon rotation of the second actuator, rotation of the sun gear may cause rotation of the transmission shaft, which causes the one or more pins to move along the track of the frame via engagement between the track of the transmission shaft and the one or more pins, thereby rotating the outer shaft via the connector of the first actuator.

The slidable actuator may comprise a pusher configured to be actuated to permit axial movement of the slidable actuator relative to the handle body, the pusher comprising a locking pin configured to releasably engage with a groove of a plurality of indexing grooves of the handle body when the pusher is in an unactuated state to thereby lock the slidable actuator relative to the handle body, and a compression spring coupled to the pusher, the compression spring configured to bias the pusher towards the unactuated state. In addition, the rotatable actuator may comprise a planet gear having a geared outer surface, the planet gear disposed between an inner geared surface of the rotatable actuator and a geared outer surface of the sun gear, such that rotation of the rotatable actuator in a first direction about the handle causes rotation of the planet gear in the first direction via the inner geared surface and the geared outer surface of the planet gear, which causes rotation of the sun gear in a second direction opposite the first direction via the geared outer surfaces of the planet gear and the sun gear. Moreover, the apparatus further may comprise a second slidable actuator coupled to an outer sheath slidably disposed over the outer shaft, the outer sheath having a lumen sized and shaped to receive the occluder in the collapsed delivery state. The second slidable actuator may be configured to move between a third position on the handle body where the occluder is disposed within the lumen of the outer sheath in the collapsed delivery state, and a fourth position on the handle body where the occluder is exposed beyond a distal end of the outer sheath. Further, the apparatus may comprise a second rotatable actuator coupled to an inner shaft slidably disposed within the outer shaft, the inner shaft having a distal region configured to be removably coupled to a distal end of the occluder. Accordingly, rotation of the second rotatable actuator causes rotation of the inner shaft to thereby decouple the distal region of the inner shaft from the distal end of the occluder when the occluder is disposed at the atrial septum.

In accordance with another aspect of the present disclosure, an apparatus for delivering an occluder to an atrial septum of a patient is provided. The apparatus may include a handle body, a slidable actuator comprising a first rotatable bevel gear operatively coupled to an outer shaft having a distal region configured to be removably coupled to the occluder, and a rotatable actuator comprising a second rotatable bevel gear. The slidable actuator may be configured to move between a first position on the handle body where the occluder is in a collapsed delivery state, and a second position on the handle body where the occluder is in an expanded deployed state. Moreover, the rotatable actuator may be disposed on the handle body such that, when the slidable actuator is in the second position, the second rotatable bevel gear engages with the first rotatable bevel gear such that rotation of the rotatable actuator may cause rotation of the outer shaft via the first and second rotatable bevel gears to thereby decouple the distal region of the outer shaft from the occluder.

In addition, the slidable actuator further may comprise a splined rotary shaft fixedly coupled to the outer shaft and disposed within a lumen of the first rotatable bevel gear. An inner surface of the lumen of the first rotatable bevel gear may comprise a plurality of grooves configured to engage with a plurality of splines disposed on an outer surface of the splined rotary shaft in a manner that permits relative translational movement between the first rotatable bevel gear and the splined rotary shaft, but prohibits relative rotational movement between the first rotatable bevel gear and the splined rotary shaft to thereby operatively couple the first rotatable bevel gear to the outer shaft. The splined rotary shaft may comprise a lip at its distal end, and the slidable actuator further may comprise one or more springs coupled to a proximal end of the first rotatable bevel gear. The one or more springs may be configured to push the first rotatable bevel gear against the lip of the splined rotary shaft to maintain contact between the first rotatable bevel gear and the splined rotary shaft. The slidable actuator further may comprise a washer having a lumen sized and shaped to receive at least a portion of the splined rotary shaft therethrough. The washer may be configured to prevent relative translational movement between the splined rotary shaft and the slidable actuator, while permitting relative rotational movement between the splined rotary shaft and the slidable actuator. The slidable actuator may comprise a locking mechanism configured to be actuated to lock the slidable actuator relative to the handle body.

The distal region of the outer shaft may be configured to be removably coupled to a proximal end of the occluder. Accordingly, the apparatus further may comprise a second slidable actuator coupled to an outer sheath slidably disposed over the outer shaft, the outer sheath having a lumen sized and shaped to receive the occluder in the collapsed delivery state. The second slidable actuator may be configured to move between a third position on the handle body where the occluder is disposed within the lumen of the outer sheath in the collapsed delivery state, and a fourth position on the handle body where the occluder is exposed beyond a distal end of the outer sheath. In addition, the apparatus further may include a second rotatable actuator coupled to an inner shaft slidably disposed within the outer shaft, the inner shaft having a distal region configured to be removably coupled to a distal end of the occluder. Accordingly, rotation of the second rotatable actuator may cause rotation of the inner shaft to thereby decouple the distal region of the inner shaft from the distal end of the occluder when the occluder is disposed at the atrial septum. The second slidable actuator may comprise a locking mechanism configured to be actuated to lock the second slidable actuator relative to the handle body.

In accordance with another aspect of the present disclosure, a method for delivering an occluder to an atrial septum of a patient, the occluder configured to transition between a collapsed delivery state and an expanded deployed state, is provide. The method may comprise: removably coupling a distal region of an inner shaft to a distal end of the occluder via a first engagement portion at the distal region of the inner shaft; removably coupling a distal region of an outer shaft to a proximal end of the occluder via a second engagement portion at the distal region of the outer shaft, the outer shaft slidably disposed over the inner shaft within an outer sheath; moving the outer shaft proximally relative to the inner shaft to transition the occluder from an expanded deployed state towards a collapsed delivery state; and moving the outer sheath distally relative to the outer shaft to apply a force to an expandable structure at a distal region of the outer sheath and transition the expandable structure from an expanded configuration to receive the occluder therethrough to a collapsed delivery configuration defining an atraumatic tip. In some embodiments, the expandable structure may comprise a braided structure having a first end region coupled to the distal region of the outer sheath, and a second end region coupled to a distal region of a fixed shaft disposed within a lumen of the outer sheath. Accordingly, moving the outer sheath distally relative to the outer shaft to apply the force to the expandable structure may cause the braided structure to fold within itself at an inversion point, the inversion point defining an opening and dividing the braided structure into an outer region and an inner region. Moreover, moving the outer sheath distally relative to the outer shaft may cause the inner region of the braided structure to contact and envelop the occluder in the collapsed delivery state as the outer sheath moves distally relative to the fixed shaft.

In addition, the method may comprise: advancing the outer shaft, the inner shaft, and the outer sheath having the occluder disposed therein in the collapsed delivery state to the atrial septum, such that a distal portion of the occluder is disposed within a first atrium and a proximal portion of the occluder is disposed within a second atrium; moving the outer sheath proximally relative to the outer and inner shafts to expose the distal portion of the occluder within the first atrium and the proximal portion of the occluder within the second atrium; moving the outer shaft distally relative to the inner shaft to transition the occluder from the collapsed delivery state to the expanded deployed state, such that the proximal and distal portions of the occluder sandwich the atrial septum in the expanded deployed state; rotating the outer shaft to decouple the distal region of the outer shaft from the proximal end of the occluder; rotating the inner shaft to decouple the distal region of the inner shaft from the distal end of the occluder; and removing the outer sheath and the inner and outer shafts from the patient. For example, moving the outer sheath may comprise moving a first slidable actuator of a handle coupled to a proximal region of the outer sheath axially relative to the handle, moving the outer shaft may comprise moving a second slidable actuator of the handle operatively coupled to a proximal region of the outer shaft axially relative to the handle, rotating the outer shaft may comprise rotating a third rotatable actuator of the handle operatively coupled to the proximal region of the outer shaft, and rotating the inner shaft may comprise actuating a fourth rotatable actuator of the handle coupled to a proximal region of the inner shaft. Moreover, rotating the third rotatable actuator of the handle may comprise rotating a sun gear and a transmission shaft coupled thereto, the transmission shaft extending through a frame of the second slidable actuator and comprising a longitudinally extending track, such that rotation of the transmission shaft causes rotation of a connector within the frame via one or more pins of connector extending through the longitudinally extending track of the transmission shaft, the connector coupled to the proximal region of the outer shaft.

BRIEF DESCRIPTION OF THE DRAWINGS

FIG. 2A illustrates an exemplary implantable occluder device constructed in accordance with the principles of the present disclosure.

FIG. 2B illustrates the proximal end of the occluder device of FIG. 2A, and FIG. 2C illustrates the distal end of the occluder device of FIG. 2A.

FIGS. 7A and 7B illustrate an exemplary handle of the delivery system of FIG. 1 constructed in accordance with the principles of the present disclosure.

FIGS. 9A to 9F illustrate an exemplary slidable outer shaft actuator of the handle of FIGS. 7A and 7B.

FIGS. 10A to 10F illustrate an exemplary rotatable outer shaft actuator of the handle of FIGS. 7A and 7B.

FIGS. 19A and 19B illustrate an exemplary handle of the delivery system of FIG. 16 constructed in accordance with the principles of the present disclosure.

DETAILED DESCRIPTION

The present disclosure is directed to systems and methods for delivering an implantable occluder device to the atrial septum of a patient's heart for treating patients suffering from an atrial septal defect (ASD). For example, the delivery system may be designed to deliver a low-profile ASD occluder device having a metal-free, bioresorbable frame designed for the closure of atrial septal defects. The low-profile occluder device may include bioresorbable filaments connecting two polyester fabric patches, which may contain radiopaque markers. The delivery system may advance the occluder in a collapsed delivery state over a guidewire to the atrial septum, and may fully deploy the occluder device at the atrial septum with the guidewire in place, providing the opportunity to reattach and reposition the occluder device if necessary. After endothelialization, the bioresorbable filaments slowly resorb, with complete resorption within, e.g., 24 months, such that the polyester fabric and the radiopaque markers remain at the atrial septum, which may be useful for future transseptal procedure planning.

Figure 1:
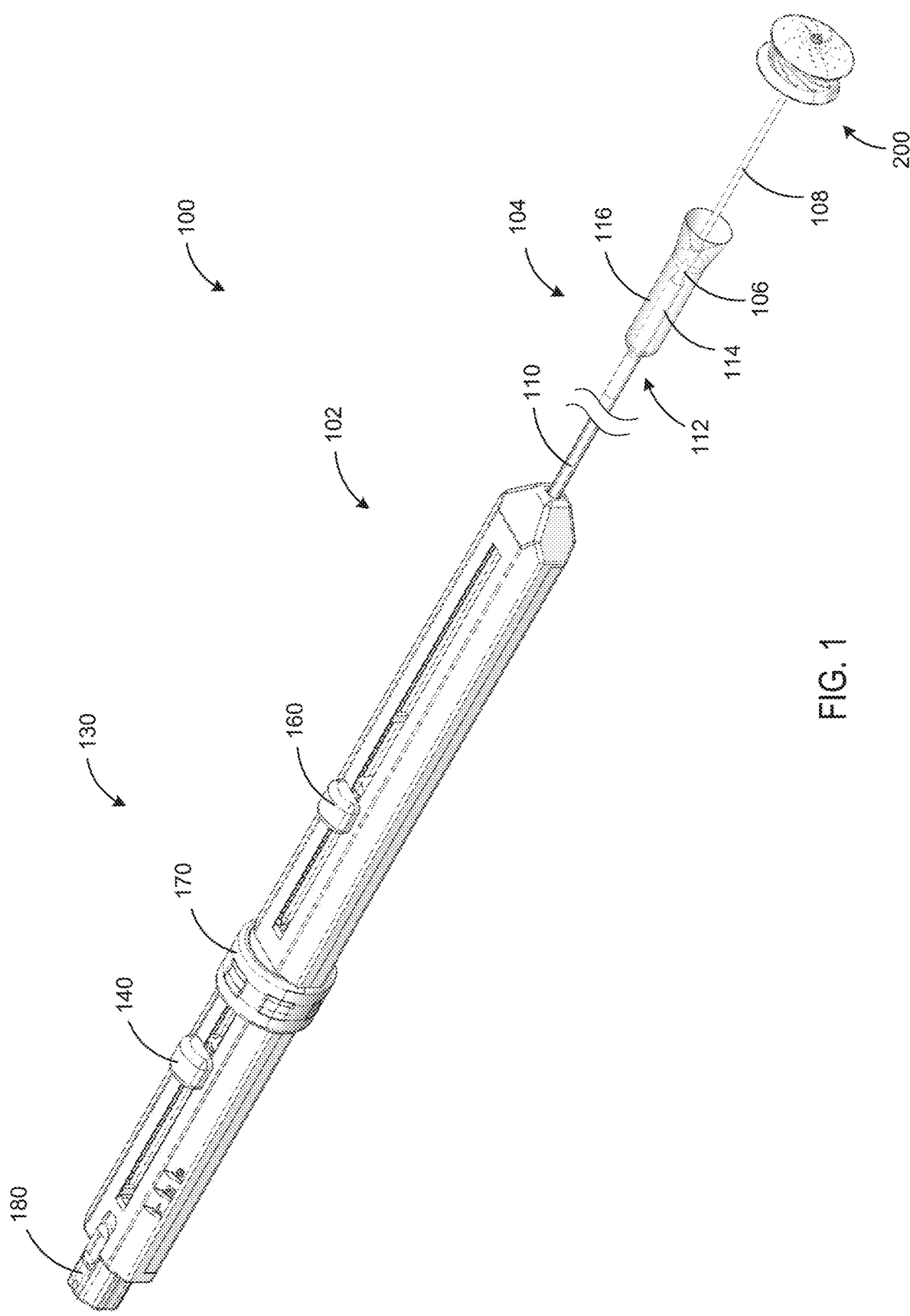
FIG. 1 illustrates an exemplary system for delivering an implantable occluder device to an atrial septum constructed in accordance with the principles of the present disclosure.

Referring now to FIG. 1, an exemplary system for delivering an implantable occluder device to an atrial septum of a patient's heart is provided. Delivery system 100 may be configured to deliver an ASD occluder device, e.g., occluder 200, to the atrial system in a collapsed delivery state within system 100, and may further may be actuated to deploy occluder 200 at the atrial septum to thereby close the atrial septal defect. As shown in FIG. 1, system 100 may include handle 130 at proximal region 102, a plurality of coaxial elongated components, e.g., outer shaft 106, inner shaft 108, fixed shaft 114, outer sheath 110, operatively coupled to and extending from handle 130 towards distal region 104 where system 100 may be removably coupled to occluder 200 for delivery. The distal region of system 100 further may include an expandable, sock-like braided structure 116 formed of a shape-memory material, e.g., Nitinol and/or highly flexible material, and coupled to the distal regions of outer sheath 110 and fixed shaft 114, such that, upon actuation at handle 130, braided structure 116 may invert/evert (e.g., fold over itself) to transition between an elongated collapsed configuration, e.g., for coupling occluder 200 to outer shaft 106 and inner shaft 108, and a collapsed delivery configuration, e.g., for loading occluder 200 within outer sheath 110 and for delivering occluder 200 at the atrial septum, as described in further detail below with regarding to FIG. 4.

For example, the distal region of outer shaft 106 may be removably coupled to a proximal end of occluder 200, and the distal region of inner shaft 108 slidably disposed within a lumen of outer shaft 106 may be removably coupled to a distal end of occluder 200, such that, upon actuation at handle 130, relative movement between outer shaft 106 and inner shaft 108 may cause occluder 200 to transition between the collapsed delivery state and an expanded deployed state. Moreover, upon further actuation at handle 130, outer shaft 106 and inner shaft 108 may be decoupled from occluder 200, and system 100 may be removed from the patient, leaving occluder 200 implanted at the atrial septum.

Figure 2D:
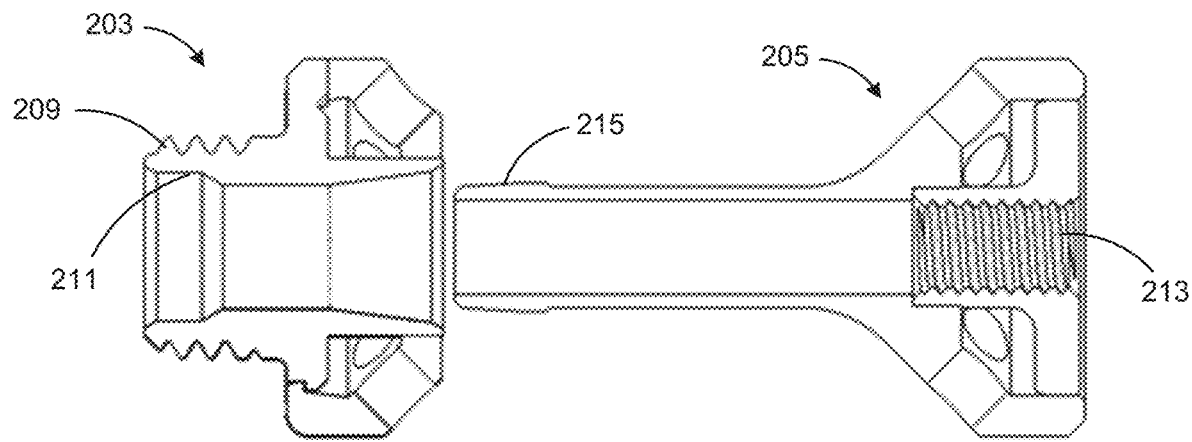
FIGS. 2D and 2E illustrate the snap fit connection between the proximal end of FIG. 2B and the distal end of FIG. 2C.

Referring now to FIGS. 2A to 2G, an exemplary implantable occluder device is provided. As shown in FIG. 2A, occluder 200 may include a plurality of bioresorbable wire-like filaments, e.g., filaments 206, extending between proximal end 203 and distal end 205 of occluder 200. FIG. 2B is a perspective view of proximal end 203 of occluder 200, and FIG. 2C is a perspective view of distal end 205 of occluder 200. Proximal end 203 may be configured to removably engage with an engagement portion at the distal region of outer shaft 106. As described in further detail below, the distal region of outer shaft 106 may include threaded surface 107, e.g., disposed on inner surface of the lumen of outer shaft 106. As shown in FIG. 2B, the outer surface of proximal end 203 may have threaded surface 209 configured to removably engage with threaded surface 107 of outer shaft 106, e.g., via relative rotation between outer shaft 106 and proximal end 203. Moreover, as described in further detail below, the distal region of inner shaft 108 may include threaded surface 109, e.g., disposed on an outer surface at the distal region of inner shaft 108. As shown in FIG. 2D, at least a portion of the inner surface of a lumen of distal end 205 may have threaded surface 213 configured to removably engage with threaded surface 109 of inner shaft 108, e.g., via relative rotation between inner shaft 108 and distal end 205. Accordingly, the lumen of distal end 205 may be sized and shaped to receive inner shaft 108 therethrough.

Figure 2E:
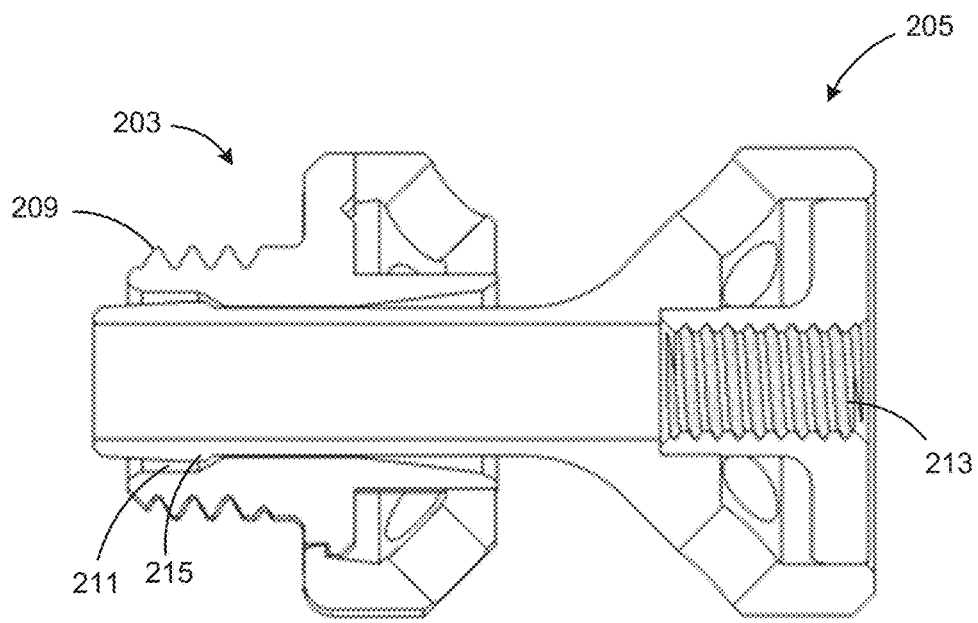

In addition, proximal end 203 and distal end 205 of occluder 200 may be locked together when occluder 200 is in its expanded deployed state, e.g., when proximal end 203 is moved towards and engages with distal end 205 via distal movement of outer shaft 106 relative to inner shaft 108, to thereby lock occluder 200 in its full expanded deployed state. For example, as shown in FIG. 2D, proximal end 203 may have a lumen extending therethrough sized and shaped to receive at least an elongated portion of distal end, and the lumen may comprise groove 211 extending circumferentially along the inner surface of a proximal portion of the lumen. Groove 211 may be sized and shaped to securely receive protrusion 215 of distal end 205, e.g., via a snap fit connection. Accordingly, groove 211 may have a geometry that corresponds with the geometry of protrusion 215, such that when protrusion 215 is disposed within groove 211, proximal end 203 is securely coupled to distal end 205 in a locked state, as shown in FIG. 2E, and occluder 200 is in its fully expanded deployed and locked state. As shown in FIG. 2E, a distal portion of the lumen of proximal end 203 may be tapered to facilitate insertion of protrusion 215 through the lumen, and protrusion 215 may have an outer diameter that is slightly larger than the portion of the lumen of proximal end 203 distal to groove 211, such that when protrusion 215 is disposed within groove 211, the inner wall of the lumen distal to groove 211 prevents distal movement of distal end 205 relative to proximal end 203.

Figure 2G:
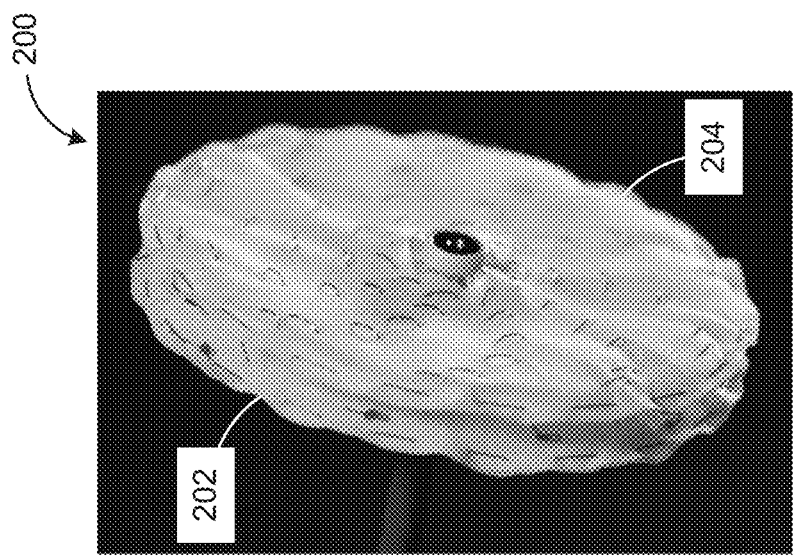
FIGS. 2F and 2G illustrate the transition of the occluder device to its expanded deployed and locked state.
Figure 2F:
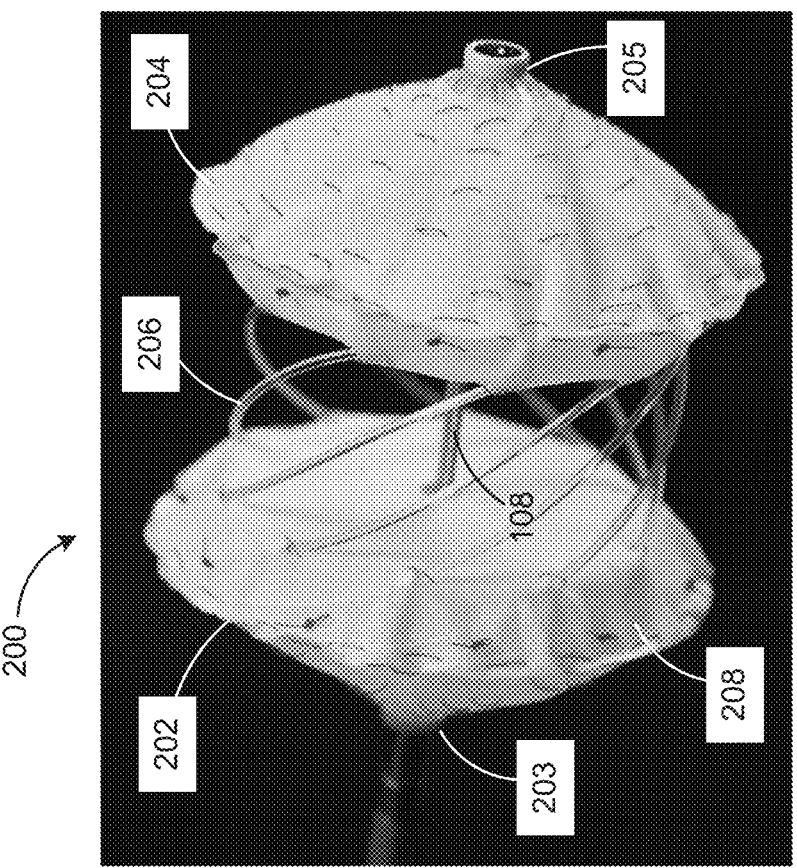

Referring again to FIG. 2A, filaments 206 may be fixedly coupled to proximal end 203 at its proximal end and fixedly coupled to distal end 205 at its distal end, and may define proximal portion 202, central portion 207, and distal portion 204 of occluder 200. Filaments 206 may be arranged in a manner such that, when occluder 200 is in its collapsed delivery state where proximal end 203 and distal end 205 are spaced apart, e.g., by a predetermined distance, proximal portion 202, central portion 207, and distal portion 204 of occluder 200 all have an elongated configuration and are radially contracted towards the longitudinal axis of occluder 200. Moreover, when occluder 200 is in its expanded deployed state where proximal end 203 and distal end 205 are moved adjacent to one another, proximal portion 202 and distal portion 204 expand radially outward, and central portion 207 contracts radially inward, as shown in FIGS. 2F and 2G. For example, filaments 206 may be arranged in a helical pattern about the longitudinal axis of occluder 200 between proximal end 203 and distal end 205. Thus, when implanted at the atrial septum, central portion 207 may extend across the atrial septal defect, such that distal portion 204 is deployed within a first atrium, e.g., the left atrium, and proximal portion 202 is deployed within a second atrium, e.g., the right atrium.

In addition, occluder 200 may include biocompatible fabric patches 208 disposed on at least proximal portion 202 and distal portion 204, and connected via filaments 206. For example, patches 208 may be sutured to filaments 206 at proximal portion 202 and distal portion 204. Patches 208 may be made from, e.g., polyester, and may include one or more radiopaque markers disposed thereon, such that occluder 200 may be visualized under fluoroscopy. As shown in FIGS. 2F to 2G, as occluder 200 transitions from the collapsed delivery state to the expanded deployed and locked state, patches 208 form disc-like structures at proximal portion 202 and distal portion 204, such that proximal portion 202 and distal portion 204 may sandwich the atrial septum in the expanded deployed and locked state. Once implanted at the atrial septum, tissue ingrowth on occluder 200, i.e., endothelialization, further secures occluder 200 at the atrial septum. Moreover, filaments 206 may resorb over time, with complete resorption within, e.g., 24 months, such that patches 208 at proximal portion 202 and distal portion 204, and accordingly the radiopaque markers, remain implanted at the atrial septum. As will be understood by a person having ordinary skill in the art, filaments 208 may be selected to completely resorb within more or less than 24 months, based on, for example, the size of the atrial septal defect. Occluder 200 may be sized to support closure of defects ranging from, e.g., 8-22 mm.

Figure 3A:
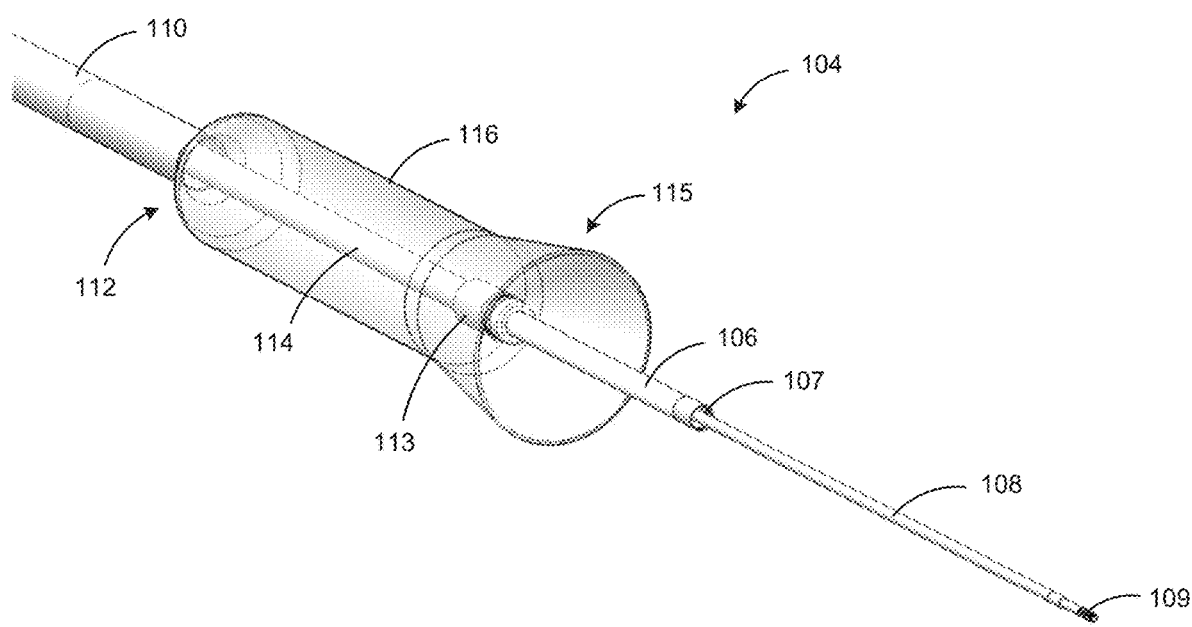
FIG. 3A illustrates the distal region of the delivery system of FIG. 1.

Referring now to FIG. 3A, the distal region of system 100 is provided. As shown in FIG. 3A, inner shaft 108 may be slidably disposed within the lumen of outer shaft 106, outer shaft 106 may be slidably disposed within the lumen of fixed shaft 114, and outer sheath 110 may be slidably disposed over fixed shaft 114, and accordingly, outer shaft 106 and inner shaft 108. Fixed shaft 114 may be fixed axially relative to handle 130. Distal region 112 of outer sheath 110 may be fixedly coupled to, or otherwise integrated with, a first end region of invertible braided structure 116, and distal region 113 of fixed shaft 114 may be fixedly coupled to, or otherwise integrated with, a second opposite end region of invertible braided structure 116, such that, upon actuation at handle 130, relative movement between outer sheath 110 and fixed shaft 114 may cause braided structure 116 to transition between an elongated collapsed configuration where a first surface of braided structure 116 faces radially outward from a longitudinal axis of system 100 and a second opposing surface of braided structure 116 faces radially inward towards the longitudinal axis of system 100, and a collapsed delivery configuration where the first surface of braided structure 116 faces radially inward towards the longitudinal axis of system 100 and the second surface of braided structure 116 faces radially outward from the longitudinal axis of system 100. As shown in FIG. 3A, the portion of braided structure 116 that inverts/everts (e.g., folds over itself) may form expanded, cone shaped portion 115, which may be sized and shaped to facilitate loading of occluder 200 therethrough as braided structure 116 is advanced over occluder 200.

Figure 3B:
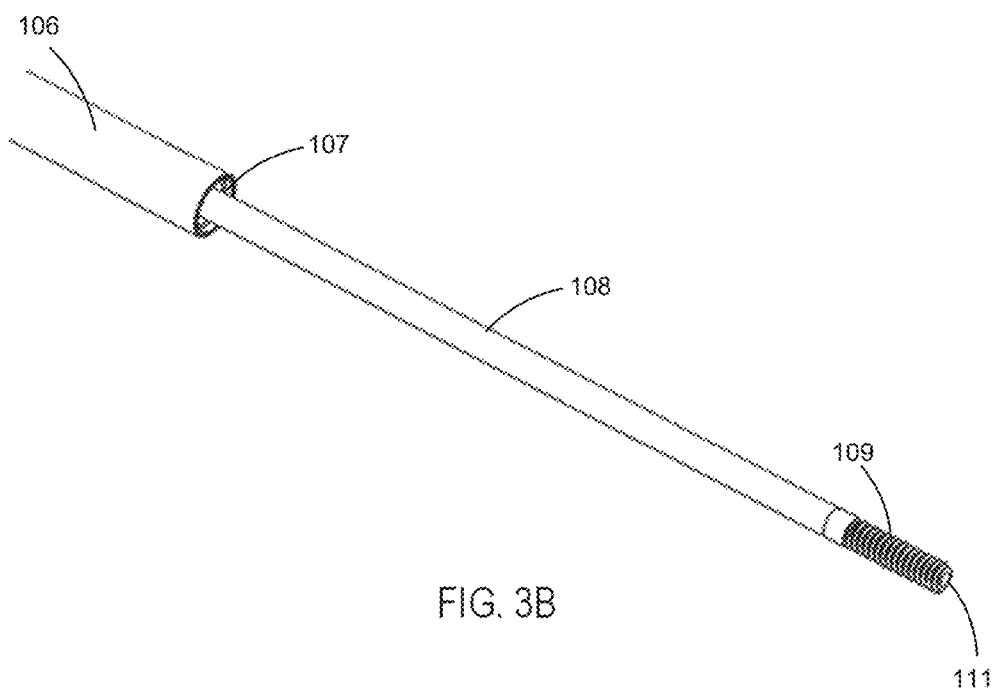
FIG. 3B illustrates exemplary inner and outer shafts of the delivery system of FIG. 1.

Referring now to FIG. 3B, the distal regions of outer shaft 106 and inner shaft 108 are provided. As shown in FIG. 3B, inner shaft 108 may be slidably disposed within the lumen of outer shaft 106, such that the distal region of inner shaft 108 extends beyond the distal end of outer shaft 106. Inner shaft 108 may include guidewire lumen 111 sized and shaped to receive a guidewire therethrough. As described above, the distal region of outer shaft 106 may have an engagement portion configured to removably engage with proximal end 203 of occluder 200, and the distal region of inner shaft 108 may have an engagement portion configured to removably engage with distal end 205 of occluder 200. For example, the inner surface of the lumen of outer shaft 106 at the distal region of outer shaft 106 may include threaded surface 107 configured to removeably engage with threaded surface 209 of proximal end 203 of occluder 200, e.g., via relative rotation between outer shaft 106 and proximal end 203. Moreover, the outer surface of the distal region of inner shaft 108 may include threaded surface 109 configured to removeably engage with threaded surface 213 of distal end 205 of occluder 200, e.g., via relative rotation between inner shaft 108 and distal end 205. As will be understood by a person having ordinary skill in the art, threaded surface 107 may be disposed on the outer surface of the distal region of outer shaft 106 if proximal end 203 has a threaded surface disposed on an inner surface of its lumen sized and shaped to receive outer shaft 106 therethrough, and similarly, threaded surface 109 may be disposed on an inner surface of a lumen of inner shaft 108 if distal end 205 has a threaded surface disposed on an outer surface configured to be received by the lumen the inner shaft 108.

When outer shaft 106 is coupled to proximal end 203 of occluder 200 and inner shaft 108 is coupled to distal end 205 of occluder 200, relative movement between outer shaft 106 and inner shaft 108 will cause occluder 200 to transition between its collapsed delivery state and its expanded deployed state. For example, the distal end of outer shaft 106 may be spaced apart from the distal end of inner shaft 108 by a distance such that occluder 200 contracts radially inward and has an elongated configuration in the collapsed delivery state. In the collapsed delivery state, occluder 200 may have an outer diameter sized to fit within the lumen of outer sheath 110, as described in further detail below with regard to FIGS. 13A to 13E. In addition, the distal end of outer shaft 106 may be positioned adjacent to the distal end of inner shaft 108 such that proximal portion 202 and distal portion 204 of occluder 200 expand radially outward in the expanded deployed state.

Figure 4:
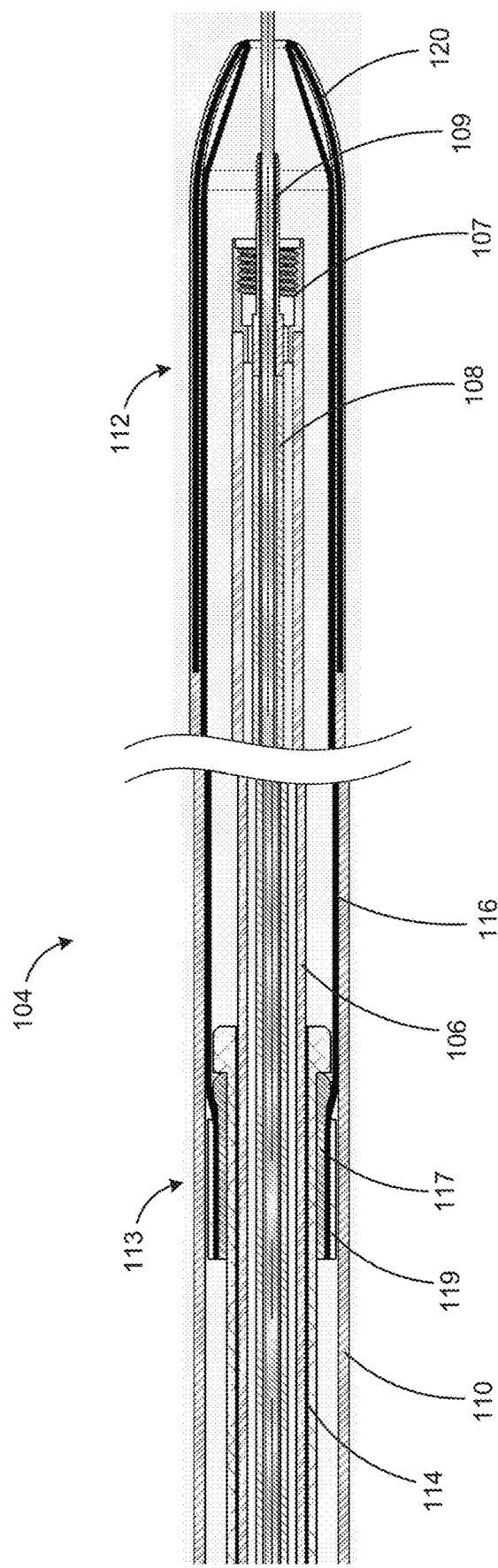
FIG. 4 is a cross-sectional view of the distal region of the delivery system of FIG. 1 in a collapsed delivery configuration.

FIG. 4 illustrates distal region 104 of system 100 when distal region 112 of outer sheath 110 is in its collapsed delivery configuration. As shown in FIG. 4, distal region 112 of outer sheath 110 may be defined by the portion/length of outer sheath 110 that is coupled to (or otherwise integrated with) the first end region of braided structure 116, and distal region 113 of fixed shaft 114 may be defined by the portion/length of fixed shaft 114 that is coupled to (or otherwise integrated with) the second end region of braided structure 116. Accordingly, as the first end region of braided structure 116 is coupled to distal region 112 of outer sheath 110 and the second end region of braided structure 116 is coupled to distal region 113 of fixed shaft 114 disposed within the lumen of outer sheath 110, braided structure 116 may invert within itself to thereby extend proximally towards distal region 113 of fixed shaft 114 from distal region 112 of outer sheath 110 in the collapsed delivery configuration. For example, as the braided structured 116 transitions from the collapsed delivery configuration towards the elongated collapsed configuration, e.g., as outer sheath 110 is retracted proximally relative to fixed shaft 114, the surface of braided structure 116 facing radially inward everts at the distal end of braided structure 116 (e.g., the inversion/eversion point) to face radially outward, and the surface of braided structure 116 facing radially outward everts at the distal end of braided structure 116 to face radially inward.

The portion of braided structure 116 extending between the distal end of distal region 112 and the distal end of distal region 113 may not be coupled to any component of system 100, such that upon retraction of outer sheath 112 relative to fixed shaft 114, the inverted portion of braided structure 116 may unfold over itself at the point of inversion, as described in further detail below with regard to FIGS. 13A to 13E. Accordingly, when occluder 200 (not shown) is coupled to outer shaft 106 and inner shaft 108 via threaded surfaces 107, 109, respectively, and disposed in a collapsed delivery state within the lumen of outer sheath 110, the freely extending portion of braided structure 116 may extend over occluder 200 within the lumen of outer sheath 110. Moreover, at least a distal portion of braided structure 116 (e.g., where braided structure folds over itself) may be configured to expand radially outwardly from the longitudinal axis of system 100, e.g., upon application of force against braided structure 116 via outer sheath 110, to form cone shaped portion 115, to thereby facilitate loading of occluder 200 within braided structure 116. In addition, when distal region 112 is in its collapsed delivery configuration, a distal portion of distal region 112 may define tip 120 of system 100. As shown in FIG. 4, the cross-sectional area of tip 120 may decrease along tip 120 in the distal direction, to thereby form an atraumatic tip configured to facilitate navigation through the patient's anatomy. The distal portion of distal region 112 may be biased towards the collapsed configuration.

Figure 5A:
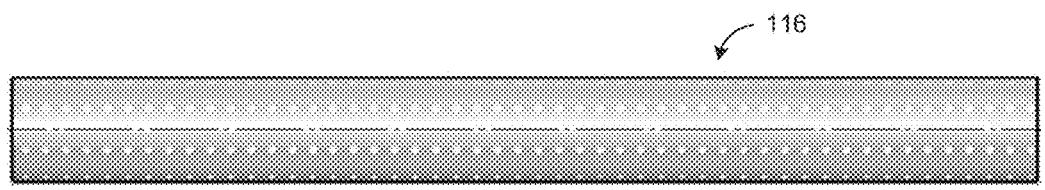
FIGS. 5A to 5F illustrate an exemplary method for assembling the exemplary invertible braided structure at the distal region of the delivery system of FIG. 1 in accordance with the principles of the present disclosure.
Figure 5B:
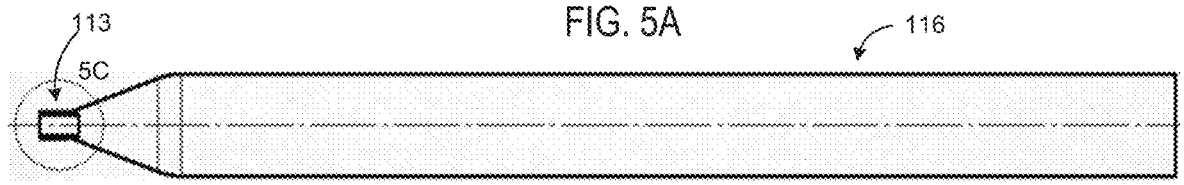
Figure 5C:
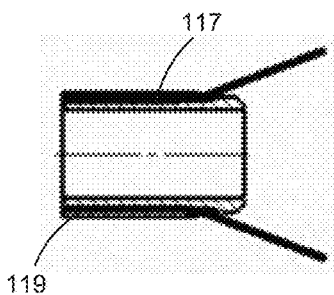
Figure 5D:
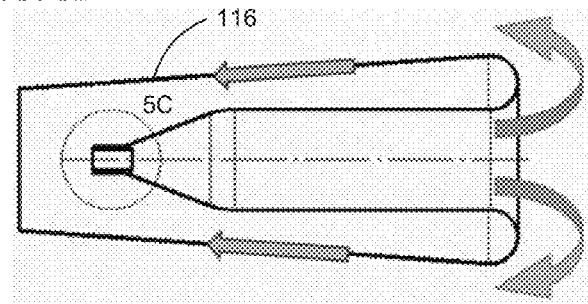

Referring now to FIGS. 5A to 5F, an exemplary method for assembling invertible braided structure 116 at the distal region of system 100 is provided. FIG. 5A illustrates braided structure 116, e.g., a nitinol braid, in a straight tubular configuration having an initial diameter. As shown in FIGS. 5B and 5C, a proximal end region of braided structure 116 may be placed over attachment ring 117, and crimper ring 119 may then be disposed over (e.g., swagged over) the proximal end region of braided structure 116, such that the proximal end region of braided structure 116 is sandwiched between attachment ring 117 and crimper ring 119 in a contracted state having a reduced diameter from the initial diameter, which may be essentially equal to the diameter of the outer surface of fixed shaft 114. Next, as shown in FIG. 5D, the distal end region of braided structure 116 may be everted such that it folds over itself and pulled proximally relative to the proximal end region of braided structure 116 such that it extends over and surrounds the outer surface of the proximal region of braided structure 116, and forms an elongated collapsed configuration.

Figure 5E:
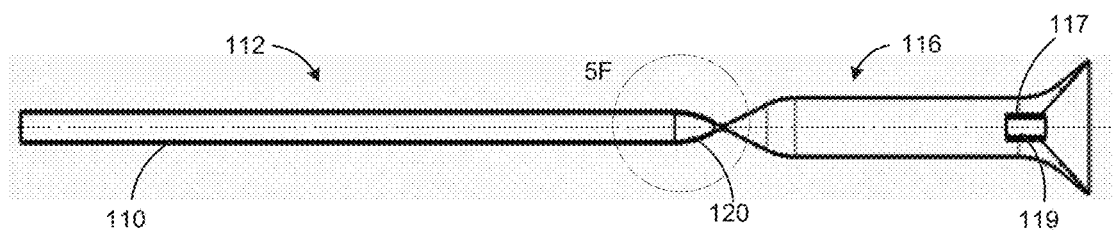
Figure 5F:
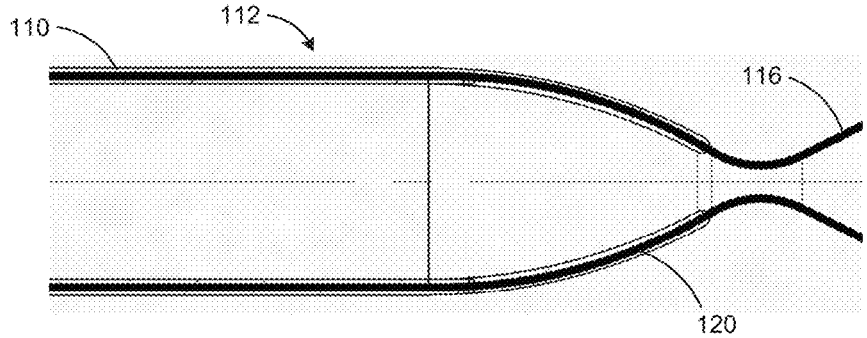

As shown in FIG. 5E, the everted distal end region of braided structure 116 may be disposed over and coupled to distal region 112 of outer sheath 110, such that the distal end region of braided structure 116 has a reduced diameter from the initial diameter, which may be essentially equal to the diameter of the outer surface of outer sheath 110. For example, the distal end region of braided portion 116 may be embedded in distal region 112 of outer sheath 110 by a reflow process with different material hardness and lubricity, as will be understood by a person having ordinary skill in the art. As shown in FIG. 5F, the distal end of distal region 112 of outer sheath 110 may be biased towards a collapsed state, to thereby form tip 120 of outer sheath 110. For example, the cylindrical extending portion of distal region 112 may be formed of a material having greater hardness than the portion of distal region 112 that forms atraumatic tip 120. Moreover, the inner layer of outer sheath 110 may comprise a lubricious material, e.g., Polytetrafluoroethylene (PTFE) or fluorinated ethylene propylene (FEP). Attachment ring 117 having the proximal end region of braided structure 116 and crimper ring 117 coupled thereto may then be coupled to distal region 113 of fixed shaft 114.

Figure 6A:
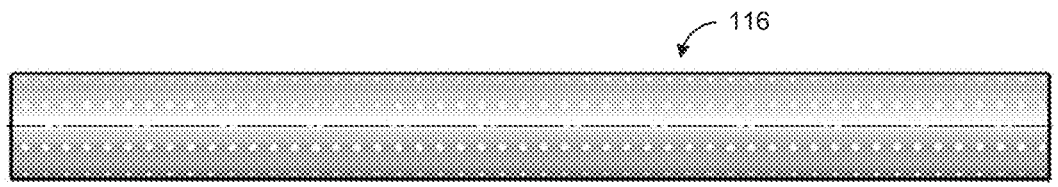
FIGS. 6A to 6E illustrate an alternative exemplary method for assembling the exemplary invertible braided structure at the distal region of the delivery system of FIG. 1 in accordance with the principles of the present disclosure.
Figure 6B:
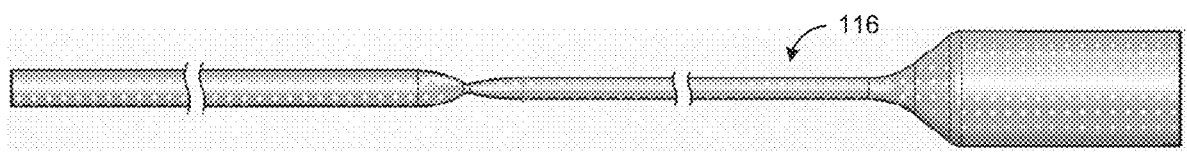
Figure 6C:
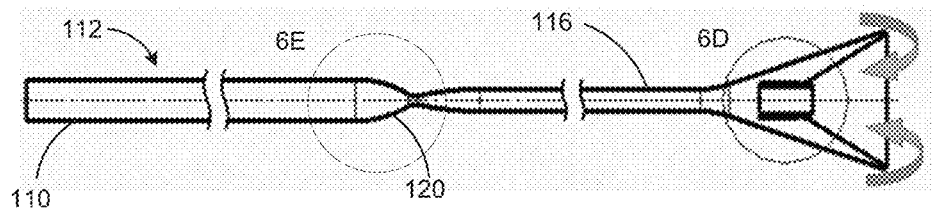
Figure 6D:
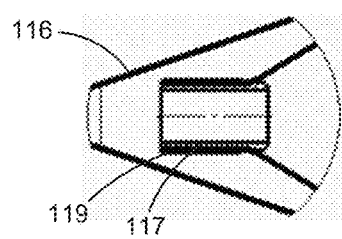

Referring now to FIGS. 6A to 6E, an exemplary method for assembling invertible braided structure 116 at the distal region of system 100 is provided. FIG. 6A illustrates braided structure 116, e.g., a nitinol braid, in a straight tubular configuration having an initial diameter. Braided structure 116 may then be elongated and placed over a heat setting mandrel having the predefined shape shown in FIG. 6B, and heat set to have the predefined shape of the heat setting mandrel. This elongation may significantly reduce the braid angle of braided structure 116, to thereby provide greater collum stiffness to braided structure 116. As shown in FIG. 6C, the distal end region of braided structure 116 may be inverted such that it folds within itself and extends in a proximal direction, and coupled to distal region 113 of fixed shaft 114, as shown in FIG. 6D. For example, the inverted distal region of braided structure 116 may be placed over attachment ring 117, and crimper ring 119 may then be disposed over (e.g., swagged over) the inverted distal end region of braided structure 116, such that the inverted distal end region of braided structure 116 is sandwiched between attachment ring 117 and crimper ring 119 in a contracted state having a reduced diameter from the initial diameter, which may be essentially equal to the diameter of the outer surface of fixed shaft 114.

Figure 6E:
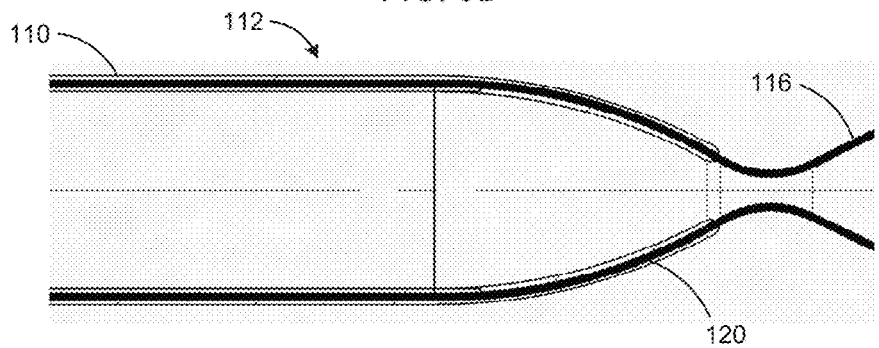

Referring again to FIG. 6C, the proximal end region of braided structure 116 may then be disposed over and coupled to distal region 112 of outer sheath 110, such that the proximal end region of braided structure 116 has a reduced diameter from the initial diameter, which may be essentially equal to the diameter of the outer surface of outer sheath 110. For example, the proximal end region of braided portion 116 may be embedded in distal region 112 of outer sheath 110 by a reflow process with different material hardness and lubricity, as will be understood by a person having ordinary skill in the art. As shown in FIG. 6E, the distal end of distal region 112 of outer sheath 110 may be biased towards a collapsed state, to thereby form tip 120 of outer sheath 110. For example, the cylindrical extending portion of distal region 112 may be formed of a material having greater hardness than the portion of distal region 112 that forms atraumatic tip 120. Moreover, the inner layer of outer sheath 110 may comprise a lubricious material, e.g., Polytetrafluoroethylene (PTFE) or fluorinated ethylene propylene (FEP). Attachment ring 117 having the distal end region of braided structure 116 and crimper ring 117 coupled thereto may then be coupled to distal region 113 of fixed shaft 114.

Referring now to FIGS. 7A and 7B, an exemplary handle of delivery system 100 for actuating deployment and delivery of occluder 200 at the atrial septum is provided. Handle 130 may include handle body 131 sized and shaped to be held and operated by a user, and may be operatively coupled to the proximal regions of outer shaft 106, inner shaft 108, and outer sheath 110, and fixedly coupled to the proximal region of fixed shaft 114. For example, handle 130 may include a plurality of sliders and knob actuators, e.g., slidable outer shaft actuator 140 operatively coupled to the proximal region of outer shaft 106, slidable outer sheath actuator 160 fixedly coupled to the proximal region of outer sheath 110, rotatable outer shaft actuator 170 configured to be operatively coupled to the proximal region of outer shaft 106 and fixedly coupled to the proximal region of fixed shaft 114, and rotatable inner shaft actuator 180 fixedly coupled to the proximal region of inner shaft 108.

As shown in FIG. 7A, handle body 131 may include one or more tracks, e.g., track 132 configured to slidably receive slidable outer shaft actuator 140 and track 134 configured to slidably receive outer sheath actuator 160. Accordingly, slidable outer shaft actuator 140 may be moved relative to handle body 131 along track 132 to thereby move outer shaft 106 relative to inner shaft 108, fixed shaft 114, and outer sheath 110, and outer sheath actuator 160 may be moved relative to handle body 131 along track 134 to thereby move outer sheath 110 relative to inner shaft 108, outer shaft 110, and fixed shaft 114. As shown in FIG. 7B, slidable outer shaft actuator 140, slidable outer sheath actuator 160, rotatable outer shaft actuator 170, and rotatable inner shaft actuator 180 may be arranged on handle body 131, such that outer shaft 106 is slidably disposed over inner shaft 108 and within fixed shaft 114, and outer sheath 110 is slidably disposed over fixed shaft 114. Moreover, the axial position of rotatable inner shaft actuator 180, and accordingly inner shaft 108, may be fixed relative to handle body 131, and the axial position of rotatable outer shaft actuator 170, and accordingly fixed shaft 114, may be fixed relative to handle body 131.

Figure 8A:
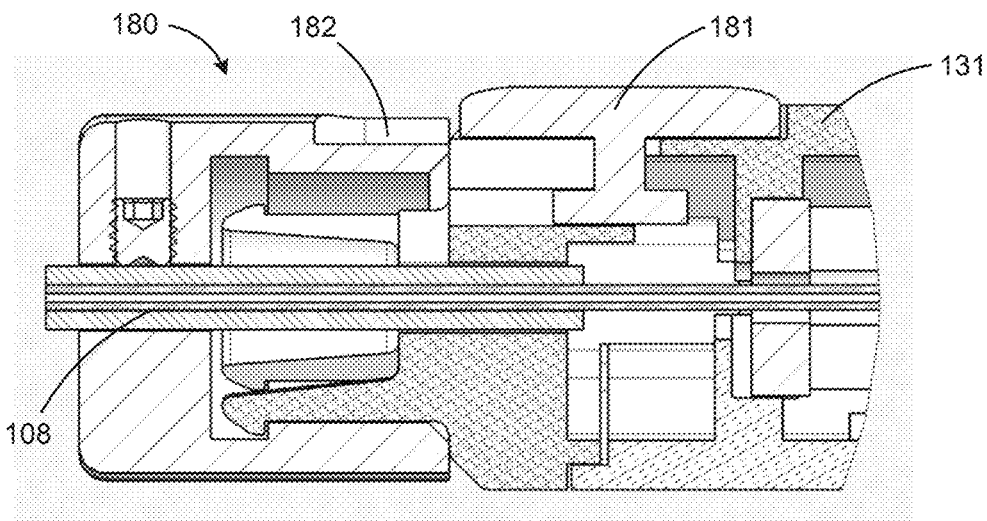
FIGS. 8A to 8D illustrate an exemplary inner shaft actuator of the handle of FIGS. 7A and 7B.
Figure 8B:
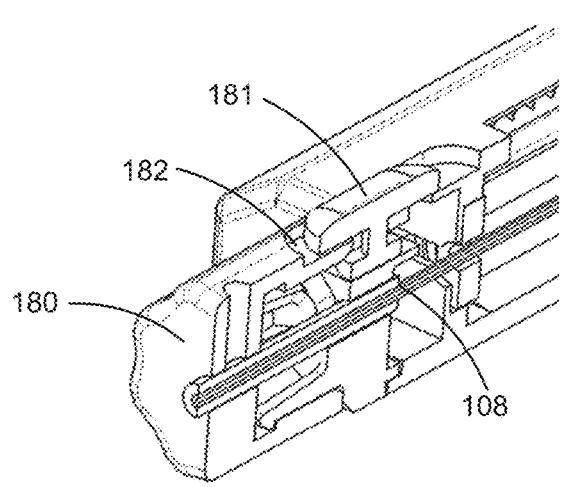
Figure 8C:
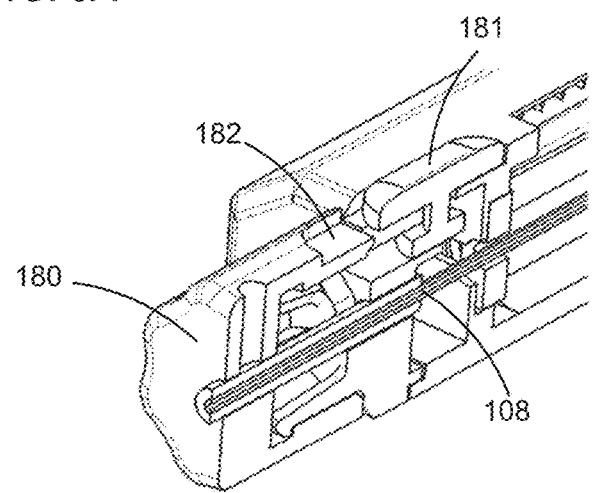
Figure 8D:
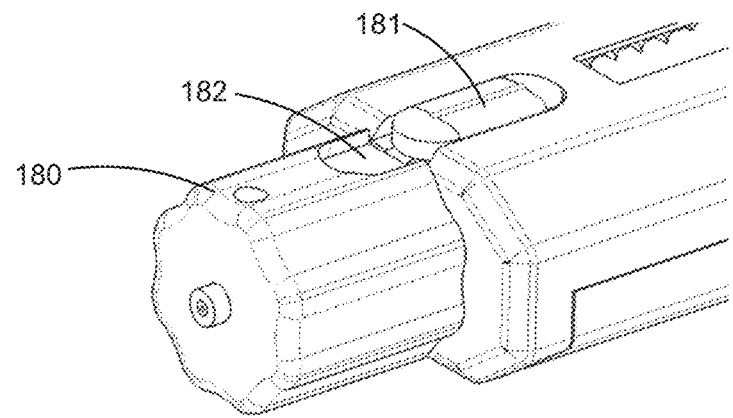

Referring now to FIGS. 8A to 8D, an exemplary inner shaft actuator of handle 130. As shown in FIG. 8A, inner shaft actuator 180, e.g., a rotatable knob, may be fixedly coupled to the proximal region of inner shaft 108, and rotatably coupled to handle body 131, e.g., at the proximal end of handle body 131. Accordingly, rotation of inner shaft actuator 180 causes rotation of inner shaft 108 relative to the other components of system 100, e.g., for coupling/decoupling inner shaft 108 and distal end 205 of occluder 200 via threaded surfaces 109, 213. Inner shaft actuator 180 may include a locking mechanism, e.g., slidable latch 181 and seat 182 disposed on an outer surface of inner shaft actuator 180, to permit selective actuation of inner shaft actuator 180 and prevent inadvertent actuation of inner shaft actuator 180. FIG. 8B illustrates latch 181 in a locked position, e.g., disposed at least partially within seat 182, where rotation of inner shaft actuator 180 is inhibited, and FIGS. 8C and 8D illustrate latch 181 in an unlocked position, e.g., disengaged with seat 182, where actuation of inner shaft actuator 180 is permitted.

Figure 9A:
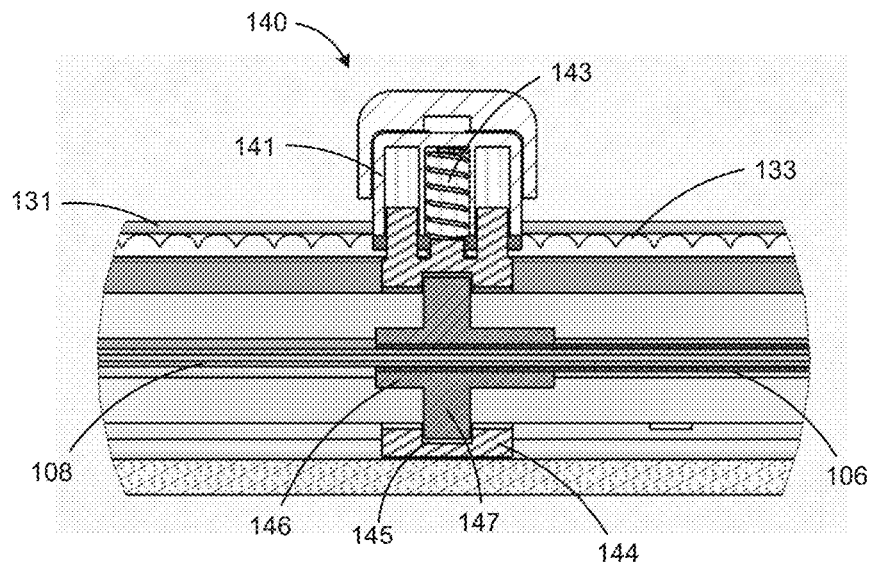
Figure 9B:
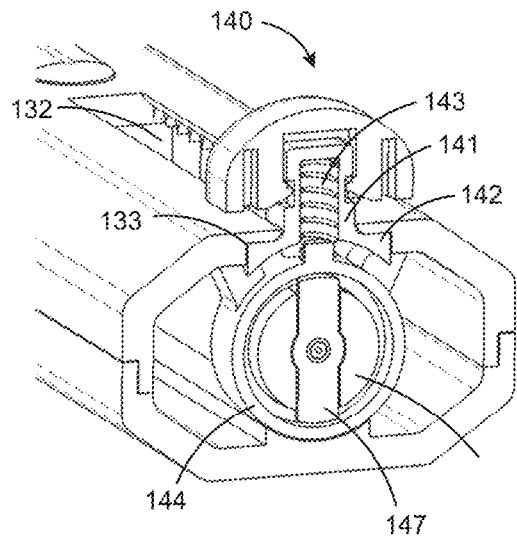
Figure 9C:
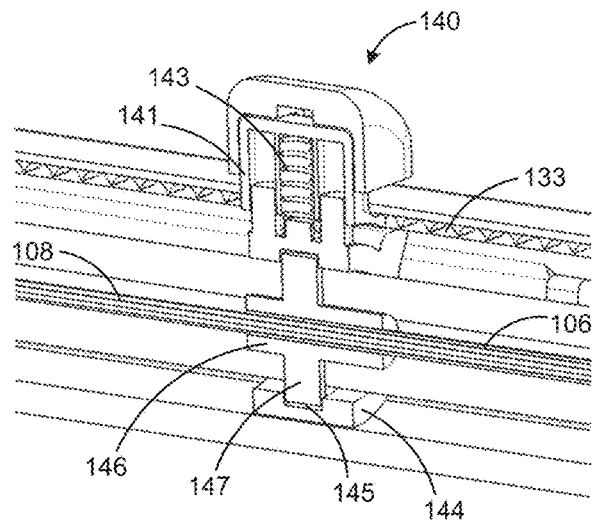

Referring now to FIGS. 9A to 9F, an exemplary slidable outer shaft actuator of handle 130 is provided. Outer shaft actuator 140 may be slidably coupled to handle body 131 and axially fixed to the proximal region of outer shaft 106, e.g., via connector 146, such that, upon actuation, outer shaft actuator 140 may be configured to be selectively moved along track 132 of handle body 131, to thereby move outer shaft 106 axially relative to handle body 131. As shown in FIGS. 9A to 9C, outer shaft actuator 140 may include pusher 141, e.g., a press button, comprising locking pin 142 sized and shaped to be releasably engaged with a groove of plurality of indexing grooves 133 disposed axially along an inner surface of handle body 131, e.g., at least along track 132, when pusher 141 is in an unactuated state. For example, pusher 141 may be coupled to compression spring 143, such that pusher 141 is biased towards the unactuated state, where locking pin 142 of pusher 141 is engaged with a groove of plurality of indexing grooves 133, thereby locking the axial position of outer shaft actuator 140, and accordingly outer shaft 106, relative to handle body 131 at a predefined position.

Upon actuation of pusher 141, e.g., by pushing pusher 141, and accordingly locking pin 142, downward towards handle body 131, locking pin 142 disengages from the groove, thereby permitting axial movement of outer shaft actuator 140 relative to handle body 131 along track 132 when pusher 141 is in its actuated state. When outer shaft actuator 140 is at the target location relative to handle body 131, pusher 141 may be released such that compression spring 143 causes pusher 141 to return to its unactuated state, such that locking pin 142 engages with a groove of plurality of indexing grooves 133 above/immediately adjacent to locking pin 142 to thereby lock the axial position of outer shaft actuator 140, and accordingly outer shaft 106, relative to handle body 131.

Moreover, outer shaft actuator 140 may be rotatably coupled to the proximal region of outer shaft 106, to thereby permit rotational movement of outer shaft 106 relative to handle body 131 via rotatable outer shaft actuator 170, as described in further detail below with regard to FIGS. 10A to 10F. For example, as shown in FIG. 9E, the proximal region of outer shaft 106 may be fixedly coupled to connector 146 having one or more pins 147 extending radially outward therefrom, and as shown in FIG. 9F, outer shaft actuator 140 may include frame 144 having internal track 145 extending circumferentially along the inner surface of frame 145, sized and shaped to slidably receive pins 147 therein. As will be understood by a person having ordinary skill in the art, while FIG. 9E shows connector 146 having two pins 147 extending radially outward therefrom, connector 146 may have less than or more than two pins extending radially outward therefrom, sized and shaped to slidably engage with track 145 of frame 144. Track 145 may extending along a plane that is perpendicular to the longitudinal axis of outer shaft 106. Moreover, the width of track 145 may correspond with the width/diameter of pins 147, such that the axial position of connector 146 is essentially fixed relative to frame 144, and accordingly, outer shaft actuator 140, while pins 147 are free to slide along track 145, to thereby permit rotation of connector 146, and accordingly, outer shaft 106, relative to frame 144.

Figure 10A:
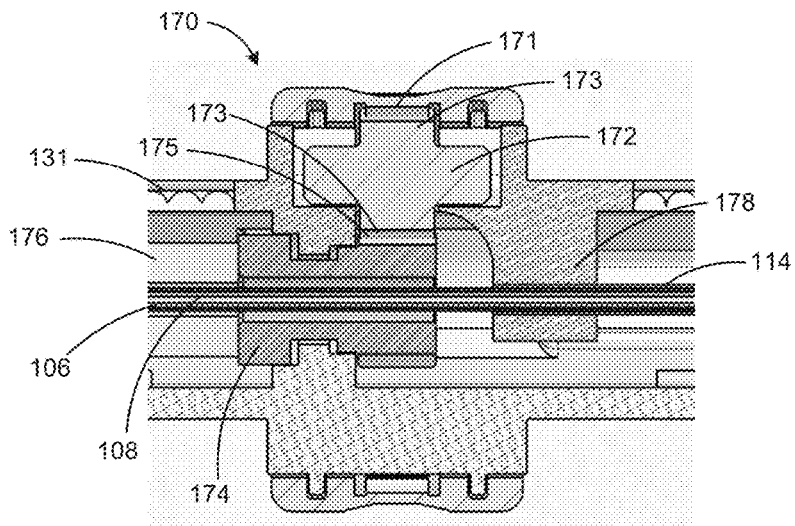
Figures 10B, 10C:
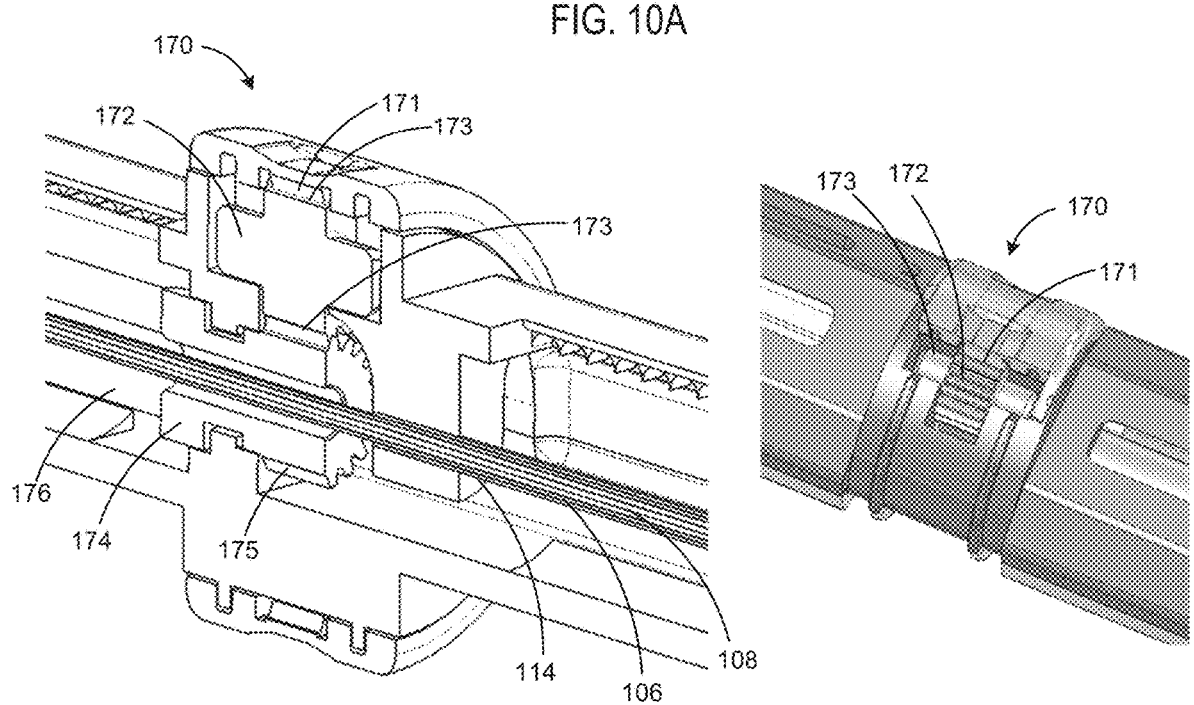

Referring now to FIGS. 10A to 10F, an exemplary rotatable outer shaft actuator of handle 130. As shown in FIGS. 10A and 10B, outer shaft actuator 170 may include connector 178 axially fixed to handle body 131, and fixedly coupled to the proximal region of fixed shaft 114, such that fixed shaft 114 is axially fixed relative to handle body 131. Outer shaft actuator 170 may be axially fixed to and rotatably coupled to handle body 131, such that outer shaft actuator 170 may be rotated relative to handle body 131. For example, as shown in FIGS. 10A to 10F, an inner surface of the rotatable interface of outer shaft actuator 170, e.g., a ring gear, may include geared surface 171 extending circumferentially along the inner surface of outer shaft actuator 170, e.g., along a plane that is perpendicular to the longitudinal axis of handle body 131. Moreover, outer shaft actuator 170 may include sun gear 174 having geared surface 175 extending circumferentially around the outer surface of sun gear 174, and a lumen sized and shaped for slidably receiving outer shaft 106 therethrough. The lumen of sun gear 174 may be coaxial with the longitudinal axis of outer shaft 106, and sun gear 174 may be axially fixed relative to handle body 131.

In addition, outer shaft actuator 170 may include planet gear 172 having geared surface 173 extending circumferentially around the outer surface of planet gear 172, wherein geared surface 173 is configured to rotatably engage with geared surfaces 171, 175. Planet gear 172 may be axially fixed relative to handle body 131, and disposed between geared surface 171 of outer shaft actuator 170 and geared surface 175 of sun gear 174, such that rotation of outer shaft actuator 170 causes rotation of planet gear 172 via geared surfaces 171, 173, e.g., in the same direction of rotation of outer shaft actuator 170, which causes rotation of sun gear 174 via geared surfaces 173, 175, e.g., in an opposite direction of rotation of outer shaft actuator 170 and planet gear 172. As will be understood by a person having ordinary skill in the art, the size and spacing of the gear teeth of geared surfaces 171, 173, 175 may be selected to provide a 1:1 angular rotation of sun gear 174 responsive to rotation of outer shaft actuator 170, or alternatively, the size and spacing of the gear teeth of geared surfaces 171, 173, 175 may be selected to provide a larger (e.g., amplified) or smaller (e.g., reduced) angular rotation of sun gear 174 responsive to rotation of outer shaft actuator 170.

Moreover, as shown in FIGS. 10C to 10F, outer shaft actuator 170 may include transmission shaft 176 extending proximally from sun gear 174. Transmission shaft 176 may have a lumen sized and shaped to slidably receive outer shaft 106 therethrough. The diameter of the outer surface of transmission shaft 176 may correspond with the inner diameter of frame 144 of outer shaft actuator 140, such that transmission shaft 176 may be rotated within the inner lumen of frame 144. In addition, transmission shaft 176 may include track 177 extending in a radial direction between the lumen and outer surface of transmission shaft 176, and in a longitudinal direction along the length of transmission shaft 176. The width of track 177 may correspond with the width/diameter of pins 147 of connector 146 of outer shaft actuator 140, such that pins 147 may extend completely through track 177 to slidably engage with track 145 of frame 144. Accordingly, upon rotation of sun gear 174 (via rotation of outer shaft actuator 170 and planet gear 174), and accordingly, transmission shaft 176 fixedly coupled thereto, contact between the walls of track 177 and pins 147 causes pins 147 to slide along track 145 of frame 144, thereby rotating connector 176, and accordingly outer shaft 106 fixedly coupled thereto. In some embodiments, outer shaft actuator 170 may include a locking mechanism that must be actuated to permit rotation of outer shaft actuator 170, to thereby prevent inadvertent actuation of outer shaft actuator 170.

Figure 11A:
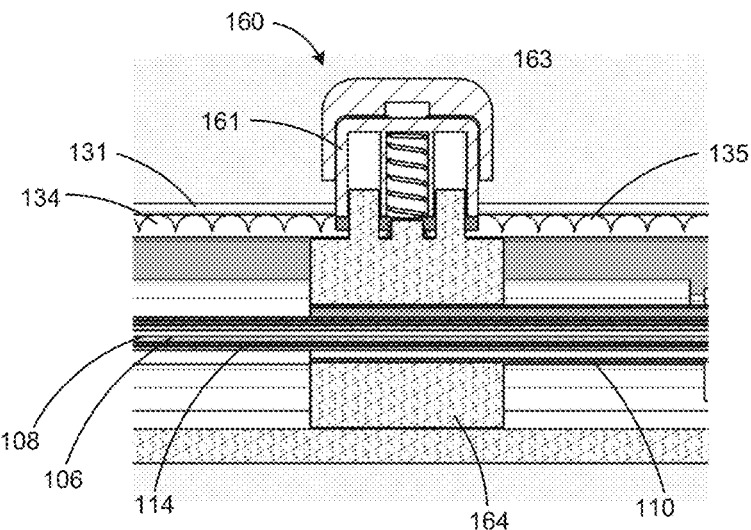
FIGS. 11A to 11C illustrate an exemplary outer sheath actuator of the handle of FIGS. 7A and 7B.
Figure 11B:
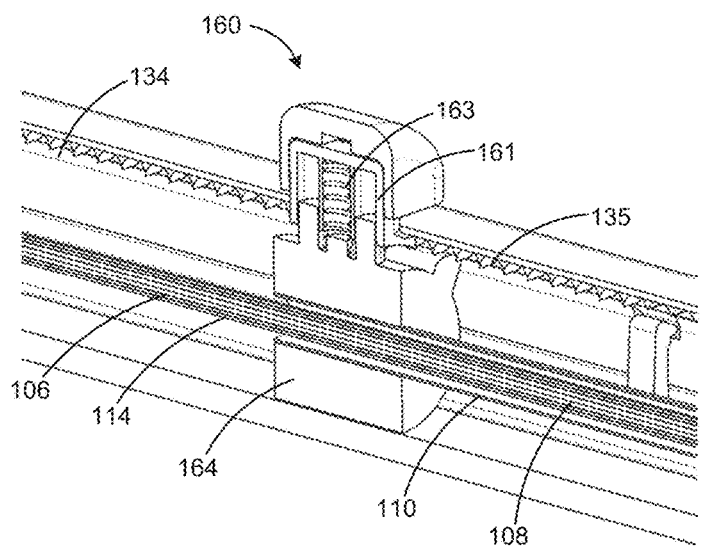
Figure 11C:
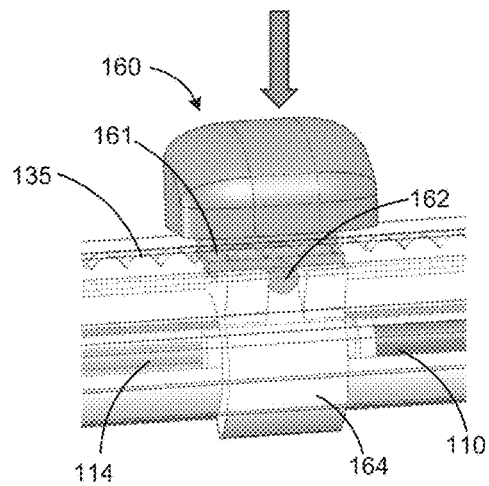

Referring now to FIGS. 11A to 11C, an exemplary outer sheath actuator of handle 130 is provided. Outer sheath actuator 160 may be slidably coupled to handle body 131 and fixedly coupled to the proximal region of outer sheath 110 via connector 164, such that, upon actuation, outer sheath actuator 160 may be configured to be selectively moved along track 134 of handle body 131, to thereby move outer sheath 110 axially relative to handle body 131. Connector 164 may have a lumen sized and shaped to slidably receive fixed shaft 114 therethrough. Accordingly, the lumen of connector 164 may be coaxial with the longitudinal axis of fixed shaft 114 and outer sheath 110. As shown in FIGS. 11A to 11C, outer sheath actuator 160 may include pusher 161, e.g., a press button, comprising locking pin 162 sized and shaped to be releasably engaged with a groove of plurality of indexing grooves 135 disposed axially along an inner surface of handle body 131, e.g., at least along track 134, when pusher 161 is in an unactuated state. For example, pusher 161 may be coupled to compression spring 163, such that pusher 161 is biased towards the unactuated state, where locking pin 162 of pusher 161 is engaged with a groove of plurality of indexing grooves 135, thereby locking the axial position of outer sheath actuator 160, and accordingly outer sheath 110, relative to handle body 131 at a predefined position.

Upon actuation of pusher 161, e.g., by pushing pusher 161, and accordingly locking pin 162, downward towards handle body 131, locking pin 162 disengages from the groove, thereby permitting axial movement of outer sheath actuator 160 relative to handle body 131 along track 134 when pusher 161 is in its actuated state. When outer sheath actuator 160 is at the target location relative to handle body 131, pusher 161 may be released such that compression spring 163 causes pusher 161 to return to its unactuated state, such that locking pin 162 engages with a groove of plurality of indexing grooves 135 above/immediately adjacent to locking pin 162 to thereby lock the axial position of outer sheath actuator 160, and accordingly outer sheath 110, relative to handle body 131.

Figure 12:
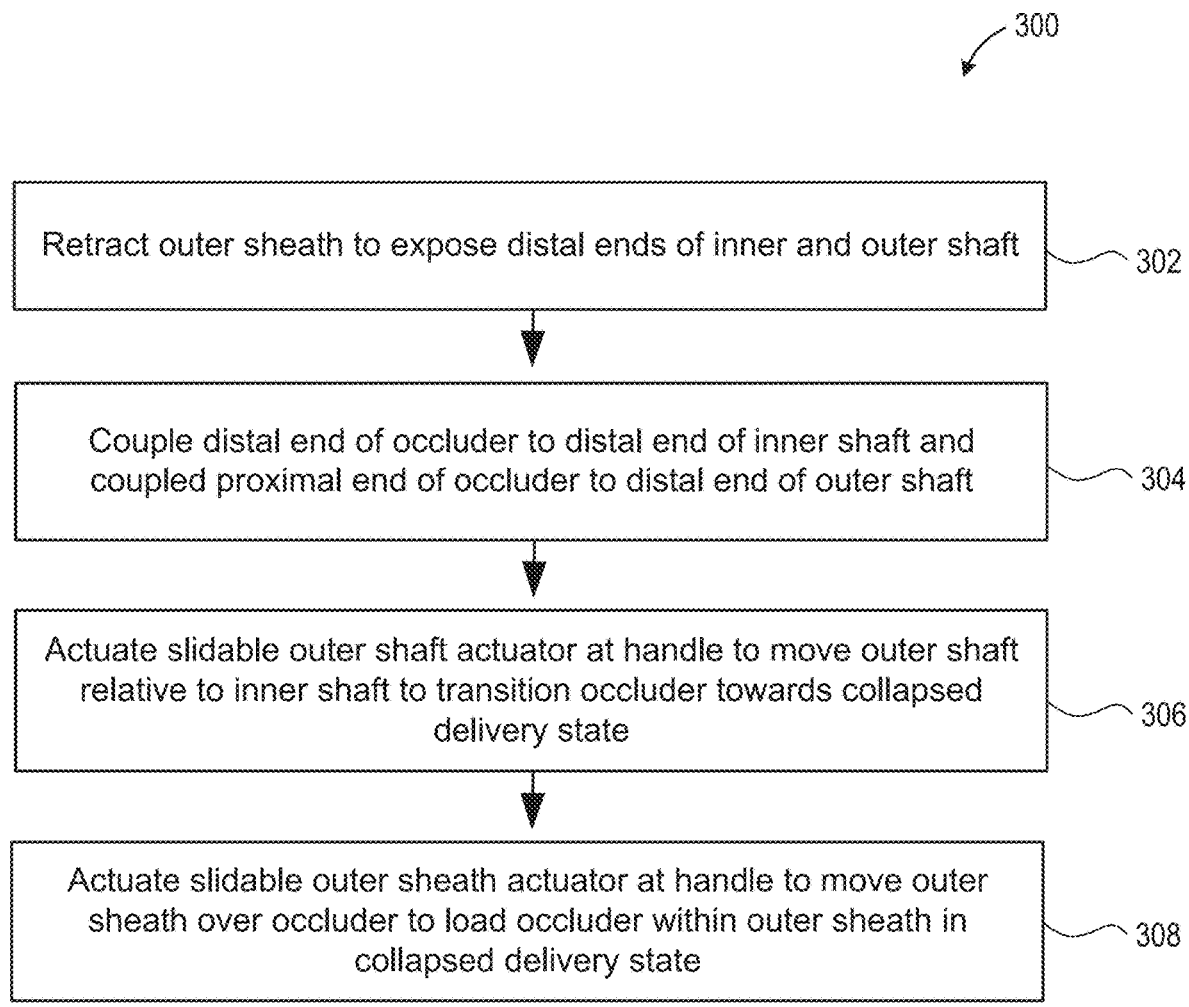
FIG. 12 is a flow chart of exemplary method steps for loading the occluder device of FIG. 2A within the delivery system of FIG. 1 in accordance with the principles of the present disclosure.
Figure 13A:
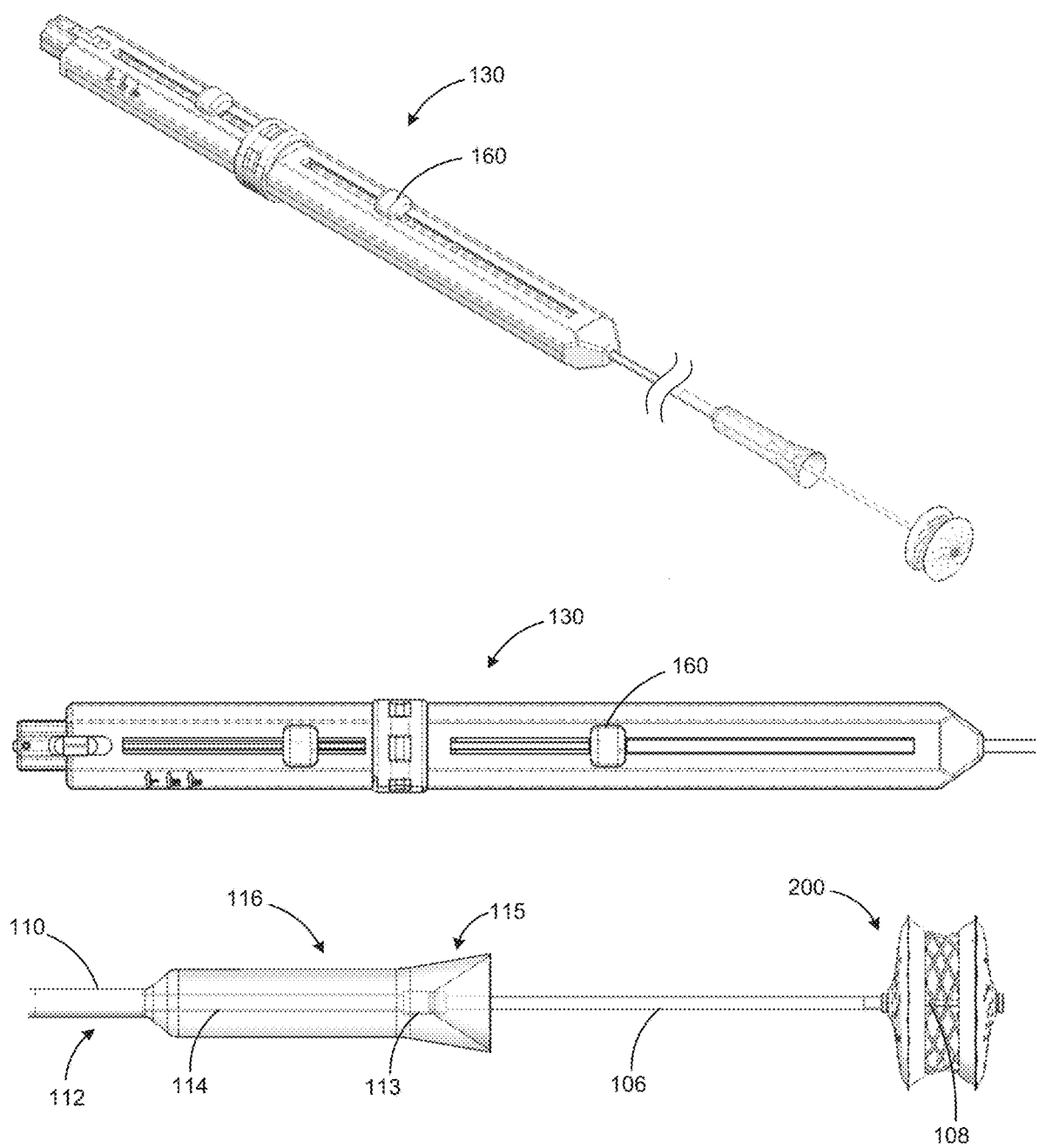
FIGS. 13A to 13E illustrate an exemplary method for loading the occluder device of FIG. 2A within the outer sheath in accordance with the principles of the present disclosure.

Referring now to FIG. 12, exemplary method 300 for loading occluder 200 into outer sheath 110 is provided. Some of the steps of method 300 may be further elaborated by referring to FIGS. 13A to 13E. At step 302, outer sheath 110 may be retracted proximally relative to outer shaft 106, inner shaft 108, and fixed shaft 114 via outer shaft actuator 160, such that distal region 112 of outer sheath 110 is positioned proximal to distal region 113 of fixed shaft 114 and braided structure 116 is in a rest configuration, e.g., the elongated collapsed delivery configuration, to thereby expose the distal regions of outer shaft 106 and inner shaft 108, as shown in FIG. 13A. At step 304, proximal end 203 of occluder 200 may be removably coupled to the distal region of outer shaft 106 via threaded surfaces 107, 209, and distal end 205 may be removably coupled to the distal region of inner shaft 108 slidably disposed within and extending distally from outer shaft 106 via threaded surfaces 109, 213, as shown in FIG. 13A.

Figure 13B:
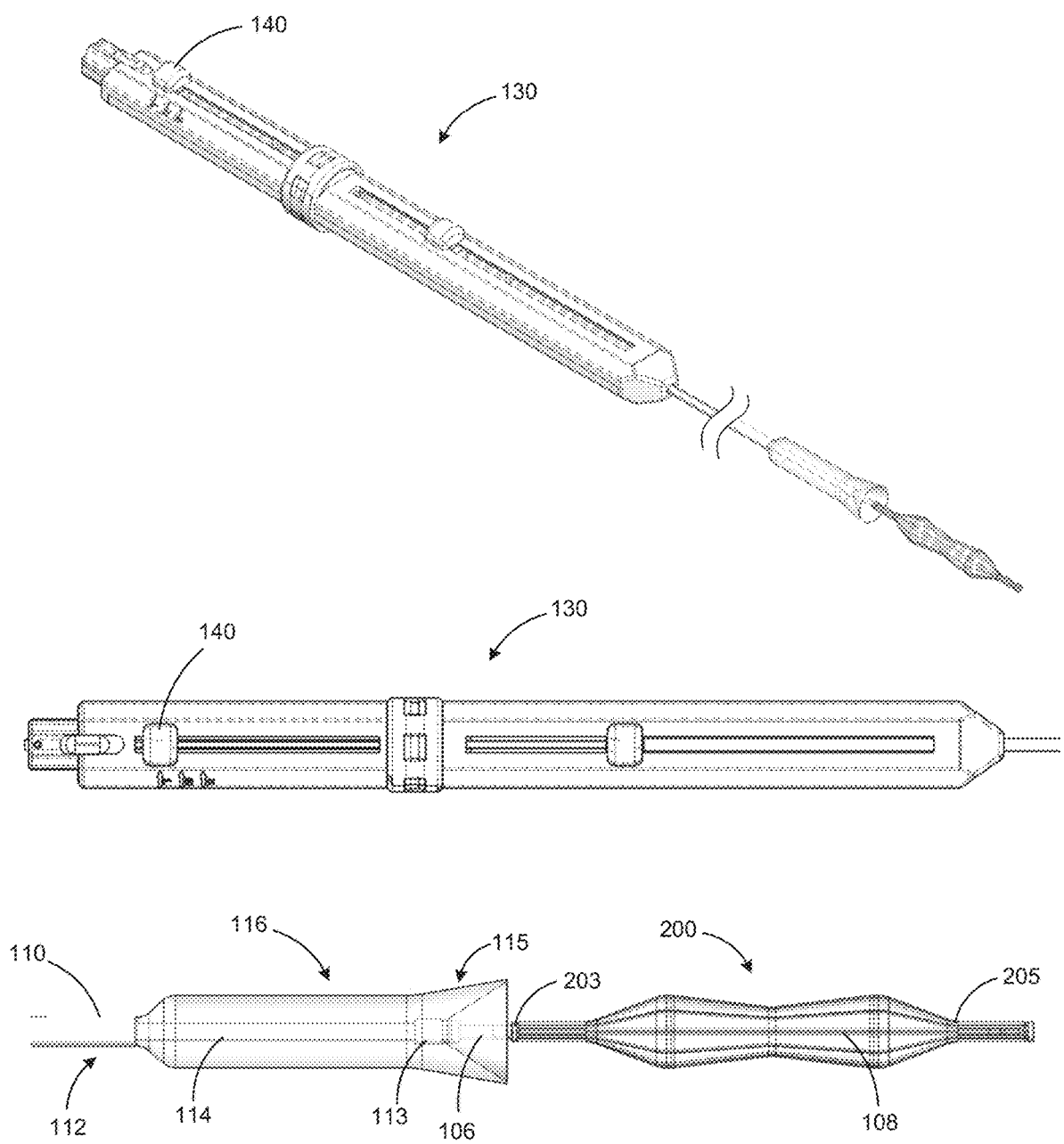
Figure 13C:
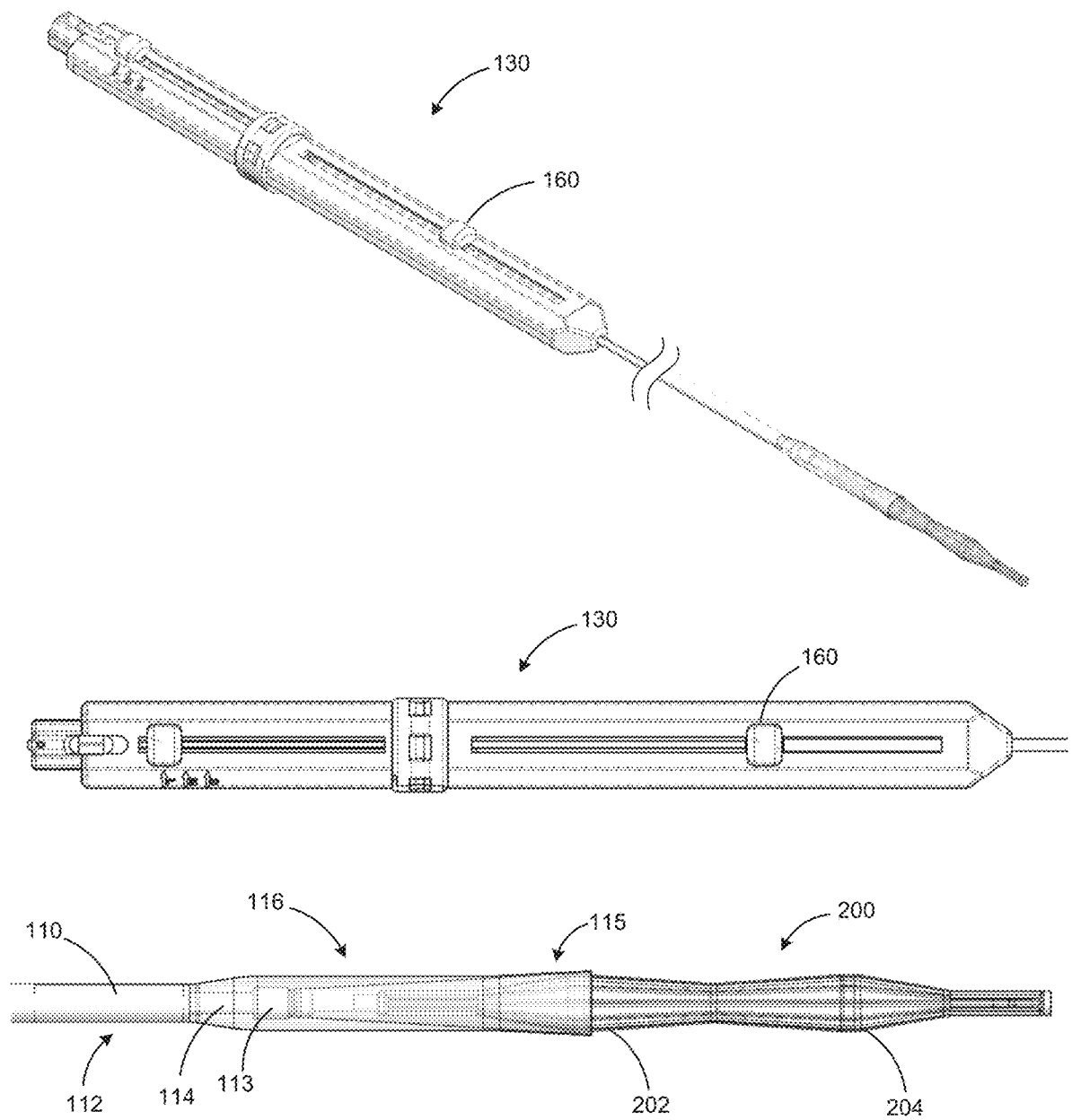

At step 306, outer shaft 106 may be retracted proximally relative to inner shaft 108 via outer shaft actuator 140, such that the distal region outer shaft 106, and accordingly, proximal end 203 of occluder 200, is moved proximally relative to the distal region of inner shaft 108, and accordingly, distal end 205 of occluder 200, as shown in FIG. 13B. As shown in FIG. 13B, the distal regions of outer shaft 106 and inner shaft 108, and accordingly, proximal end 203 and distal end 205 of occluder 200, may be spaced apart such that occluder 200 in is a semi-collapsed delivery state with an elongated configuration along inner shaft 108, to facilitate introduction of occluder 200 within outer sheath 110. At step 308, outer sheath 110 may be advanced distally relative to fixed shaft 114, outer shaft 106, and inner shaft 108 via outer sheath actuator 160, such that braided structure 116 folds over itself, and contacts and envelops occluder 200 in its collapsed delivery state, as shown in FIG. 13C.

Figure 13D:
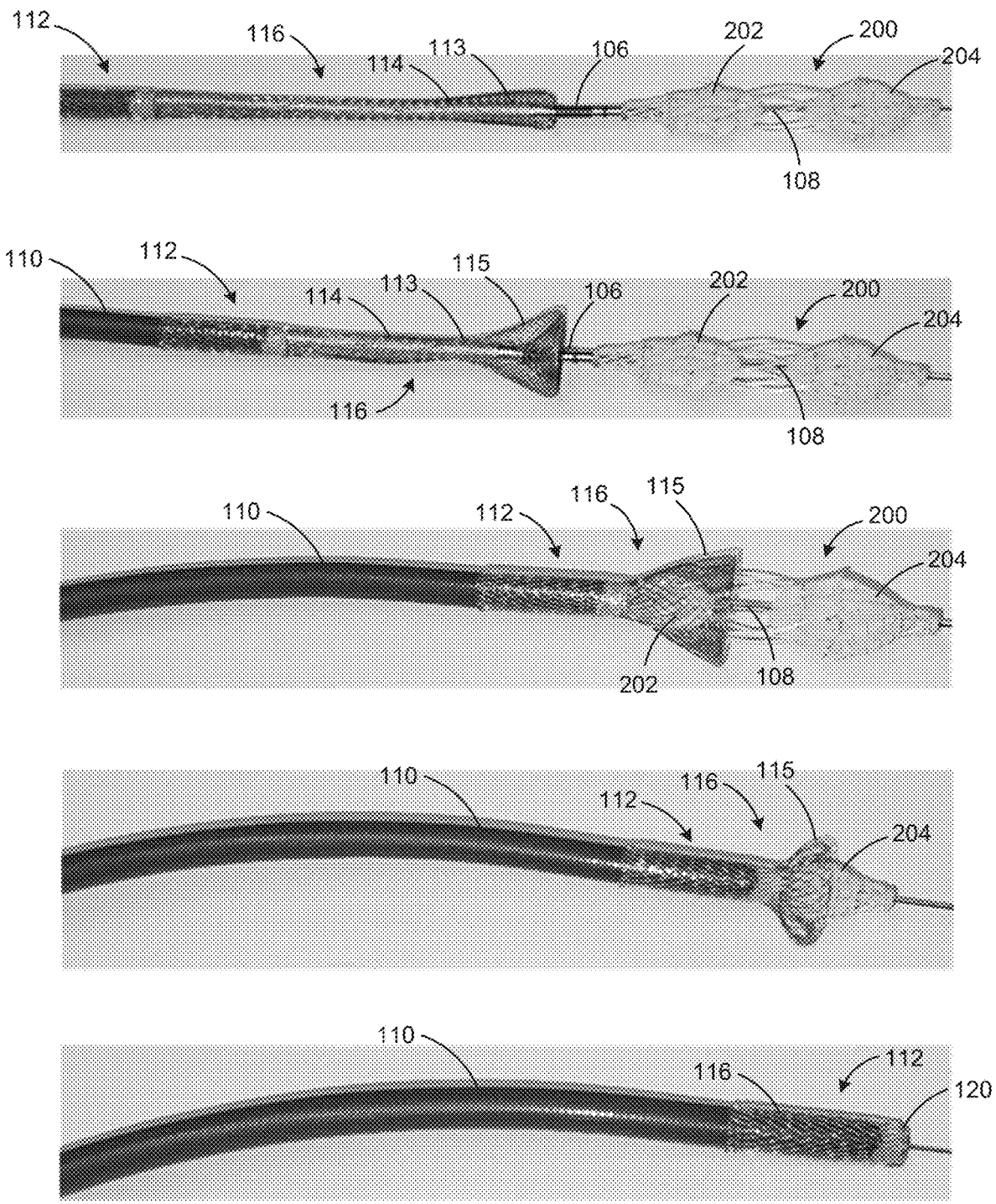
Figure 13E:
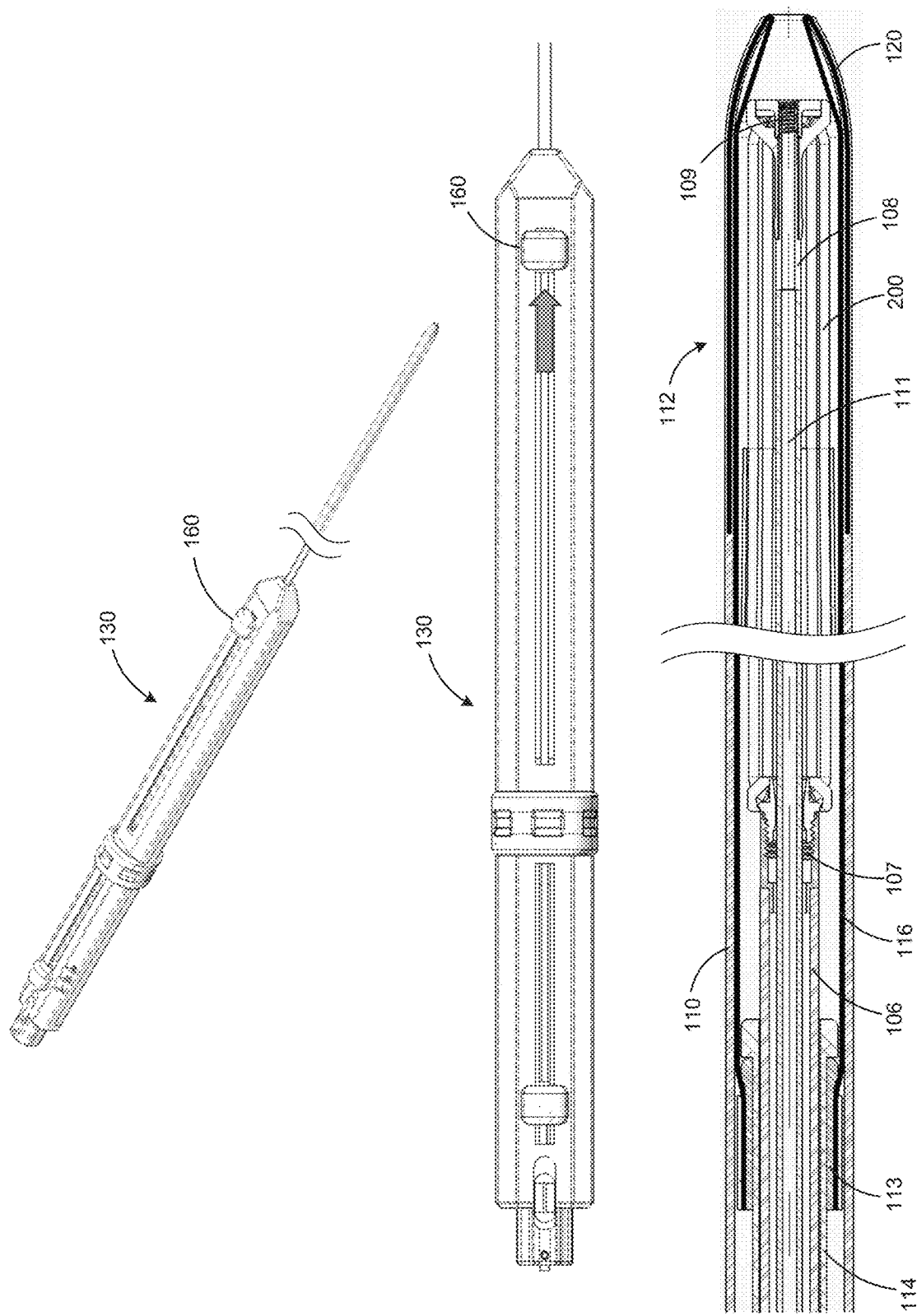

FIG. 13D illustrates the distal region of system 100 as outer sheath 110 is advanced distally relative to fixed sheath 114 to thereby wrap braided structure 116 over occluder 200 in its collapsed delivery state. As described above, as force is applied to braided structure 116 (e.g., via distal movement of outer sheath 110), the distal portion of braided structure 116 may expand radially outward to form cone shaped portion 115, which may be sized and shaped to facilitate loading of occluder 200 through the inverted portion of braided structure 116. For example, cone shaped portion 115 may contact and envelop (e.g., roll over) proximal portion 202 of occluder 200 as outer sheath 110 is moved distally relative to fixed sheath 114, followed by distal portion 204 of occluder 200, as shown in FIG. 13D. As shown in FIG. 13E, outer sheath 110 may be advanced distally relative to fixed shaft 114 until braided structure 116 is in its collapsed delivery configuration with occluder 200 completely disposed therein in its collapsed delivery state, and the distal end of distal region 112 of outer sheath 110 forms atraumatic tip 120 to facilitate navigation of outer sheath 110 through the patient's body to the atrial septum.

In addition, in the collapsed delivery configuration, tip 120 may define a lumen sized and shaped to receive a guidewire therethrough. As occluder 200 is passed into the lumen of distal region 112 of outer sheath 110, the inner surface of braided structure 116 and/or the inner wall of outer sheath 110 may apply a force against occluder 200 to thereby facilitate further radial contraction of occluder 200 to the fully collapsed delivery state within outer sheath 110, as shown in FIG. 13E. With occluder 200 disposed in its collapsed delivery state within outer sheath 110 in its collapsed delivery configuration, system 100 may then be used to deliver and deploy occluder 200 at an atrial septum of a patient's heart, e.g., using the method steps described above with regard to FIG. 14. Moreover, method 300 similarly may be used to load occluder 200 within the outer sheath of delivery system 400, as described in further detail below with regard to FIGS. 18A to 18C.

Figure 14:
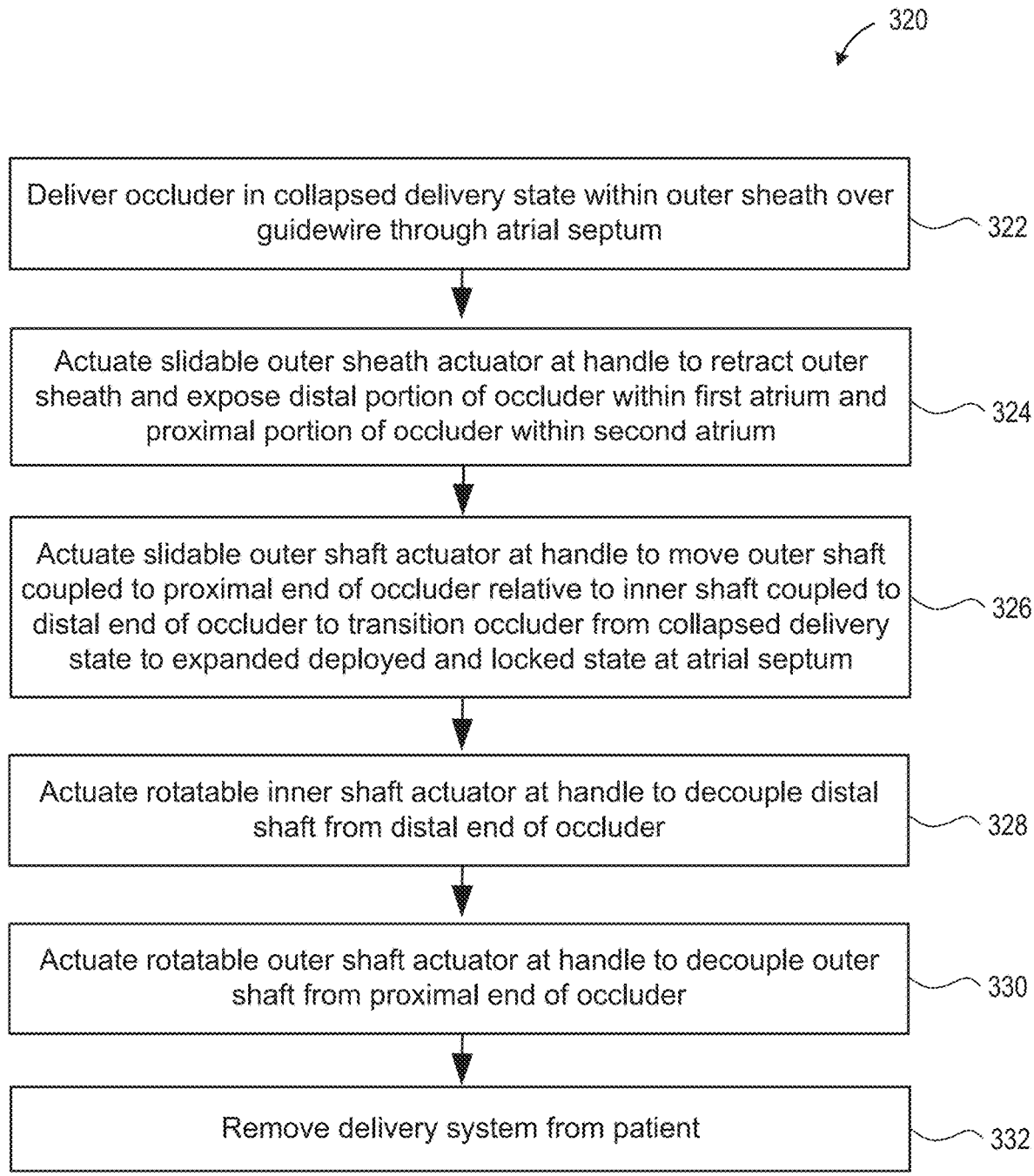
FIG. 14 is a flow chart of exemplary method steps for delivering the occluder device of FIG. 2A using the delivery system of FIG. 1 in accordance with the principles of the present disclosure.
Figure 15A:
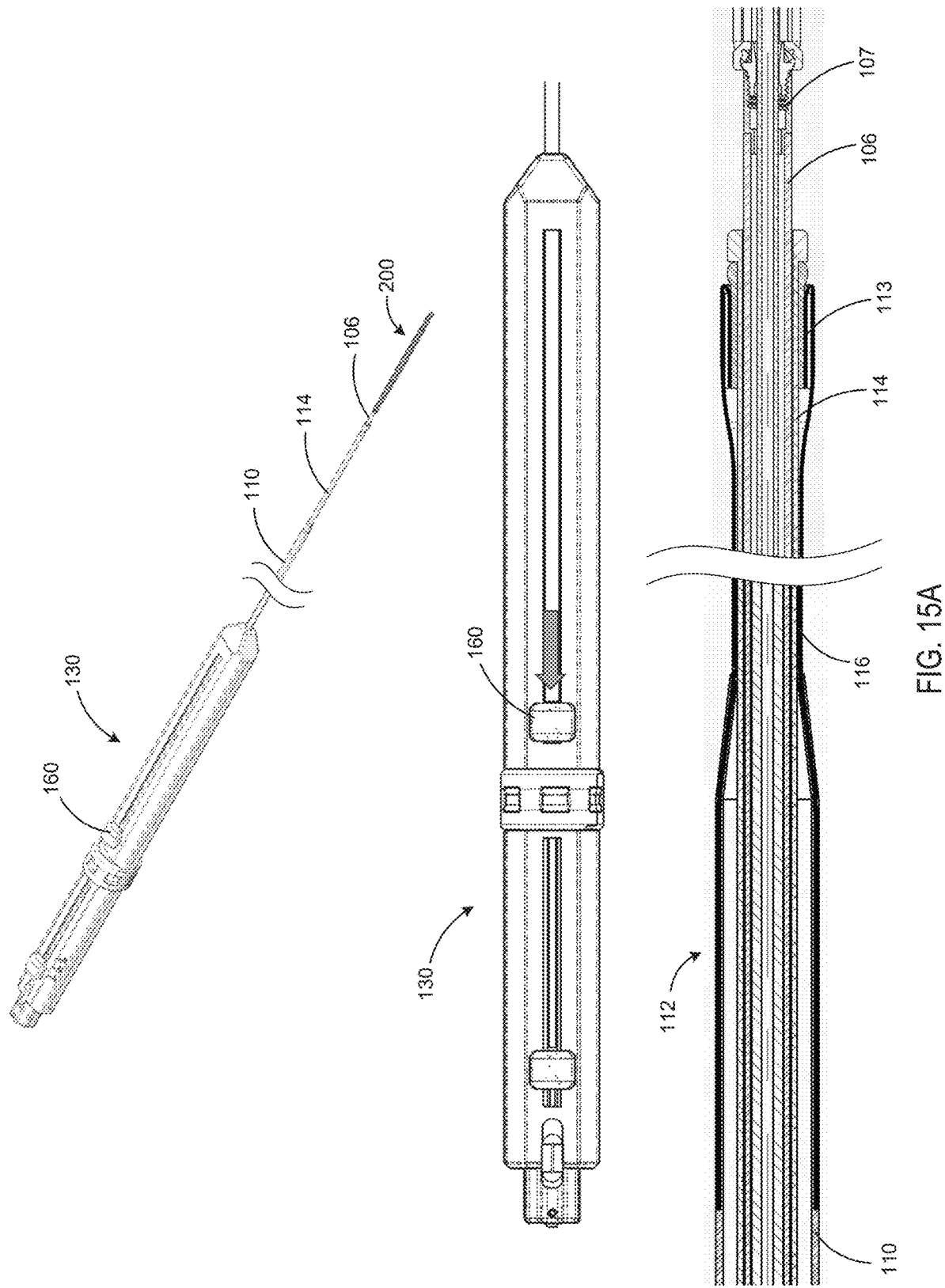
FIGS. 15A to 15F illustrate exemplary method steps for delivering the occluder device of FIG. 2A using the delivery system of FIG. 1 in accordance with the principles of the present disclosure.

Referring now to FIG. 14, exemplary method 320 for delivering occluder 200 to an atrial septum of a patient having an atrial septal defect using delivery system 100 is provided. Some of the steps of method 320 may be further elaborated by referring to FIGS. 15A to 15F. Initially, a guidewire may be advanced through the patient's body to the atrial septum, e.g., through the atrial septal defect. At step 322, outer sheath 110 having occluder 200 disposed therein may be advanced over the guidewire (e.g., via guidewire lumen 111 of inner shaft 108) to the patient's atrial septum. Distal region 112 may be advanced across the atrial septal defect to thereby align occluder 200 disposed within outer sheath 410 with the atrial septum, such that distal portion 204 of occluder 200 is disposed within a first atrium, e.g., the left atrium, and proximal portion 202 of occluder 200 is disposed within a second atrium, e.g., the right atrium. At step 324, outer sheath actuator 160 may be actuated, e.g., moved proximally relative to handle body 131, to retract outer sheath 110 proximally relative to outer shaft 106, inner shaft 108, and fixed shaft 114, and accordingly occluder 200, to thereby transition braided structure 116 to its elongated collapsed configuration and expose occluder 200 beyond the distal end of distal region 112 of outer sheath 110 in its collapsed (or semi-collapsed) delivery state, as shown in FIG. 15A. For example, upon exposure from outer sheath 110, occluder 200 may at least partially self-expand from the fully collapsed delivery state within outer sheath 110 to a semi-collapsed delivery state.

Figure 15B:
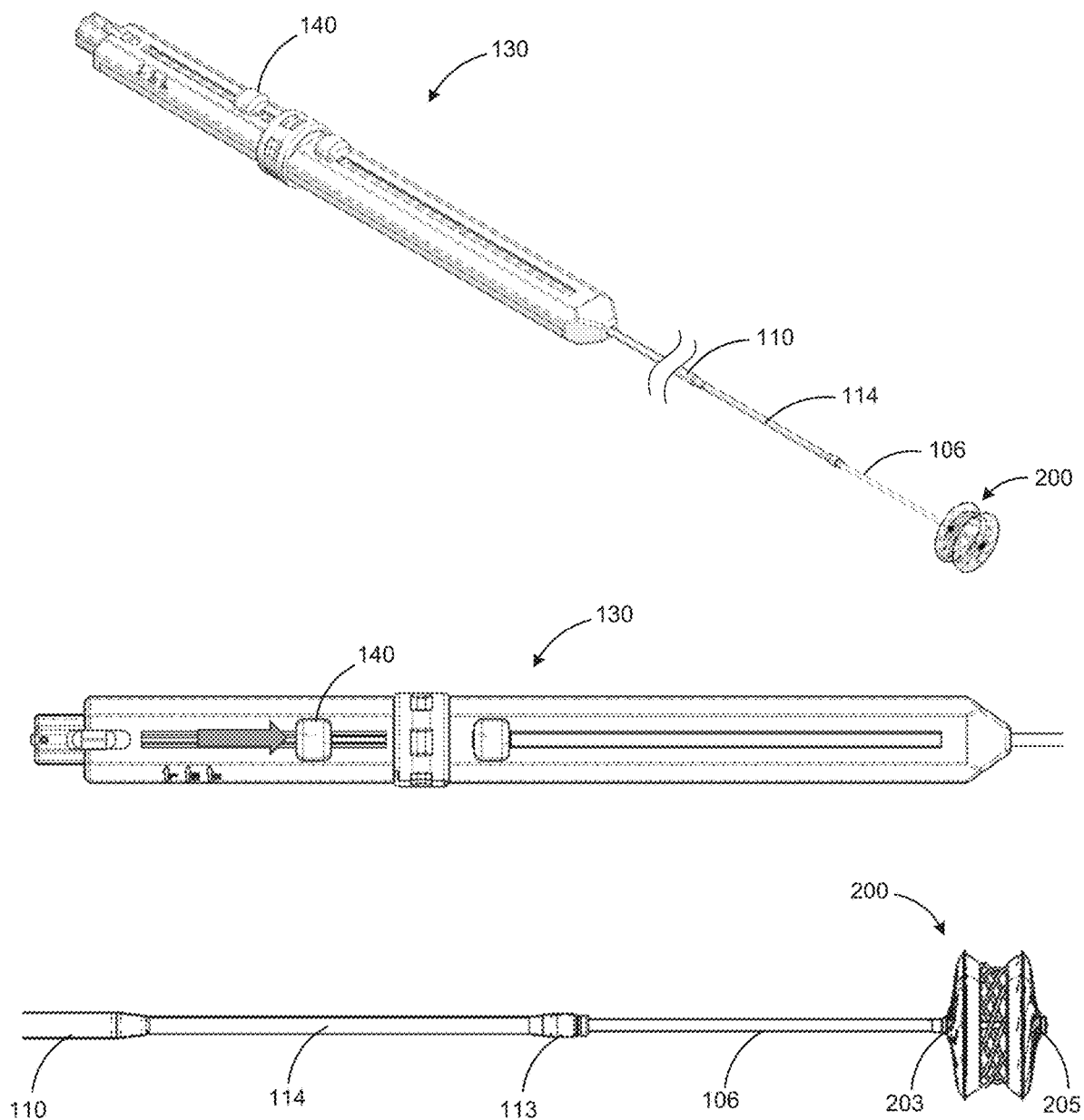

At step 326, slidable outer shaft actuator 140 may be actuated, e.g., moved distally relative to handle body 131 towards rotatable outer shaft actuator 170, to move the distal region of outer shaft 106, and accordingly proximal end 203 of occluder 200 coupled thereto via threaded surface 107 and threaded surface 209, distally towards the distal region of inner shaft 108, and accordingly distal end 205 of occluder 200 coupled thereto via threaded surface 109 and threaded surface 213, to thereby transition proximal portion 202 of occluder 200 towards its expanded deployed state within the right atrium and transition distal portion 204 of occluder 200 towards its expanded deployed state within the left atrium, as shown in FIG. 15B. As described above, as proximal portion 202 and distal portion 204 of occluder 200 transitions from the collapsed delivery state to the expanded deployed state, central portion 207 of occluder 200 contracts radially inward, e.g., while positioned across the atrial septal defect, such that proximal portion 202 and distal portion 204 have disk-like structures.

As shown in FIG. 15B, during step 326, the distal regions of outer shaft 106 and inner shaft 108, and accordingly proximal end 203 and distal end 205 of occluder 200, may be spaced apart by a shorter distance such that occluder 200 may be in an almost fully expanded delivery state. Next, during step 326, slidable outer shaft actuator 140 may be further actuated, e.g., moved distally to its distal-most position relative to handle body 131 towards rotatable outer shaft actuator 170, to move the distal region of outer shaft 106, and accordingly proximal end 203 of occluder 200 coupled thereto, distally towards the distal region of inner shaft 108, and accordingly distal end 205 of occluder 200 coupled thereto, to thereby transition proximal portion 202 of occluder 200 to its fully expanded deployed state within the right atrium and transition distal portion 204 of occluder 200 to its fully expanded deployed state within the left atrium, as shown in FIG. 15C.

Figure 15C:
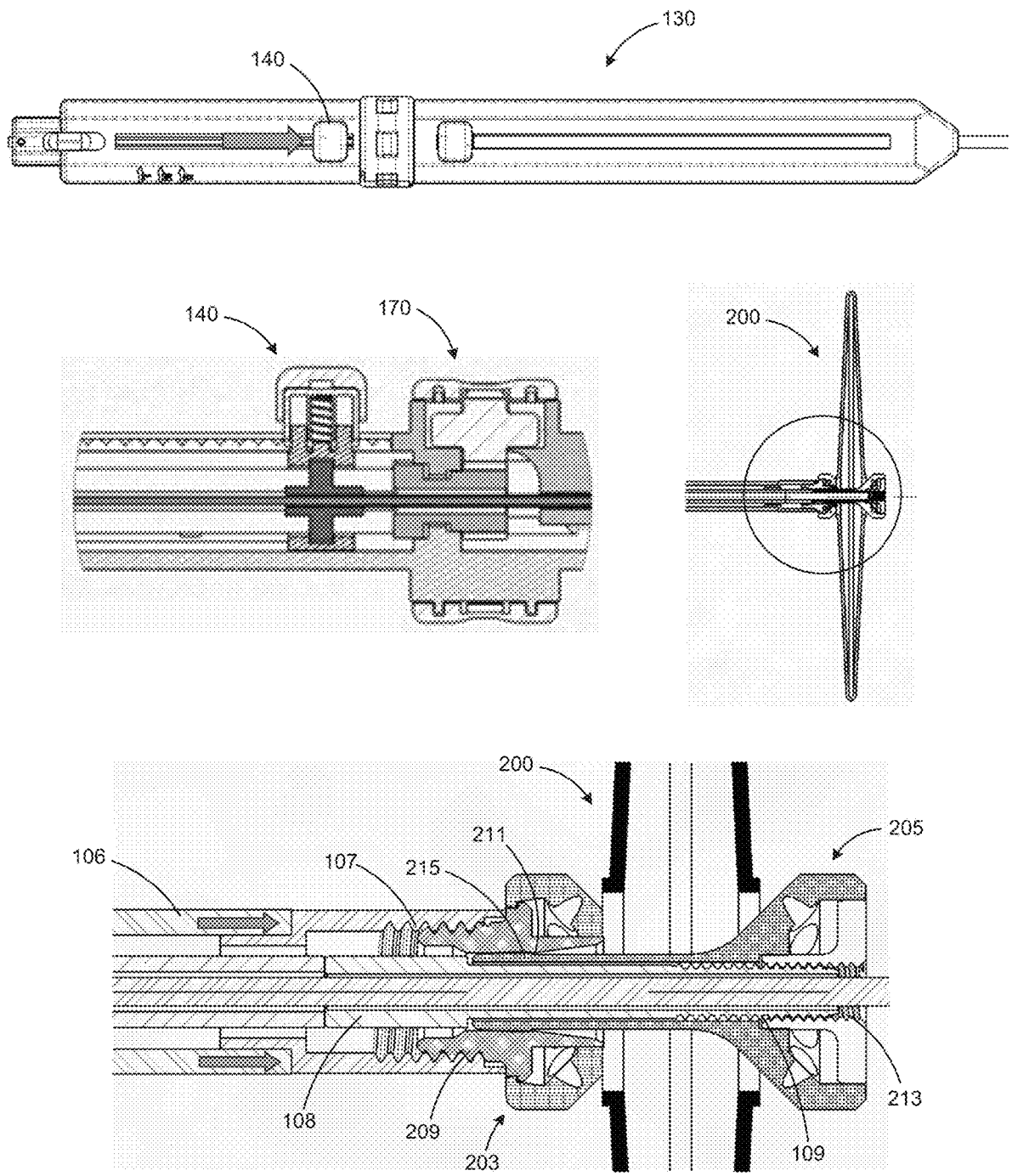

At this stage, the distal regions of outer shaft 106 and inner shaft 108, and accordingly proximal end 203 and distal end 205 of occluder 200, may be spaced apart by an even shorter distance such that occluder 200 may be in a fully expanded deployed and locked state, and proximal end 203 may be locked to distal end 205 of occluder 200, e.g., via a snap fit connection by protrusion 215 of distal end 205 of occluder 200 and groove 211 of proximal end 203 of occluder 200, as shown in FIG. 15C, to thereby accommodate the system elasticity and dimensional tolerances. For example, when proximal end 203 is locked to distal end 205, inner shaft 108 may be elastically elongated by the tensile load generated during locking of proximal end 203 to distal end 205. If proximal end 203 needs to be unlocked to distal end 205 for any reason, e.g. wrong size chosen, technical malfunction, etc., outer shaft 106 may be/retracted via outer shaft actuator 140 to disengage protrusion 215 from groove 211. In the fully expanded deployed and locked state, the disk-like structures of proximal portion 202 and distal portion 204 sandwiches the atrial septum. As will be understood by a person having ordinary skill in the art, slidable outer shaft actuator 140 may be moved from the position shown in FIG. 15C to the position shown in FIG. 15A in a single motion, without stopping slidable outer shaft actuator 140 in the position shown in FIG. 15B.

Figure 15D:
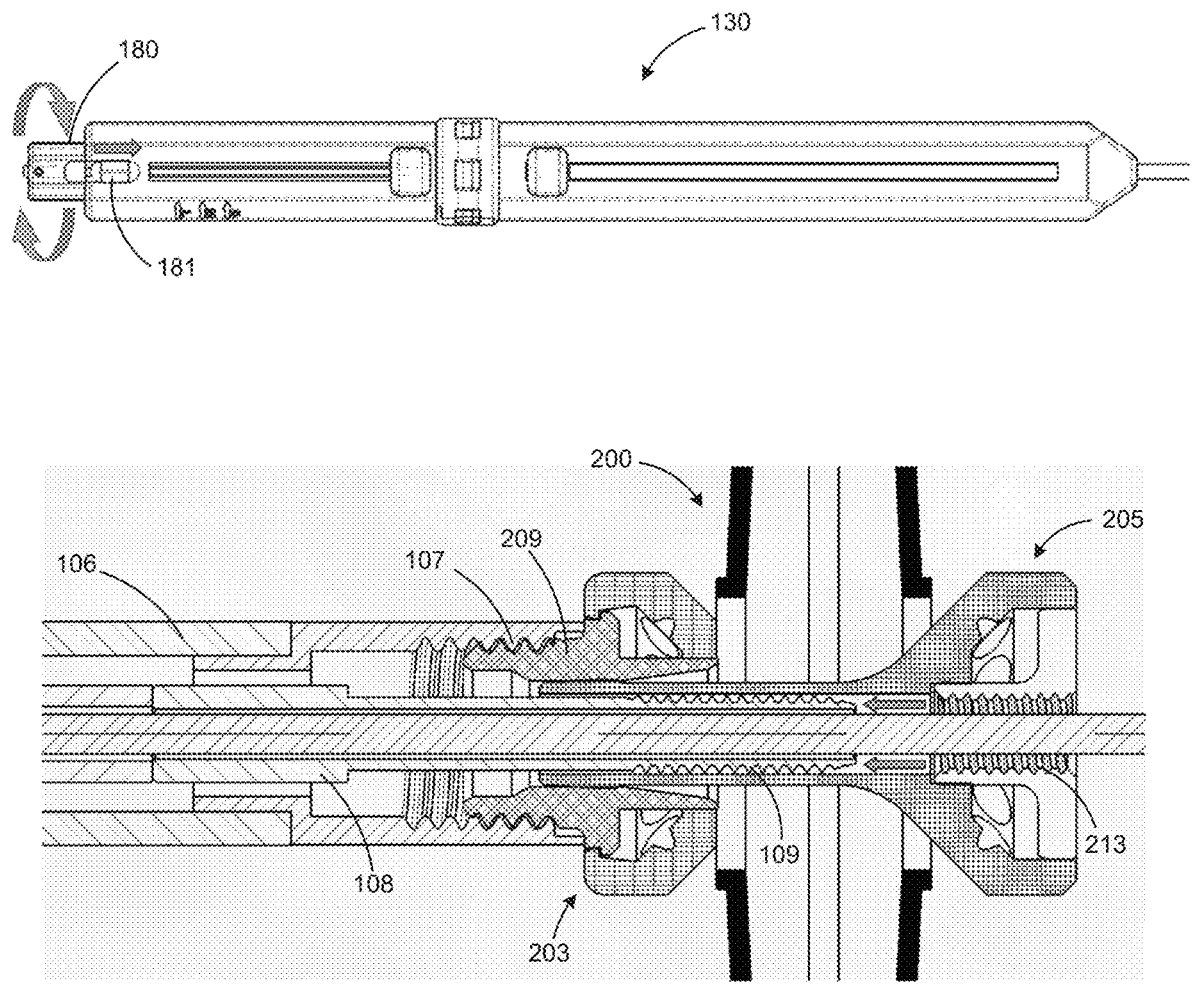
Figure 15E:
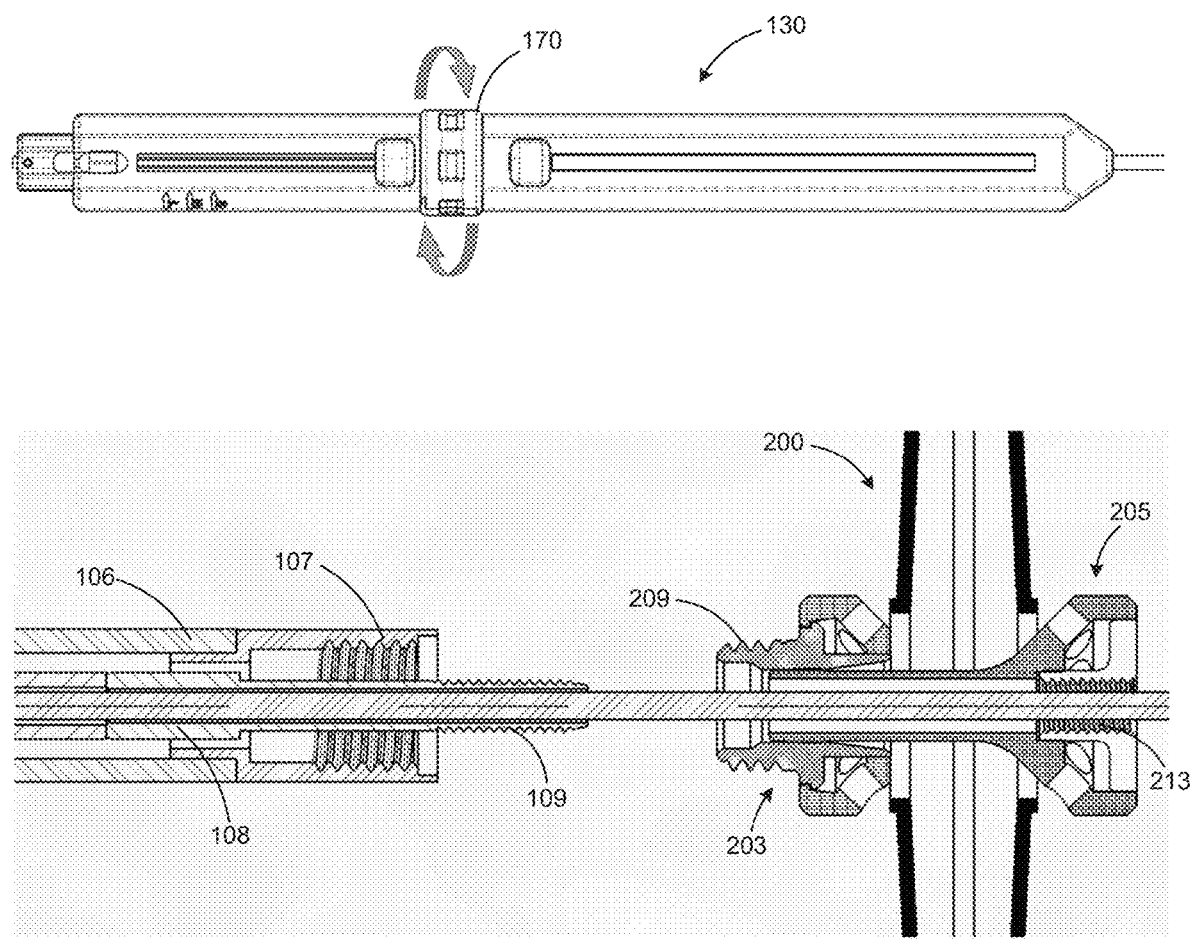

At step 328, latch 181 may be actuated to unlock rotatable inner shaft actuator 180, and rotatable inner shaft actuator 180 may be actuated, e.g., rotated, as shown in FIG. 15D, to thereby cause rotation of inner shaft 108, which causes threaded surface 109 at the distal region of inner shaft 108 to decouple from threaded surface 213 of distal end 205 of occluder 200. As described above, inner shaft 108 may be elastically elongated by the tensile load generated during locking of proximal end 203 to distal end 205, such that, upon disengagement of inner shaft 108 from proximal end 205 of occluder 200, inner shaft 108 may recoil, thereby ascertaining effective release of inner shaft 108 from distal end 205, as shown in FIG. 15D. At step 330, rotatable outer shaft actuator 170 may be actuated, e.g., rotated, which causes rotation of outer shaft 106 via rotation of planet gear 172, sun gear 174 and transmission shaft 176, and connector 146 via pins 147, which causes threaded surface 107 at the distal region of outer shaft 106 to decouple from threaded surface 209 of proximal end 203 of occluder 200, as shown in FIG. 15E.

Figure 15F:
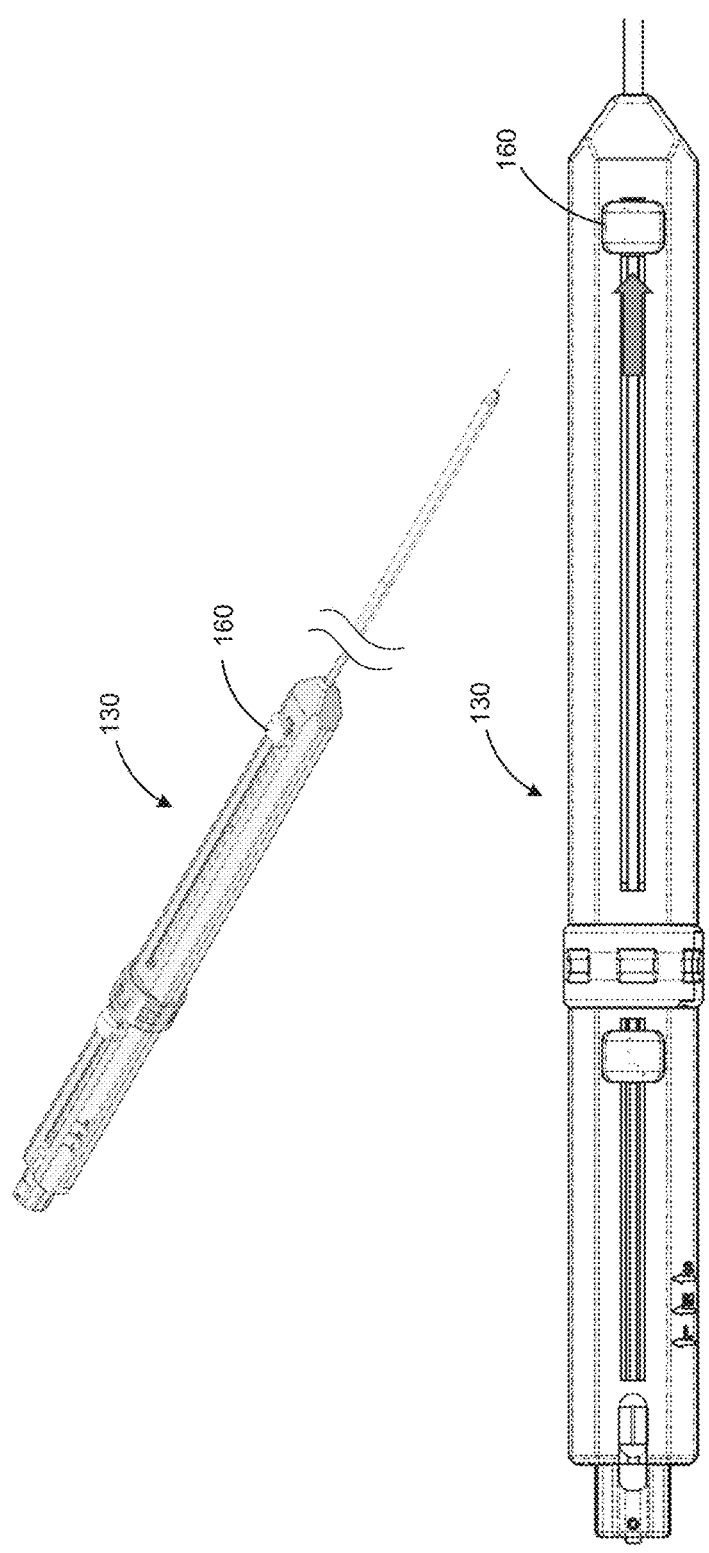
Figure 15F:
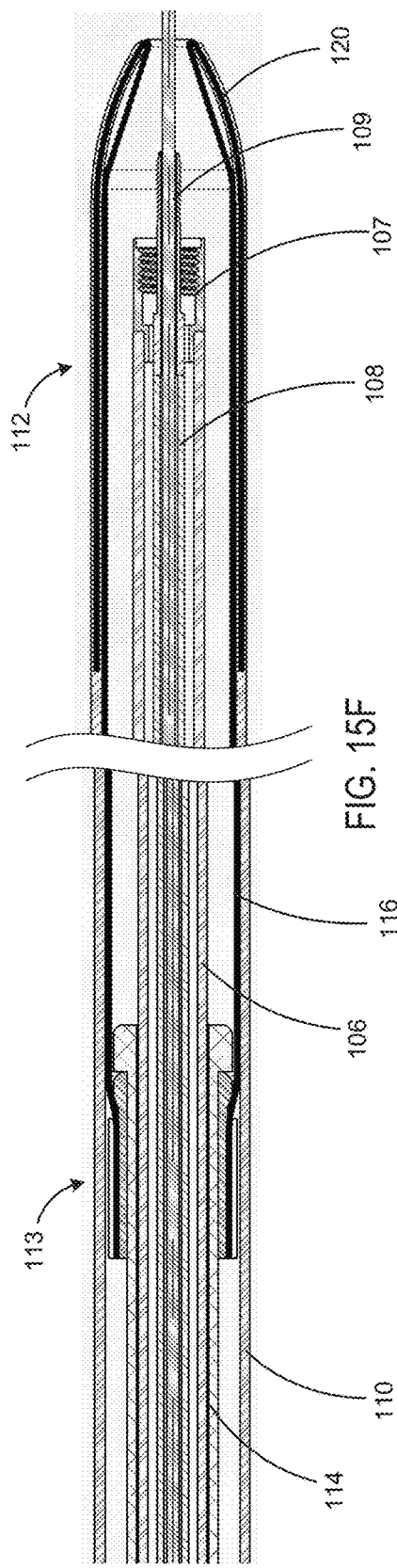

Accordingly, at step 332, delivery system 100 may be removed from the patient's body, leaving occluder 200 implanted at the atrial septum. Prior to removal of system 100 from the patient's body, outer sheath actuator 160 may be actuated (e.g., moved to its distal-most position relative to handle body 131) to move outer sheath 110 distally relative to fixed shaft 114, outer shaft 106, and inner shaft 108, such that atraumatic tip 120 is formed, as shown in FIG. 15F, to thereby facilitate removal of system 100 from the patient's body. As will be understood by a person having ordinary skill in the art, prior to decoupling of occluder 200 from inner and outer shafts 108, 106 or after reconnecting occluder 200 to inner and outer shafts 108, 106 at the atrial septum, slidable outer shaft actuator 140 may be actuated to transition occluder 200 back to its collapsed delivery state, and/or outer sheath actuator 160 may be actuated to recapture/reload occluder 200 within outer sheath 110, to thereby permit the user to reposition/realign occluder 200 for proper implantation at the atrial septum. Moreover, method 320 similarly may be used to deliver occluder 200 to an atrial septum of a patient having an atrial septal defect using delivery system 400, as described in further detail below with regard to FIGS. 21A to 21F.

Figure 16:
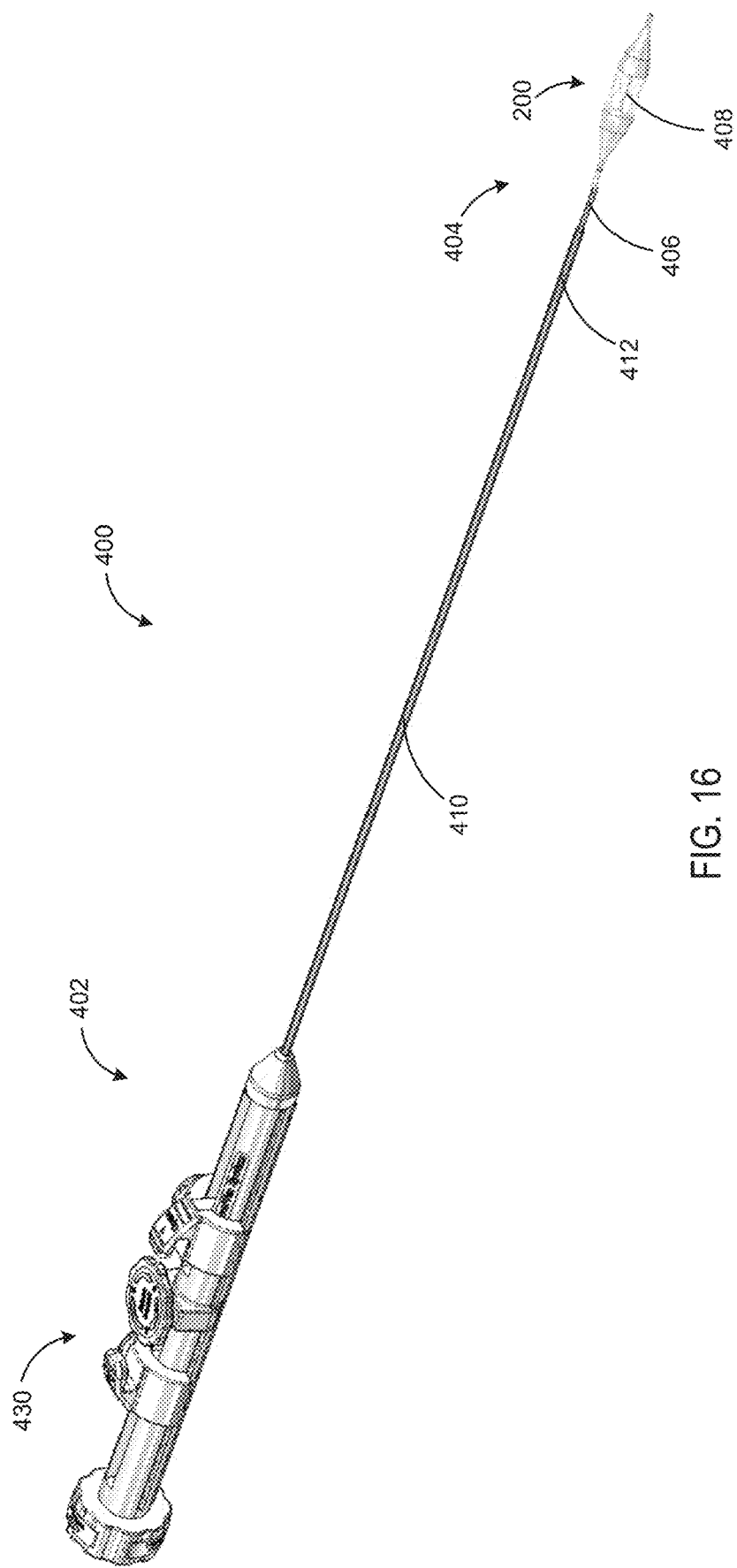
FIG. 16 illustrates an alternative exemplary system for delivering an implantable occluder device to an atrial septum constructed in accordance with the principles of the present disclosure.

Referring now to FIG. 16, an alternative exemplary system for delivering an implantable occluder device to an atrial septum of a patient's heart is provided. Delivery system 400 may be configured to deliver an ASD occluder device, e.g., occluder 200, to the atrial system in a collapsed delivery state within system 400, and may further may be actuated, e.g., via handle 430, to deploy occluder 200 at the atrial septum to thereby close the atrial septal defect. Delivery system 400 may be constructed like delivery system 100. For example, delivery system 400 may include handle 430 at proximal region 402, and outer shaft 406 having threaded surface 407, e.g., disposed on inner surface of the lumen of outer shaft 406 and configured to be removeably engage with threaded surface 209 of proximal end 203 of occluder 200, inner shaft 408 having threaded surface 409, e.g., disposed on an outer surface at the distal region of inner shaft 408 and configured to removeably engage with threaded surface 213 of distal end 205 of occluder 200, and outer sheath 410, operatively coupled to and extending from handle 430 towards distal region 404, which correspond with handle 130 at proximal region 102, and outer shaft 106 having threaded surface 107, inner shaft having threaded surface 109, and outer sheath 110, extending from handle 130 towards distal region 104. System 400 differs from system 100 in that system 400 does not include a fixed shaft or an invertible braided structure at the distal region for facilitating loading and unloading of the occluder from within outer sheath 410. Instead, outer sheath 410 may include expandable distal region 412, as described in further detail below with regard to FIG. 17.

Figure 17:
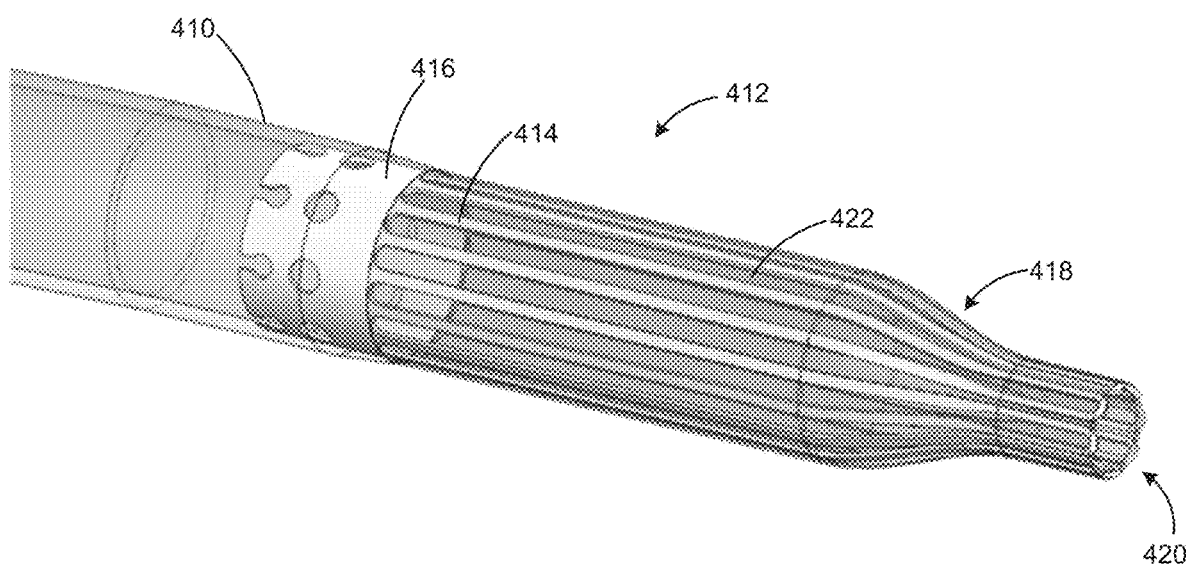
FIG. 17 illustrates the distal region of an exemplary outer sheath of the delivery system of FIG. 16.

Referring now to FIG. 17, distal region 412 of outer sheath 410 is provided. Outer sheath 410 may be slidably disposed over outer shaft 406 and occluder 200 in its collapsed delivery. Accordingly, outer sheath 410 has a lumen sized and shaped to receive occluder 200 therein in the collapsed delivery state. The proximal region of outer sheath 410, i.e., proximal to distal region 412, may be formed of a braided structure. As shown in FIG. 17, distal region 412 of outer sheath 410 may be formed by a plurality of flexible, longitudinally extending struts 414 encapsulated by expandable membrane 422. For example, struts 414 may extend longitudinally from collar 416 coupled to a distal end of the proximal region of outer sheath 410, and may be arranged circumferentially about a longitudinal axis of outer sheath 410 to define the lumen of distal region 412 sized and shaped to receive occluder 200 in the collapsed delivery state. As shown in FIG. 17, struts 414 may comprise a plurality of longitudinally extending U-shaped struts extending circumferentially along distal region 412. Struts 414 may formed of a shape-memory material, e.g., Nitinol. For example, struts 414 may be cut from a straight Nitinol tube, and shaped to set into an atraumatic cone geometry at its distal end.

Accordingly, at least a distal portion of distal region 412 may be configured to transition between a collapsed delivery configuration and an expanded configuration, e.g., upon application of force against an inner surface of the distal portion of distal region 412. For example, as shown in FIG. 17, longitudinally extending struts 414 may define transition zone 418 and tip 420 at the distal portion of distal region 412. In the collapsed configuration shown in FIG. 17, the cross-sectional area of distal region 412 may decrease in the distal direction along transition zone 418 towards tip 420, thereby forming an atraumatic tip configured to facilitate navigation through the patient's anatomy. As shown in FIG. 17, the cross-sectional of distal region 412 may be constant along tip 420. Alternatively, tip 420 may have an atraumatic cone shape. The distal portion of distal region 412 may be biased towards the collapsed delivery configuration.

Upon application of force against the inner surface of struts 414 at transition zone 418 and tip 420, struts 414 defining transition zone 418 and tip 420 may expand radially outward to an expanded configuration sized and shaped to facilitate passage of occluder 200 therethrough. For example, in the expanded configuration, the cross-sectional area of distal region 412 at tip 420 may be the same or larger than the cross-sectional area of distal region 412 along transition zone 418. Accordingly, in the expanded configuration, the cross-sectional area of distal region 412 may be constant or increase along transition zone 418 towards tip 420 based on the amount of force applied, e.g., via occluder 200 as occluder 200 is passed through the distal portion of distal region 412, such as during loading, recapture, and/or deployment of occluder 200 from outer sheath 410.

Figure 18A:
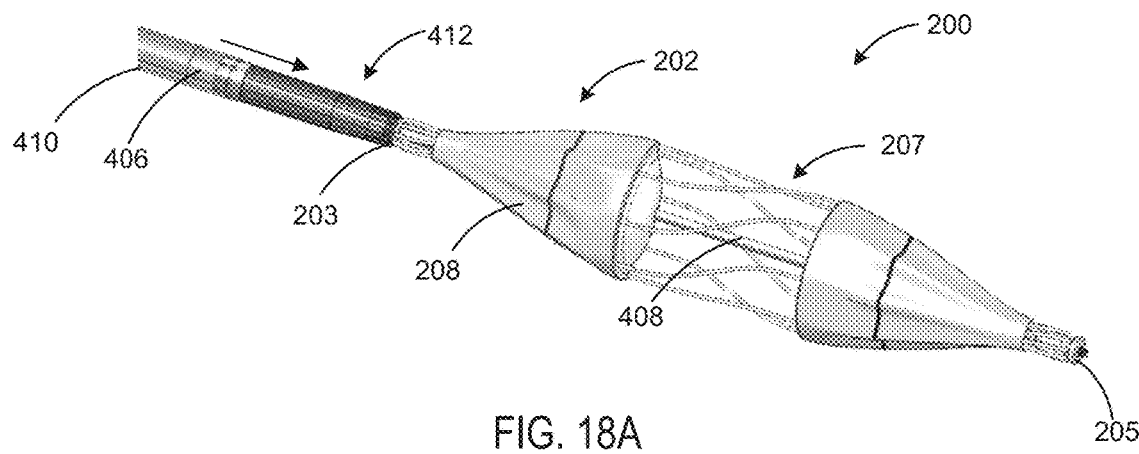
FIGS. 18A to 18C illustrate an exemplary method for loading the occluder device of FIG. 2A within the outer sheath in accordance with the principles of the present disclosure.
Figure 18B:
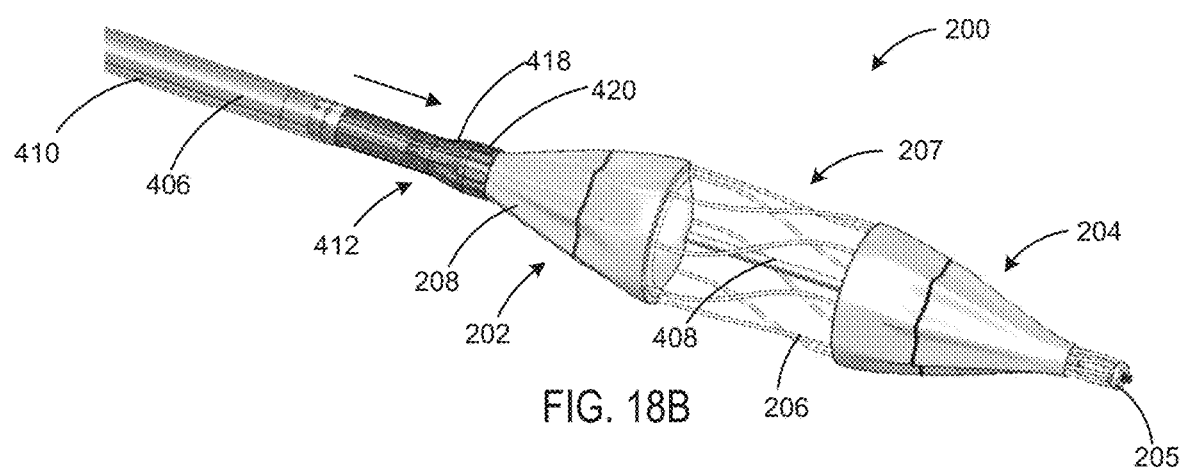
Figure 18C:
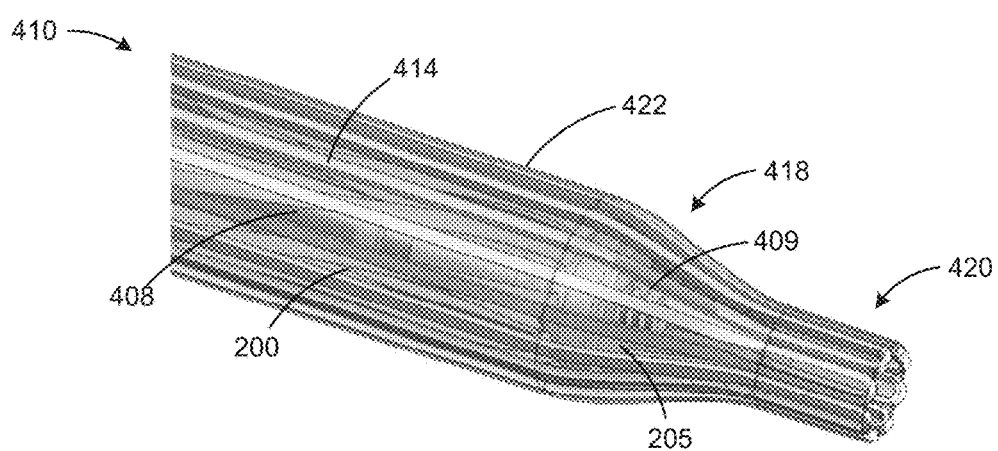

Referring now to FIGS. 18A to 18C, method 300 of FIG. 12, may be used for loading occluder 200 into outer sheath 410. For example, as step 302, outer sheath 410 may be retracted relative to outer shaft 406 and inner shaft 208 via outer sheath actuator 460. At step 304, proximal end 203 of occluder 200 may be removably coupled to the distal region of outer shaft 406, and distal end 205 may be removably coupled to the distal region of inner shaft 408 slidably disposed within and extending distally from outer shaft 406. As shown in FIG. 18A, the distal regions of outer shaft 406 and inner shaft 408, and accordingly, proximal end 203 and distal end 205 of occluder 200, may be spaced apart such that occluder 200 in is a semi-collapsed delivery state with an elongated configuration along inner shaft 408. At step 306, outer shaft 406 may be retracted proximally relative to inner shaft 408 via outer shaft actuator 440 to transition occluder 200 towards its collapsed delivery state.

At step 308, outer sheath 410 may be advanced distally over outer shaft 406 until distal region 412 contacts and expands over proximal end 203 and proximal portion 202 of occluder 200, e.g., due to the force applied to the inner surface of distal region 412 along transition zone 418 and tip 420 by occluder 200 as distal region 412 is advanced over occluder 200, as shown in FIGS. 18A and 18B. As will be understood by a person having ordinary skill in the art, while FIG. 18B shows only transition zone 418 and tip 420 of distal region 412 expanding radially to the expanded configuration to receive occluder 200 therethrough, at least a portion of distal region 412 proximal to transition zone 418 also may expand radially to facilitate loading of occluder 200 into the lumen of outer sheath 410. Moreover, as occluder 200 is passed into the lumen of distal region 412 and outer sheath 410, the inner walls of distal region 412 and outer sheath 410 apply a force against occluder 200 to thereby facilitate further radial contraction of occluder 200 to the fully collapsed delivery state within outer sheath 410, as shown in FIG. 18C. Outer sheath 410 may be advanced distally relative to outer shaft 406 and inner shaft 408, and accordingly over proximal portion 202, central portion 207, and distal portion 204 of occluder 200, until occluder 200 is fully disposed within the lumen of outer sheath 410 in its collapsed delivery state, and distal region 412 returns to the collapsed delivery configuration. As shown in FIG. 18C, when distal region 412 is in the collapsed delivery configuration with occluder 200 loaded therein, distal end 205 of occluder 200 may be positioned adjacent to transition zone 418 of distal region 412, such that tip 420 forms an atraumatic tip to facilitate navigation of outer sheath 410 through the patient's body to the atrial septum. In addition, in the collapsed delivery configuration, tip 420 may define a lumen sized and shaped to receive a guidewire therethrough.

Referring now to FIGS. 19A and 19B, an exemplary handle of delivery system 400 for actuating deployment and delivery of occluder 200 at the atrial septum is provided. Handle 430 may include handle body 432 sized and shaped to be held and operated by a user, and may be operatively coupled to the proximal regions of outer shaft 406, inner shaft 408, and outer sheath 410. For example, handle 430 may include a plurality of sliders and knob actuators, e.g., slidable outer shaft actuator 440 operatively coupled to the proximal region of outer shaft 406, slidable outer sheath actuator 460 fixedly coupled to the proximal region of outer sheath 410, rotatable outer shaft actuator 470 configured to be operatively coupled to the proximal region of outer shaft 406, and rotatable inner shaft actuator 480 fixedly coupled to the proximal region of inner shaft 408. As shown in FIGS. 19A and 19B, slidable outer shaft actuator 440, slidable outer sheath actuator 460, and rotatable inner shaft actuator 480 may be arranged on handle body 432, such that outer shaft 406 is slidably disposed over inner shaft 408, and outer sheath 410 is slidably disposed over outer shaft 406. Moreover, the axial position of rotatable inner shaft actuator 480, and accordingly inner shaft 408, may be fixed relative to handle body 432.

As shown in FIGS. 19A and 19B, handle body 432 may include one or more tracks, e.g., track 434 configured to slidably receive slidable outer shaft actuator 440 and track 436 configured to slidably receive outer sheath actuator 460. Accordingly, slidable outer shaft actuator 440 may be moved relative to handle body 432 along track 434 to thereby move outer shaft 406 relative to inner shaft 408 and outer sheath 410, and outer sheath actuator 460 may be moved relative to handle body 432 along track 436 to thereby move outer sheath 410 relative to inner shaft 408 and outer shaft 406. For example, as shown in FIGS. 19A and 19B, slidable outer shaft actuator 440 may include tab 441 configured to facilitate movement of slidable outer shaft actuator 440 by a user, locking mechanism 442 configured to be actuated to lock the position of slidable outer shaft actuator 440 relative to handle body 432, outer shaft housing 444 configured to be operatively coupled to outer shaft 406, e.g., via bevel gear 446 and splined rotary shaft 450, as described in further detail below with regard to FIGS. 20A and 20B, and neck portion 443 extending between tab 442 and outer shaft housing 444 and sized and shaped to be slidably received through track 434, such that slidable outer shaft actuator 440 moves along handle body 430 via slidable engagement between track 434 and neck portion 443. Moreover, outer sheath actuator 460 may include tab 461 configured to facilitate movement of outer sheath actuator 460 by a user, locking mechanism 462 configured to be actuated to lock the position of outer sheath actuator 460 relative to handle body 432, outer sheath housing 464 configured to be fixedly coupled to outer sheath 410, and neck portion 463 extending between tab 461 and outer sheath housing 464 and sized and shaped to be slidably received through track 436, such that outer sheath actuator 460 moves along handle body 430 via slidable engagement between track 436 and neck portion 463.

As shown in FIG. 19B, the axial position of rotatable outer shaft actuator 470 may be fixed relative to handle body 432, and rotatable outer shaft actuator 470 may include bevel gear 472 configured to releasably and operatively engage with bevel gear 446 of slidable outer shaft actuator 440 when slidable outer shaft actuator 440 is moved to the distal-most position along track 434. Accordingly, when bevel gear 472 is engaged with bevel gear 446, rotational movement of outer shaft actuator 470, and accordingly bevel 472, may be transmitted to bevel gear 446, and accordingly outer shaft 406, via bevel gear 472 and bevel gear 446, to thereby rotate outer shaft 406 to disengage threaded surface 407 of outer shaft 406 from threaded surface 209 of proximal end 203 of occluder 200.

Figure 20A:
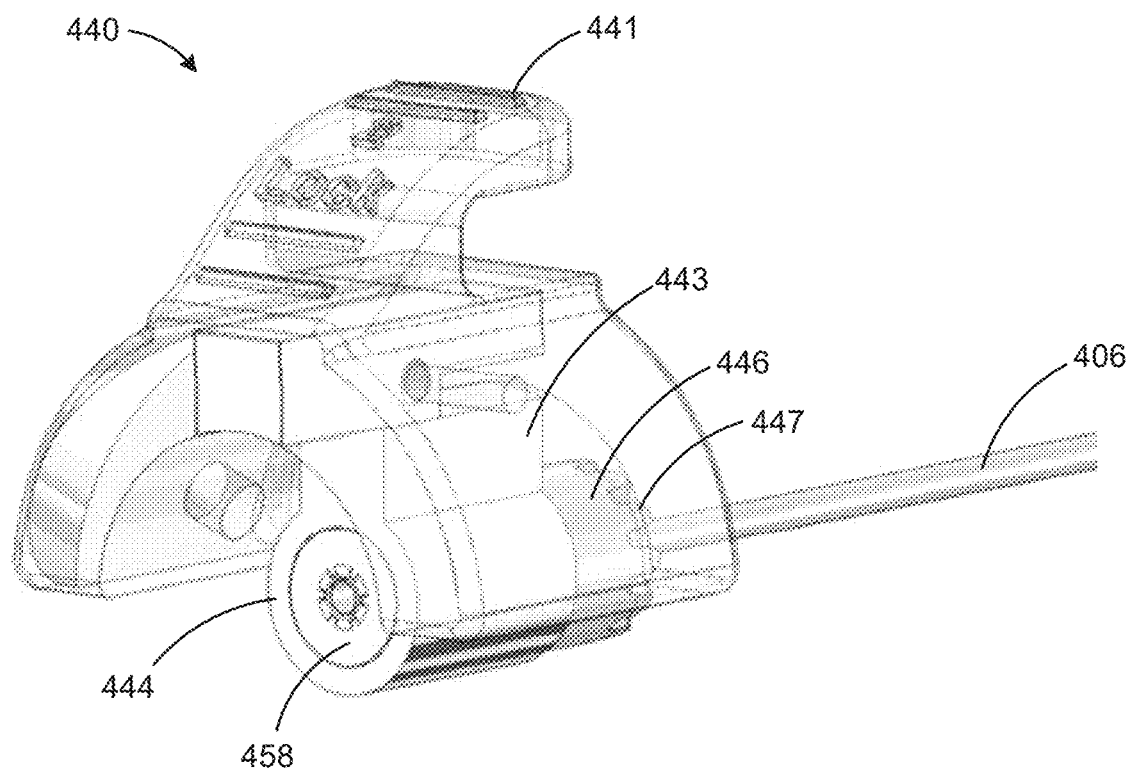
FIGS. 20A and 20B illustrate an exemplary outer shaft actuator of the handle of FIGS. 20A and 20B.
Figure 20B:
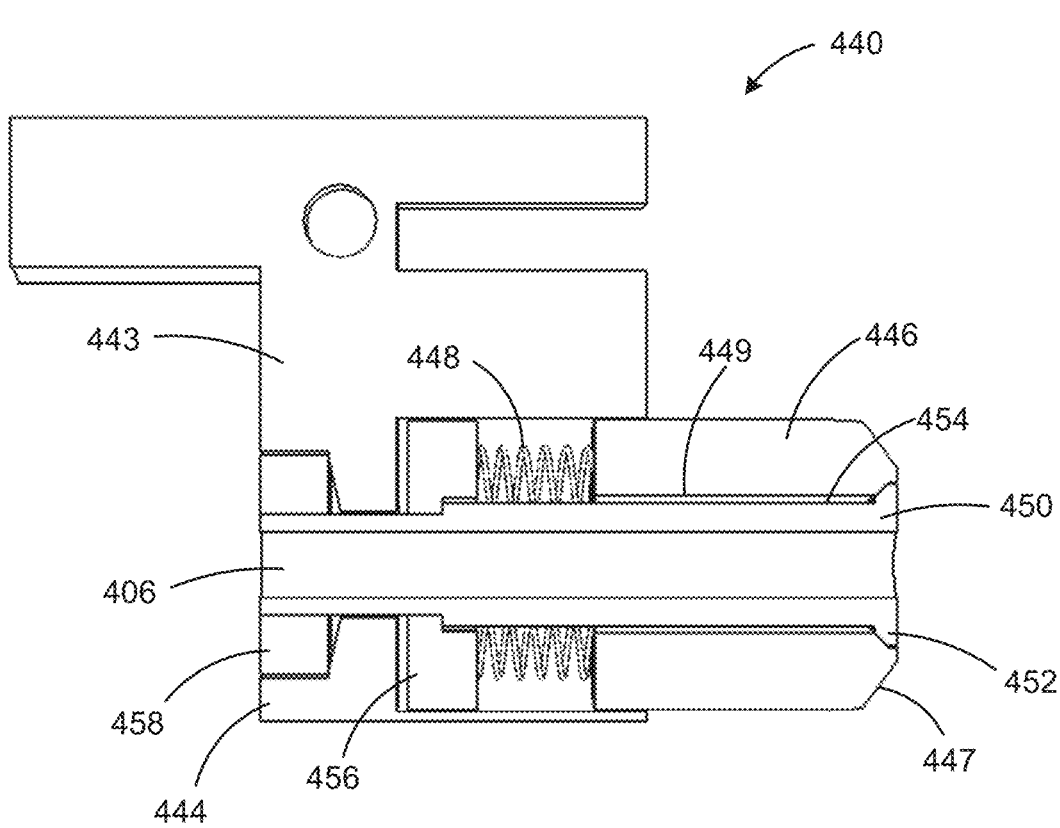

Referring now to FIGS. 20A and 20B, slidable outer shaft actuator 440 is provided in further detail. As shown in FIG. 20A, slidable outer shaft actuator 440 may be operatively coupled to outer shaft 406 via bevel gear 446 rotatably disposed within outer shaft housing 444, and bevel gear 446 may have geared surface 447 configured to releasably engage with the geared surface of bevel gear 472 of rotatable outer shaft actuator 470. As shown in FIG. 20B, bevel gear 446 may be operatively coupled to outer shaft 406 via splined rotary shaft 450 fixedly coupled to the proximal region of outer shaft 406 and rotatably disposed within housing 444. For example, splined rotary shaft 450 may include a plurality of longitudinally extending splines 454 arranged circumferentially along the outer surface of splined rotary shaft 450, and the inner surface of bevel gear 446 may include a plurality of corresponding longitudinally extending grooves 449 sized and shaped to engage with splines 454 in a manner such that relative rotation between bevel gear 446 and splined rotary shaft 450 is inhibited. Accordingly, rotation of bevel gear 446, e.g., via rotation of rotatable outer shaft actuator 470 via bevel gear 472, will cause rotation of splined rotary shaft 450, and accordingly, outer shaft 406.

Moreover, the distal end of splined rotary shaft 450 may include lip 452 extending radially outward to thereby engage with and prevent distal movement of bevel gear 446 beyond lip 452. For example, the distal end of bevel gear 446 may include a ledge sized and shaped to engage with lip 452 when bevel gear 446 is at its distal-most position relative to splined rotary shaft 450. In addition, slidable outer shaft actuator 440 may include one or more compression springs 448 coupled to the proximal end of bevel gear 446, such that the spring force of springs 448 push bevel gear 446 axially in a distal direction towards lip 452 of splined rotary shaft 450, to thereby keep bevel gear 446 in contact with splined rotary shaft 450. Accordingly, bevel gear 446 is permitted to move axially relative to splined rotary shaft 450, but cannot rotate relative to splined rotary shaft 450.

As shown in FIG. 20B, slidable outer shaft actuator 440 may include one or more washers, e.g., washer 458 and washer 456 configured to prevent axial movement of splined rotary shaft 450, and accordingly outer shaft 406, relative to slidable outer shaft actuator 440, while permitting rotational movement of bevel gear 446, and accordingly splined rotary shaft 450 and outer shaft 406, relative to slidable outer shaft actuator 440. For example, washer 456 may be disposed within housing 444 proximal to springs 448, and may have a lumen extending therethrough sized and shaped to receive at least a portion of splined rotary shaft 450 therethrough. As the axial position of splined rotary shaft 450 is fixed relative to slidable outer shaft actuator 440, bevel gear 446 may be moved proximally relative to splined rotary shaft 450 upon application of an axial force thereon, e.g., via bevel gear 472 as slidable outer shaft actuator 440 is moved towards rotatable outer shaft actuator 470, thereby compressing springs 448. As described above, slidable outer shaft actuator 440 may be locked relative to handle body 432 via actuation of locking mechanism 442. Accordingly, when slidable outer shaft actuator 440 is locked in its distal-most position relative to handle body 432 and bevel gear 446 is moved proximally relative to splined rotary shaft 450 via engagement with bevel gear 472, springs 448 applies a force against bevel gear 446 to thereby maintain contact between bevel gear 446, and accordingly splined rotary shaft 450 and outer shaft 406, and bevel gear 472, such that rotational movement of bevel gear 472 may be transmitted to outer shaft 406 via bevel gear 446 and splined rotary shaft 450.

Figure 21A:
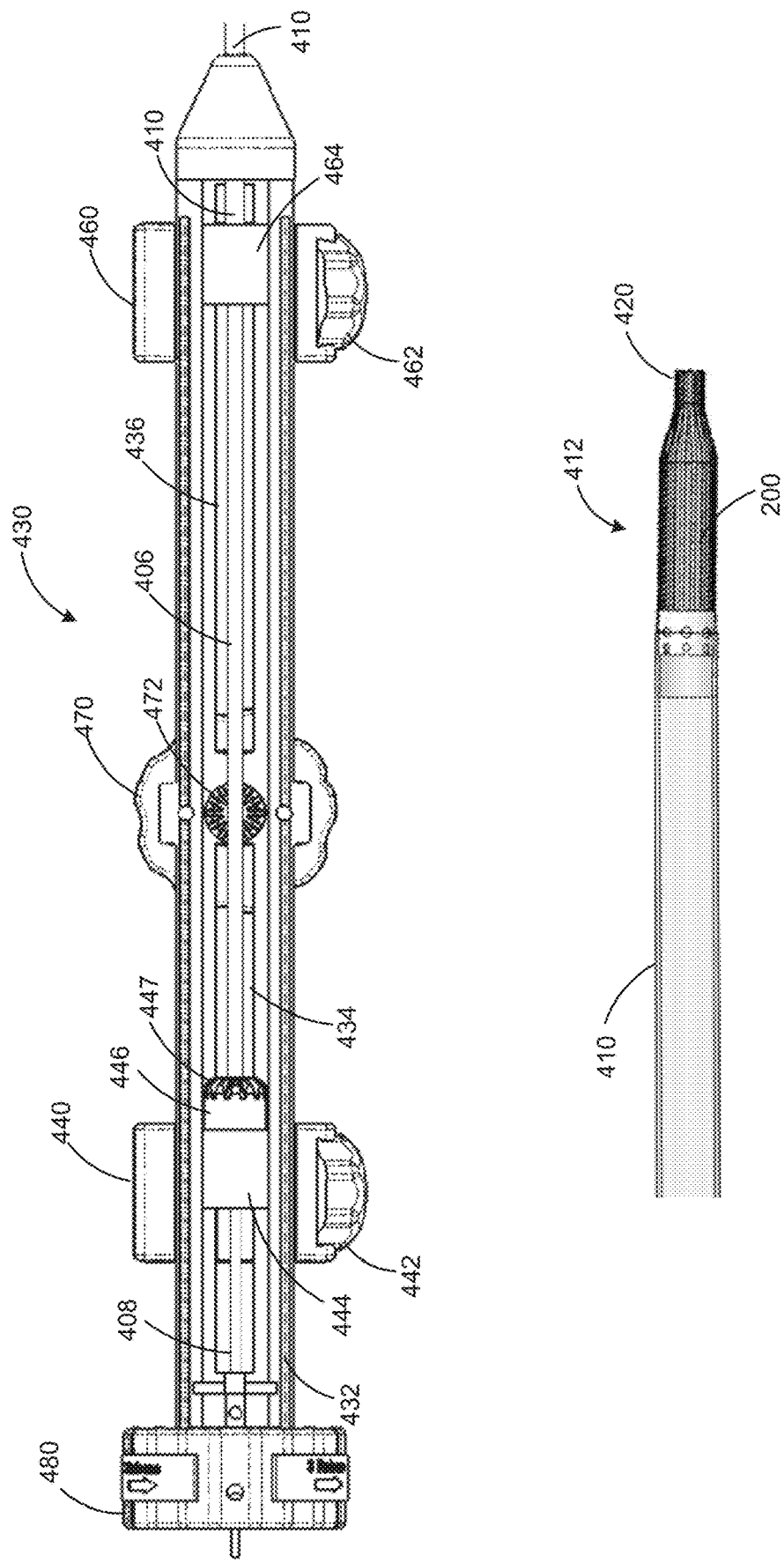
FIGS. 21A to 21F illustrate exemplary method steps for delivering the occluder device of FIG. 2A using the delivery system of FIG. 16 in accordance with the principles of the present disclosure.

Referring now to FIGS. 21A to 21F, method 320 of FIG. 14, may be used for delivering occluder 200 to an atrial septum of a patient having an atrial septal defect using delivery system 400. Initially, occluder 200 may be loaded into outer sheath 410 in its collapsed delivery state, as described above with regard to FIGS. 18A to 18C. As shown in FIG. 21A, when occluder 200 is coupled to outer shaft 406 and inner shaft 408 and loaded within outer sheath 410 in its collapsed delivery state, slidable outer shaft actuator 440 may be spaced apart from rotatable outer shaft actuator 470 by a distance along handle body 432 by a distance corresponding with the distance between proximal end 203 and distal end 205 of occluder 205, and outer sheath actuator 460 may be at its distal-most position along handle body 432, such that tip 420 of distal region 412 of outer sheath 410 extends distally beyond occluder 200 in its collapsed delivery configuration to define an atraumatic tip. A guidewire may then be advanced through the patient's body to the atrial septum, e.g., through the atrial septal defect.

Figure 21B:
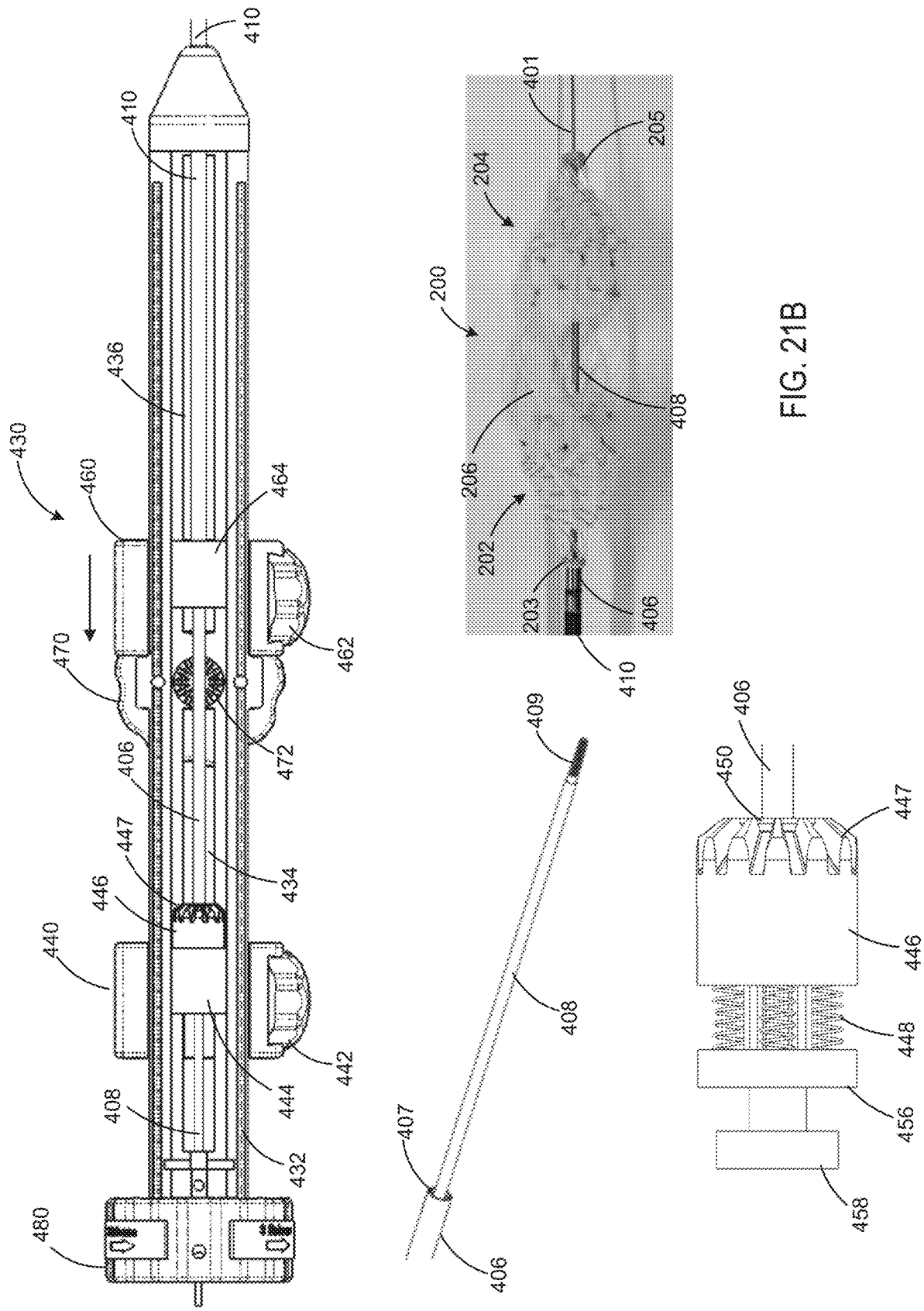

At step 322, outer sheath 410 having occluder 200 disposed therein may be advanced over the guidewire to the patient's atrial septum. Distal region 412 may be advanced across the atrial septal defect to thereby align occluder 200 disposed within outer sheath 410 with the atrial septum, such that distal portion 204 is disposed within a first atrium, e.g., the left atrium, and proximal portion 202 is disposed within a second atrium, e.g., the right atrium. At step 324, outer sheath actuator 460 may be actuated, e.g., moved proximally relative to handle body 432, to retract outer sheath 410 proximally relative to outer shaft 406 and inner shaft 408, and accordingly occluder 200, to thereby expose occluder 200 beyond the distal end of distal region 412 of outer sheath 410 in its collapsed delivery state, as shown in FIG. 21B. As shown in FIG. 21B, at step 324, the distal regions of outer shaft 406 and inner shaft 408, and accordingly proximal end 203 and distal end 205 of occluder 200 (omitted in the left figure for clarity), may be spaced apart by a distance such that occluder 200 may be in a semi-collapsed delivery state with an elongated configuration along inner shaft 408. Accordingly, upon exposure from outer sheath 410, occluder 200 may at least partially self-expand from the fully collapsed delivery state within outer sheath 410 to a semi-collapsed delivery state, as shown in FIG. 21B. FIG. 21B further illustrates the relative axial position between bevel gear 446 and splined rotary shaft 450 at step 304. As shown in FIG. 21B, at step 324, springs 448 cause bevel gear 446 to be at its distal-most axial position relative to splined rotary shaft 450. Moreover, locking mechanism 462 may be actuated to lock the axial position of outer sheath actuator 460, and accordingly outer sheath 410, relative to handle body 432.

Figure 21C:
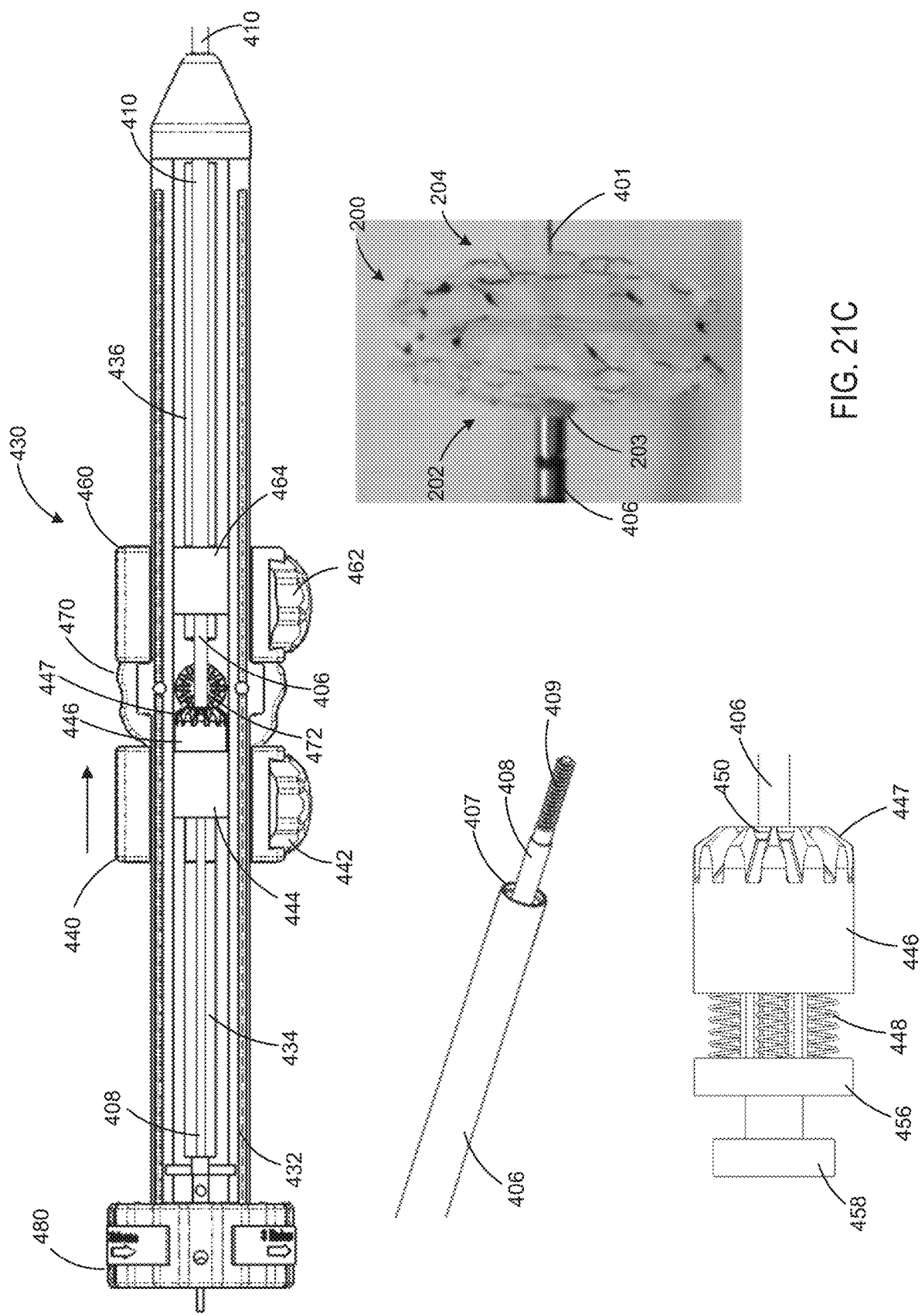

At step 326, slidable outer shaft actuator 440 may be actuated, e.g., moved distally relative to handle body 432 towards rotatable outer shaft actuator 470, to move the distal region of outer shaft 406, and accordingly proximal end 203 of occluder 200 coupled thereto via threaded surface 407 and threaded surface 209, distally towards the distal region of inner shaft 408, and accordingly distal end 205 of occluder 200 coupled thereto via threaded surface 409 and threaded surface 213, to thereby transition proximal portion 202 of occluder 200 towards its expanded deployed state within the right atrium and transition distal portion 204 of occluder 200 towards its expanded deployed state within the left atrium, as shown in FIG. 21C. As described above, as proximal portion 202 and distal portion 204 of occluder 200 transitions from the collapsed delivery state to the expanded deployed state, central portion 207 of occluder 200 contracts radially inward, e.g., while positioned across the atrial septal defect, such that proximal portion 202 and distal portion 204 have disk-like structures. As shown in FIG. 21C, during step 326, the distal regions of outer shaft 406 and inner shaft 408, and accordingly proximal end 203 and distal end 205 of occluder 200 (omitted in the left figure for clarity), may be spaced apart by a shorter distance such that occluder 200 may be in an almost fully expanded delivery state. At this stage, bevel gear 446 may contact and engage with bevel gear 472 of rotatable outer shaft actuator 470; however, bevel gear 446 may be kept at its distal-most axial position relative to splined rotary shaft 450 via springs 448, as shown in FIG. 21C.

Figure 21D:
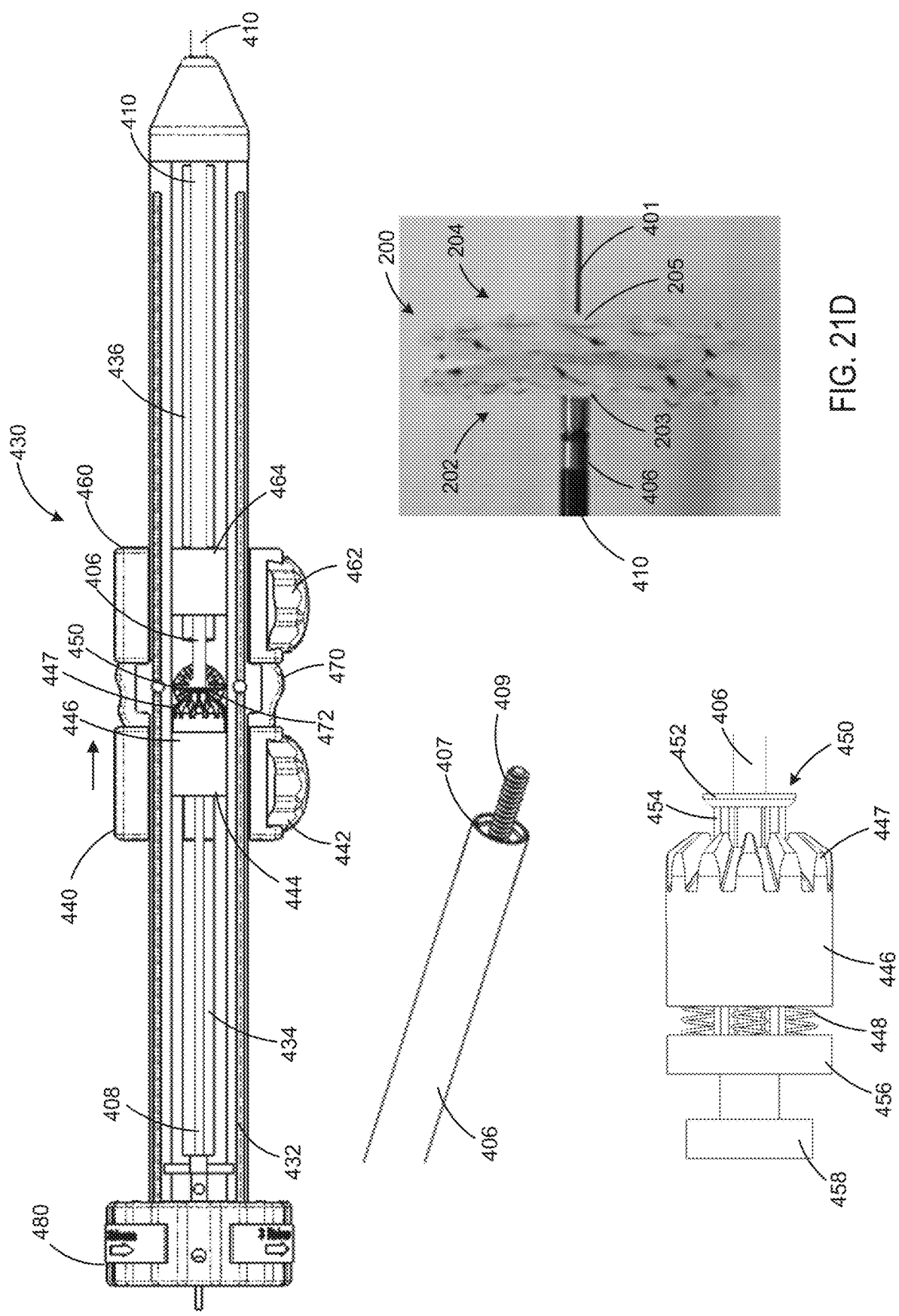

Next, during step 326, slidable outer shaft actuator 440 may be further actuated, e.g., moved distally to its distal-most position relative to handle body 432 towards rotatable outer shaft actuator 470, to move the distal region of outer shaft 406, and accordingly proximal end 203 of occluder 200 coupled thereto, distally towards the distal region of inner shaft 408, and accordingly distal end 205 of occluder 200 coupled thereto, to thereby transition proximal portion 202 of occluder 200 to its fully expanded deployed state within the right atrium and transition distal portion 204 of occluder 200 to its fully expanded deployed state within the left atrium, as shown in FIG. 21D. At this stage, the distal regions of outer shaft 406 and inner shaft 408, and accordingly proximal end 203 and distal end 205 of occluder 200 (omitted in the left figure for clarity), may be spaced apart by an even shorter distance such that occluder 200 may be in a fully expanded deployed and locked state. In the fully expanded deployed and locked state, the disk-like structures of proximal portion 202 and distal portion 204 sandwiches the atrial septum.

As slidable outer shaft actuator 440 moves further distally relative to handle body 432, e.g., after bevel gear 446 is engaged with bevel gear 472 as shown in FIG. 21C, bevel gear 472 prevents further axial distal movement of bevel gear 446 relative to handle body 432 while, splined rotary shaft 450 and outer shaft 406 move axially distally with slidable outer shaft actuator 440, as shown in FIG. 21D. For example, the force applied to bevel gear 446 by bevel gear 472 as slidable outer shaft actuator 440 moves further distally relative to handle body 432 causes bevel gear 446 to move axially proximally relative to splined rotary shaft 450, e.g., along plurality of splines 454, thereby exposing splined rotary shaft 450 and compressing springs 448. At this stage, springs 448 apply a spring force against bevel gear 446 to thereby maintain contact between bevel gear 446, and accordingly splined rotary shaft 450 and outer shaft 406, and bevel gear 472, thereby ensuring locking of proximal end 203 to distal end 205 of occluder 200, e.g., via a snap fit connection as described above, and accommodating the system elasticity and dimensional tolerances, and ensuring that bevel gear 446 is reliably operatively locked to bevel gear 472. Moreover, locking mechanism 442 may be actuated to lock the axial position of slidable outer shaft actuator 440, and accordingly outer shaft 406, relative to handle body 432. As will be understood by a person having ordinary skill in the art, slidable outer shaft actuator 440 may be moved from the position shown in FIG. 21B to the position shown in FIG. 21D in a single motion, without stopping slidable outer shaft actuator 440 in the position shown in FIG. 21C.

Figure 21E:
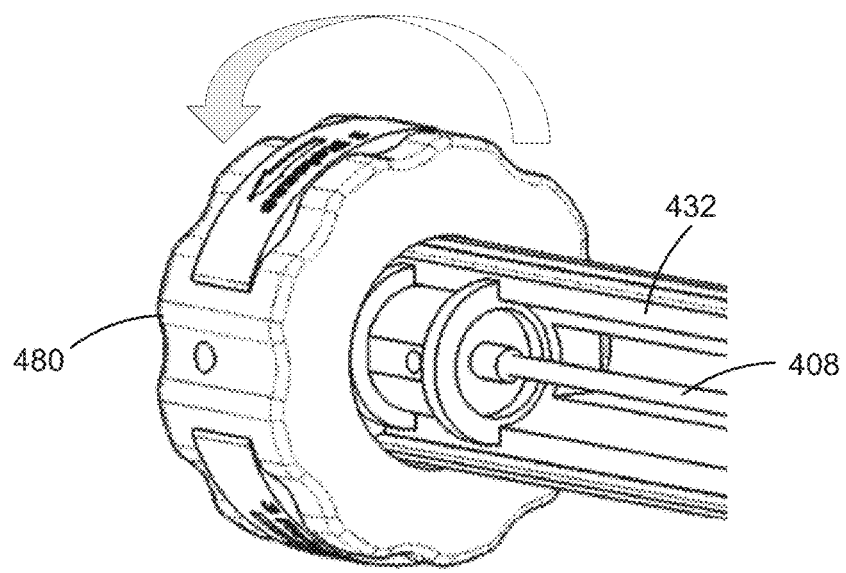
Figure 21F:
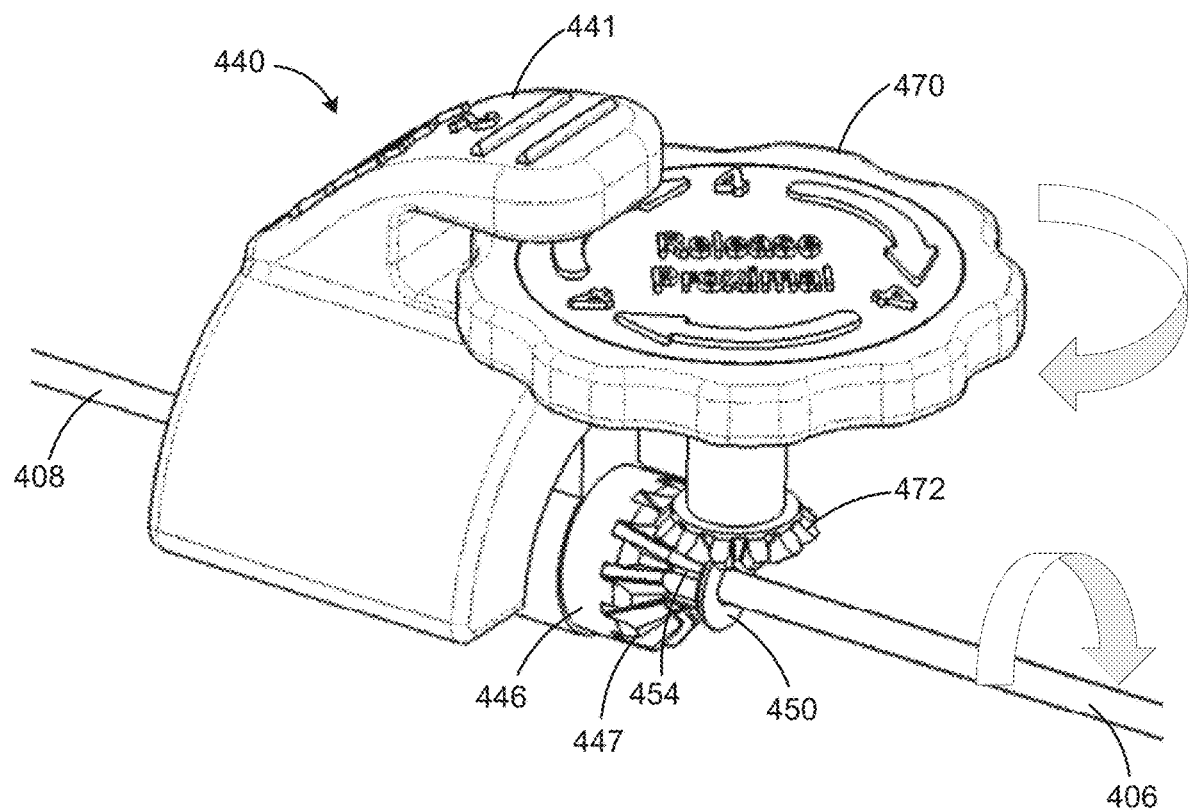

At step 328, rotatable inner shaft actuator 480 may be actuated, e.g., rotated, as shown in FIG. 21E, to thereby cause rotation of inner shaft 408, which causes threaded surface 409 at the distal region of inner shaft 408 to decouple from threaded surface 213 of distal end 205 of occluder 200. At step 330, rotatable outer shaft actuator 470 may be actuated, e.g., rotated, such that rotational movement of bevel gear 472 about the rotational axis of rotatable outer shaft actuator 470 causes rotational movement of bevel gear 446, and accordingly splined rotary shaft 450 and outer shaft 406, about the longitudinal/rotational axis of bevel gear 446 via the operative engagement between bevel gear 472 and geared surface 447 of bevel gear 446, as shown in FIG. 21F, which causes threaded surface 407 at the distal region of outer shaft 406 to decouple from threaded surface 209 of proximal end 203 of occluder 200. Accordingly, at step 332, delivery system 400 may be removed from the patient's body, leaving occluder 200 implanted at the atrial septum. As will be understood by a person having ordinary skill in the art, during deployment of occluder 200 at the atrial septum via system 400, slidable outer shaft actuator 440 may be actuated to transition occluder 200 back to its collapsed delivery state, and/or outer sheath actuator 460 may be actuated to recapture/reload occluder 200 within outer sheath 410, to thereby permit the user to reposition/realign occluder 200 for proper implantation at the atrial septum.

Figure 22A:
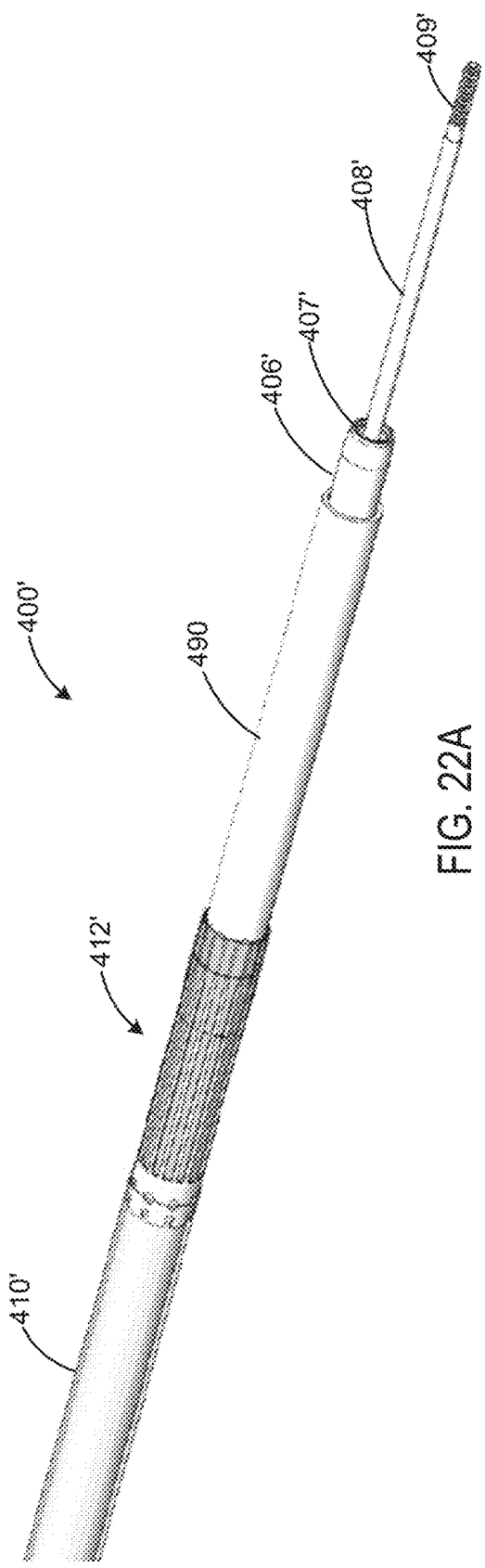
FIGS. 22A and 22B illustrate an alternative exemplary delivery system having a steerable shaft constructed in accordance with the principles of the present disclosure.
Figure 22B:
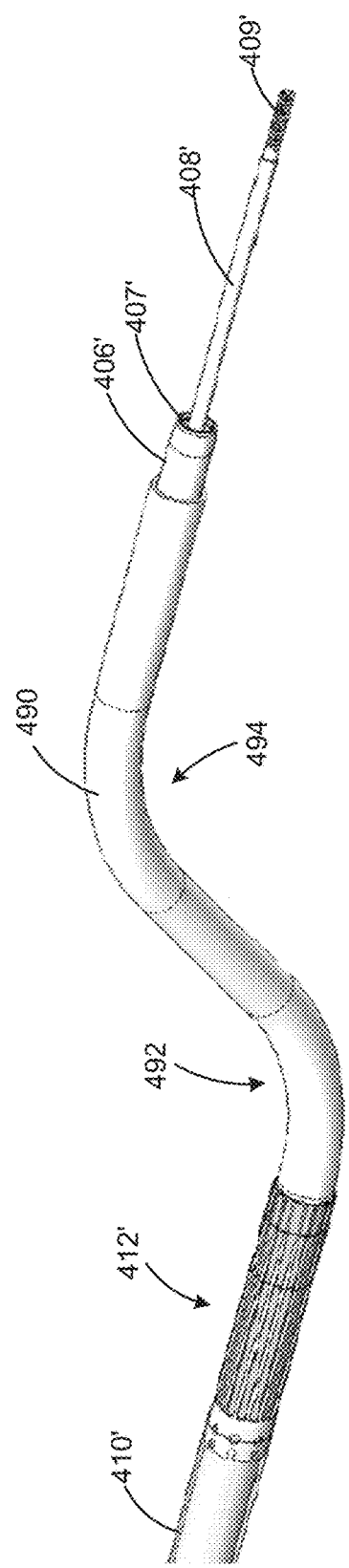

Referring now to FIGS. 22A and 22B, an alternative exemplary delivery system is provided. System 400' may be constructed similar to system 400, with similar components having like-prime reference numerals. For example, outer shaft 406' having engagement portion 407', inner shaft 408' having engagement portion 409', and outer sheath 410' having expandable distal region 412' of system 400' correspond to outer shaft 406 having engagement portion 407, inner shaft 408 having engagement portion 409, and outer sheath 410 having expandable distal region 412, respectively, of system 400. System 400' differs from system 400 in that system 400' may include steerable shaft 490. Steerable shaft 490 may be disposed over and axially fixed relative to outer shaft 406'. Accordingly, the distance between the distal ends of steerable shaft 490 and outer shaft 406' may be fixed.

As shown in FIG. 22B, steerable shaft 490 may have one or more steerable zones, e.g., steerable zone 492 and steerable zone 494, along a distal section of steerable shaft 490. Steerable zone 492 and steerable zone 494 may be configured to be actuated, e.g., via one or more actuators at the handle, by a user to controllably form a bend along steerable zone 492 and/or a bend along steerable zone 494 to thereby form an S-shape shaft to facilitate alignment of distal region 412' with the atrial septal defect during delivery of occluder 200, as shown in FIG. 22B. For example, steerable zone 492 and steerable zone 494 may be actuated via one or more pull wires operatively coupled to the one or more respective actuators at the handle. Steerable zone 492 and steerable zone 494 may be actuated together via a single set of one or more actuators at the handle, or alternatively, may be independently actuated via separate sets of one or more actuators at the handle.

Figure 23A:
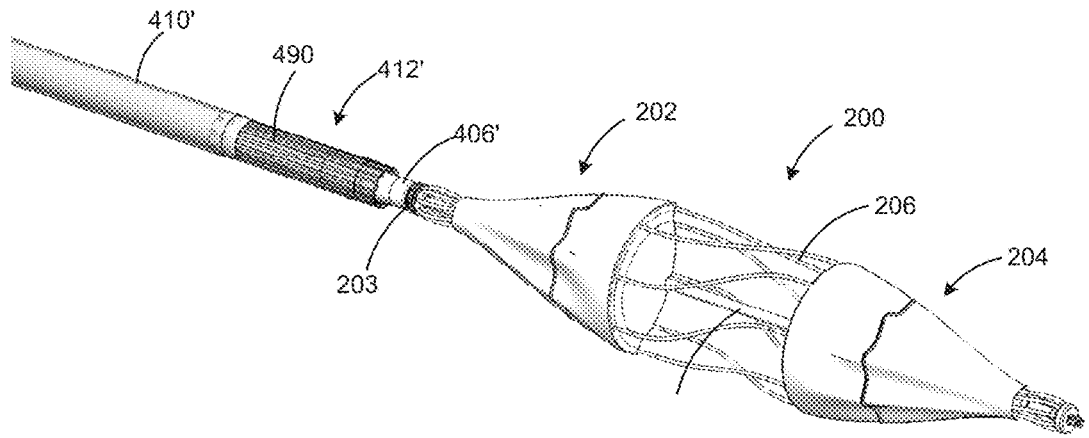
FIGS. 23A to 23C illustrate exemplary method steps for delivering an implantable occluder device using the delivery system of FIGS. 22A and 22B in accordance with the principles of the present disclosure.
Figure 23B:
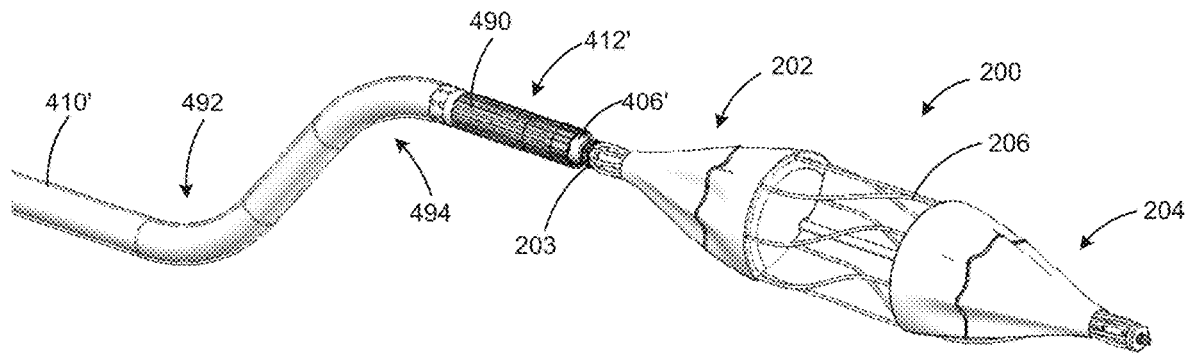
Figure 23C:
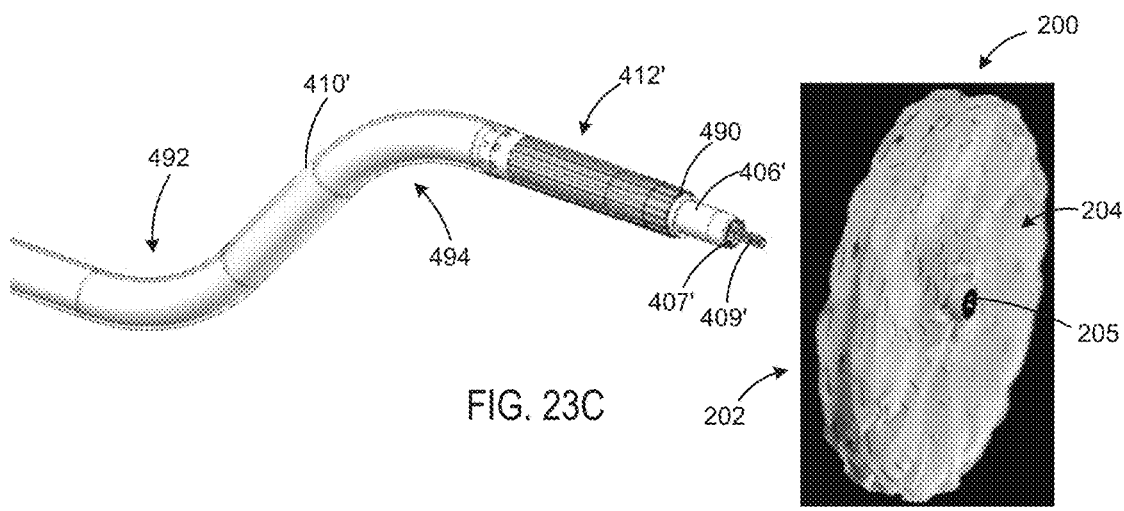

Referring now to FIGS. 23A to 23C, exemplary method steps for delivering occluder 200 using delivery system 400' is provided. Proximal end 203 and distal end 205 of occluder 200 may be coupled to outer shaft 406' and inner shaft 408', respectively, in a similar manner to outer shaft 406 and inner shaft 408 described above. Moreover, occluder 200 may be loaded into the lumen of outer sheath 410' via distal region 412' in a similar manner to outer sheath 410 described above, and may similarly be advanced over a guidewire to the atrial septum. When distal region 412' is advanced across the atrial septal defect such that occluder 200 is aligned with the atrial septum, outer sheath 410' may be retracted proximally relative to outer shaft 406' and inner shaft 408', and accordingly occluder 200, to thereby expose occlude 200 from the distal end of distal region 412' in its collapsed delivery state, as shown in FIG. 23A. Next, steerable zones 492, 494 may be actuated, e.g., via one or more actuators at the handle, to controllably form a bend along steerable zone 492 and a bend along steerable zone 494, to thereby form an S-shape along the distal section of steerable shaft 490, and accordingly along the distal sections of outer shaft 406', inner shaft 408', and outer sheath 410', as shown in FIG. 23B, to facilitate axial alignment of occluder 200 with the atrial septum. When occluder 200 is in the desired axial position relative to the atrial septum, outer shaft 406' may be actuated to decouple from proximal end 203 of occluder 200, and inner shaft 408' may be actuated to decouple from distal end 205 of occluder 200, as shown in FIG. 23C. System 400' may then be removed from the patient.

Figure 24:
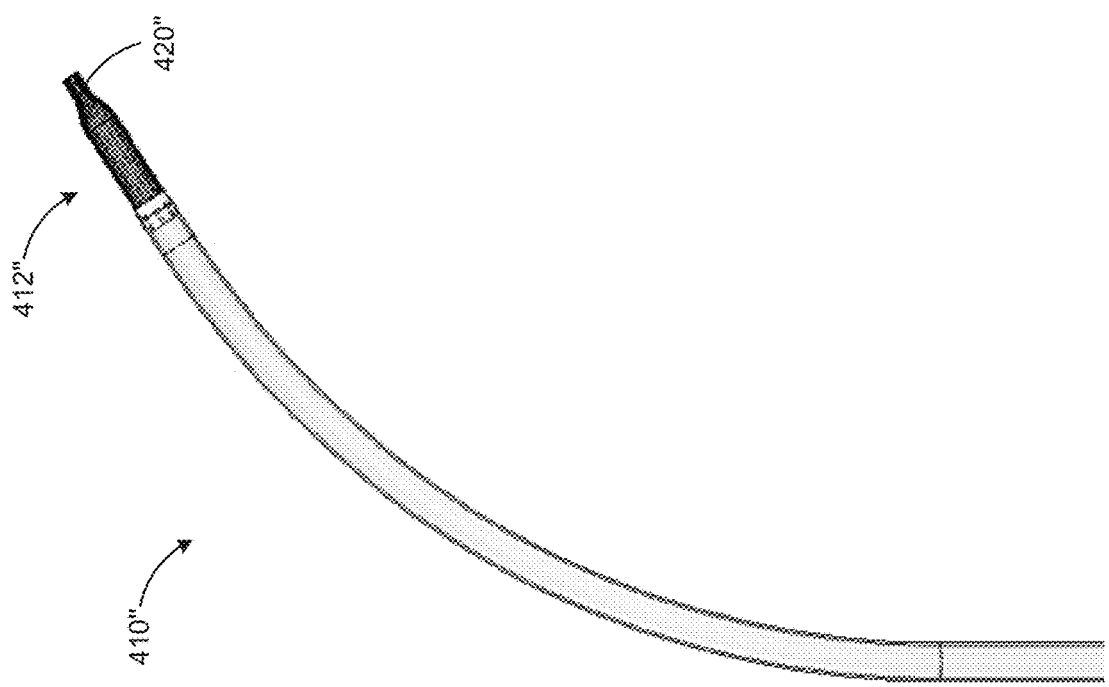
FIG. 24 illustrates an alternative exemplary outer sheath having a preformed bend constructed in accordance with the principles of the present disclosure.

Referring now to FIG. 24, an alternative exemplary outer sheath is provided. Outer sheath 410" may be constructed similar to outer sheath 410, with similar components having like-double prime reference numerals. For example, distal region 412" and tip 420" of outer sheath 410" correspond to distal region 412 and tip 420, respectively, of outer sheath 410. Outer sheath 410" differs from outer sheath 410 in that outer sheath 410" may include a permanent, preformed curve along its length, e.g., along the distal section of outer sheath 410", to facilitate alignment of distal region 412" with the atrial septal defect during delivery of occluder 200.

Figure 25:
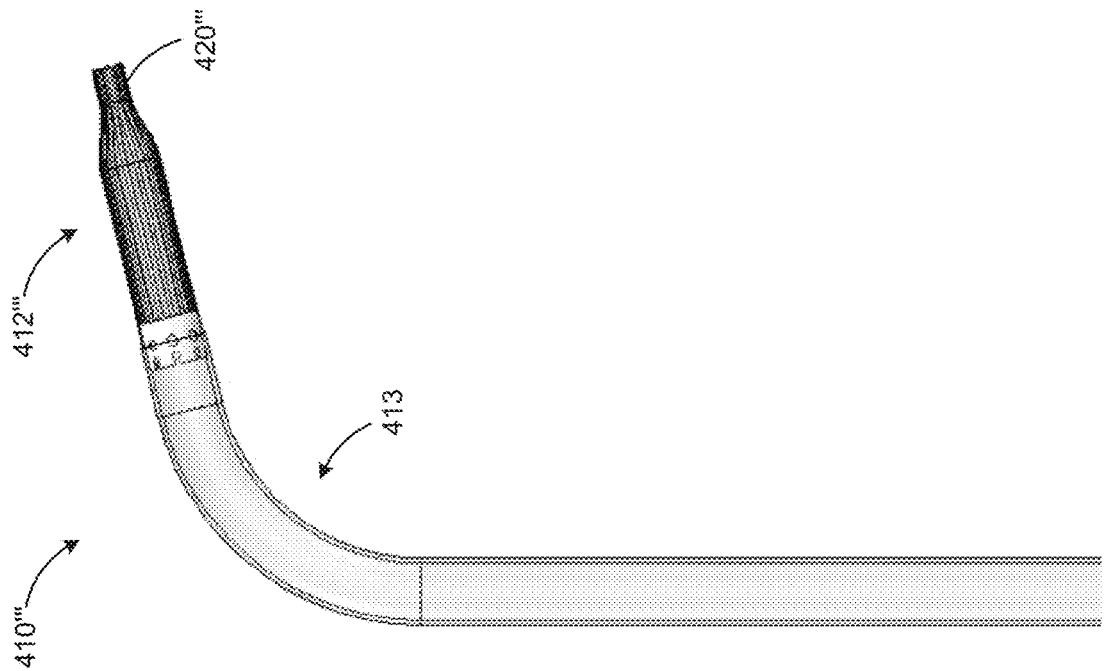
FIG. 25 illustrates another alternative exemplary outer sheath having a steerable zone constructed in accordance with the principles of the present disclosure.

Referring now to FIG. 25, another alternative exemplary outer sheath is provided. Outer sheath 410''' also may be constructed similar to outer sheath 410, with similar components having like-triple prime reference numerals. For example, distal region 412''' and tip 420''' of outer sheath 410''' correspond to distal region 412 and tip 420, respectively, of outer sheath 410. Outer sheath 410''' differs from outer sheath 410 in that outer sheath 410''' may include steerable zone 413 configured to be actuated, e.g., via one or more actuators at handle 430, by a user to controllably form a bend along steerable zone 413 to facilitate alignment of distal region 412''' with the atrial septal defect during delivery of occluder 200. For example, steerable zone 413 may be actuated via one or more pull wires operatively coupled to the one or more respective actuators at handle 430.

While various illustrative embodiments of the invention are described above, it will be apparent to one skilled in the art that various changes and modifications may be made therein without departing from the invention. The appended claims are intended to cover all such changes and modifications that fall within the true scope of the invention.

What is claimed:

1. An apparatus for delivering an occluder to an atrial septum of a patient, the occluder configured to transition between a collapsed delivery state and an expanded deployed state, the apparatus comprising:
   an inner shaft having a proximal region and a distal region comprising a first engagement portion configured to be removably coupled to a distal end of the occluder;
   an outer shaft slidably disposed over the inner shaft, the outer shaft having a proximal region and a distal region comprising a second engagement portion configured to be removably coupled to a proximal end of the occluder;

an outer sheath slidably disposed over the outer shaft, the outer sheath having a proximal region, a distal region, and a lumen sized and shaped to receive the occluder in the collapsed delivery state, the distal region of the outer sheath comprising an expandable structure and configured to transition from an elongated collapsed configuration to an expanded configuration upon application of force to the distal region of the outer sheath, the expanded configuration sized and shaped to receive the occluder therethrough; and a handle operatively coupled to the proximal regions of the inner shaft, the outer shaft, and the outer sheath, the handle comprising:
- a first slidable actuator configured to be actuated to move the outer sheath distally to apply a force to the distal region of the outer sheath such that the expandable structure transitions from the elongated collapsed configuration where the distal regions of the outer and inner shafts are exposed from the outer sheath to the expanded configuration where the distal regions of the outer and inner shafts are at least partially disposed within the lumen of the outer sheath;
- a second slidable actuator configured to be actuated to move the outer shaft relative to the inner shaft to transition the occluder between the collapsed delivery state and the expanded deployed state;
- a third rotatable actuator configured to be actuated to decouple the first engagement portion of the inner shaft from the distal end of the occluder; and
- a fourth rotatable actuator configured to be actuated to decouple the second engagement portion of the outer shaft from the proximal end of the occluder when the occluder is disposed at the atrial septum.

2. The apparatus of claim 1, wherein the inner shaft comprises a lumen sized and shaped to receive a guidewire therethrough.

3. The apparatus of claim 1, wherein an outer surface of the first engagement portion comprises a threaded surface configured to be removably coupled to a threaded surface of the distal end of the occluder, and
wherein the inner shaft is configured to be rotated to decouple the threaded surface of the first engagement portion from the threaded surface of the distal end of the occluder.

4. The apparatus of claim 1, wherein an inner surface of the second engagement portion comprises a threaded surface configured to be removably coupled to a threaded surface of the proximal end of the occluder, and
wherein the outer shaft is configured to be rotated to decouple the threaded surface of the second engagement portion from the threaded surface of the proximal end of the occluder.

5. The apparatus of claim 1, wherein relative movement between the inner and outer shafts causes the occluder to transition between the collapsed delivery state and the expanded deployed state.

6. The apparatus of claim 1, wherein the expandable structure is further configured to transition to a collapsed delivery configuration where a cross-sectional area of a distal portion of the distal region of the outer sheath decreases from a proximal end of the distal portion towards a distal end of the distal portion to thereby define an atraumatic tip, and wherein the distal portion of the distal region of the outer sheath is biased towards the collapsed delivery configuration.

7. The apparatus of claim 6, wherein, in the collapsed delivery configuration, the inversion point is aligned with a distal end of the atraumatic tip.

8. The apparatus of claim 1, further comprising:
- a fixed shaft disposed within the lumen of the outer sheath,
- wherein the expandable structure comprises a braided structure having a first end region coupled to the distal region of the outer sheath, and a second end region coupled to a distal region of the fixed shaft, such that the braided structure folds within itself at an inversion point, to thereby divide the braided structure into an outer region and an inner region, and
- wherein relative movement between the outer sheath and the fixed shaft causes the inversion point to move axially along a longitudinal axis of the apparatus.

9. The apparatus of claim 8, wherein the braided structure comprises Nitinol.

10. The apparatus of claim 8, wherein at least a portion of the braided structure adjacent the inversion point is configured to expand radially outward to an expanded state upon application of force to the at least the portion of the braided structure responsive to distal movement of the outer sheath relative to the fixed shaft.

11. The apparatus of claim 8, wherein the inversion point defines an opening configured to facilitate loading of the occluder within the lumen of the outer sheath in the collapsed delivery state as the outer sheath moves distally relative to the fixed shaft, and
wherein the inner region of the braided structure is configured to contact and envelop the occluder in the collapsed delivery state as the outer sheath moves distally relative to the fixed shaft.

12. The apparatus of claim 8, wherein the fixed shaft comprises:
- an attachment ring disposed at the distal region of the fixed shaft, the attachment ring configured to be coupled to the first end region of the braided structure; and
- a crimper ring configured to be disposed over the first end region of the braided structure at the distal region of the fixed shaft to maintain coupling between the first end region of the braided structure and the attachment ring.

13. The apparatus of claim 8, wherein the braided structure comprises a coating configured to prevent thrombus.

14. The apparatus of claim 8, wherein the handle is operatively coupled to the proximal region the fixed shaft, and wherein the first slidable actuator is configured to be actuated to move the outer sheath relative to the fixed shaft to transition the braided structure between the elongated collapsed configuration where the distal regions of the outer and inner shafts are exposed from the outer sheath, and the expanded configuration where the distal regions of the outer and inner shafts are disposed within the lumen of the outer sheath.

15. The apparatus of claim 14, wherein the first slidable actuator comprises:
- a pusher configured to be actuated to permit axial movement of the first slidable actuator relative to the handle, the pusher comprising a locking pin configured to releasably engage with a groove of a plurality of indexing grooves of the handle when the pusher is in an unactuated state to thereby lock the first slidable actuator relative to the handle; and a compression spring coupled to the pusher, the compression spring configured to bias the pusher towards the unactuated state.

16. The apparatus of claim 14, wherein the second slidable actuator comprises:
a pusher configured to be actuated to permit axial movement of the second slidable actuator relative to the handle, the pusher comprising a locking pin configured to releasably engage with a groove of a plurality of indexing grooves of the handle when the pusher is in an unactuated state to thereby lock the second slidable actuator relative to the handle; and
a compression spring coupled to the pusher, the compression spring configured to bias the pusher towards the unactuated state.

17. The apparatus of claim 14, wherein the second slidable actuator comprises:
a frame comprising a track extending circumferentially along an inner surface of the frame, the track extending in a plane perpendicular to a longitudinal axis of the outer shaft; and
a connector fixedly coupled to the proximal region of the outer shaft and rotatably disposed within the frame, the connector comprising one or more pins configured to slidably engage with the track of the frame,
wherein movement of the one or more pins along the track causes rotation of the outer shaft.

18. The apparatus of claim 17, wherein the third rotatable actuator comprises:
a sun gear configured to be rotated in response to rotation of the third rotatable actuator; and
a transmission shaft extending proximally from the sun gear and at least partially disposed within a lumen of the frame of the second slidable actuator, the transmission shaft comprising a lumen sized and shaped to slidably receive the outer shaft therethrough, and a track extending longitudinally along a length of the transmission shaft, the track sized and shaped to receive the one or more pins of the connector of the second slidable actuator therethrough,
wherein rotation of the transmission shaft causes the one or more pins to move along the track of the frame via engagement between the track of the transmission shaft and the one or more pins.

19. The apparatus of claim 18, wherein the third rotatable actuator comprises a planet gear having a geared outer surface, the planet gear disposed between an inner geared surface of the third rotatable actuator and a geared outer surface of the sun gear, such that rotation of the third rotatable actuator in a first direction about the handle causes rotation of the planet gear in the first direction via the inner geared surface and the geared outer surface of the planet gear, which causes rotation of the sun gear in a second direction opposite the first direction via the geared outer surfaces of the planet gear and the sun gear.

20. The apparatus of claim 14, wherein the third rotatable actuator comprises a connector configured to be fixedly coupled to the proximal region of the fixed shaft.

21. The apparatus of claim 14, wherein the fourth rotatable actuator comprises a locking mechanism configured to transition from a locked state where rotation of the fourth rotatable actuator is prevented, and an unlocked state where rotation of the fourth rotatable actuator is permitting.

22. The apparatus of claim 21, wherein the locking mechanism comprises a slidable latch.

23. The apparatus of claim 1, wherein the outer sheath comprises at least one of a pre-formed bend configured to facilitate alignment of the occluder with the atrial septum or a steerable zone configured to be actuated to form a bend along the outer sheath to facilitate alignment of the occluder with the atrial septum.

24. The apparatus of claim 1, further comprising a steerable shaft disposed over the outer shaft, the steerable shaft configured to be actuated to form one or more bends along a distal region of the steerable shaft to facilitate alignment of the occluder with the atrial septum.

25. A system comprising the apparatus of claim 1 and the occluder, the occluder comprising:
a plurality of bioresorbable filaments extending between the proximal and distal ends of the occluder, and defining a proximal portion, a central portion, and a distal portion of the occluder, the plurality of bioresorbable filaments arranged to transition between an elongated configuration in the collapsed delivery state and an expanded configuration in the expanded deployed state where the proximal and distal portions of the occluder expand radially outward and the central portion contracts radially inward; and
a biocompatible fabric disposed on at least the proximal and distal portions of the occluder,
wherein the proximal and distal portions of the occluder are configured to sandwich the atrial septum in the expanded deployed state, such that the central portion of the occluder is disposed within the atrial septum.

26. A method for delivering an occluder to an atrial septum of a patient, the method comprising:
advancing an outer shaft, an inner shaft, and the occluder in a collapsed delivery state to the atrial septum such that a distal portion of the occluder is disposed within a first atrium and a proximal portion of the occluder is disposed within a second atrium, a distal end of the occluder removably coupled to a distal region of the inner shaft via a first engagement portion at the distal region of the inner shaft and a proximal end of the occluder removably coupled to a distal region of the outer shaft via a second engagement portion at the distal region of the outer shaft;
actuating a first slidable actuator of a handle operatively coupled to a proximal region of the outer shaft axially relative to the handle to move the outer shaft distally relative to the inner shaft to transition the occluder from the collapsed delivery state to an expanded deployed state, such that the proximal and distal portions of the occluder sandwich the atrial septum in the expanded deployed state;
actuating the first slidable actuator to move the outer shaft proximally relative to the inner shaft to transition the occluder from the expanded deployed state towards the collapsed delivery state;
actuating a second slidable actuator of the handle operatively coupled to a proximal region of the outer sheath axially relative to the handle to move the outer sheath distally relative to the outer shaft to apply a force to an expandable structure at a distal region of the outer sheath and transition the expandable structure from an elongated collapsed configuration to an expanded configuration to receive the occluder therethrough in the collapsed delivery state; and
removing the inner and outer shafts and the outer sheath having the occluder disposed therein in the collapsed delivery state from the patient,
wherein the handle comprises a third rotatable actuator operatively coupled to the proximal region of the inner shaft, the third rotatable actuator configured to be actuated to decouple the first engagement portion of the inner shaft from the distal end of the occluder, and a fourth rotatable actuator operatively coupled to a proximal region of the outer shaft, the fourth rotatable actuator configured to be actuated to decouple the second engagement portion of the outer shaft from the proximal end of the occluder.

27. The method of claim 26, further comprising:
removably coupling the distal region of the inner shaft to the distal end of the occluder via the first engagement portion at the distal region of the inner shaft;
removably coupling the distal region of the outer shaft to the proximal end of the occluder via the second engagement portion at the distal region of the outer shaft, the outer shaft slidably disposed over the inner shaft within the outer sheath; and
actuating the first slidable actuator to move the outer shaft proximally relative to the inner shaft to transition the occluder from the expanded deployed state towards the collapsed delivery state prior to advancing the inner and outer shafts and the occluder in the collapsed delivery state to the atrial septum.

28. The method of claim 26, wherein the expandable structure comprises a braided structure having a first end region coupled to the distal region of the outer sheath, and a second end region coupled to a distal region of a fixed shaft disposed within a lumen of the outer sheath,
wherein moving the outer sheath distally relative to the outer shaft to apply the force to the expandable structure causes the braided structure to fold within itself at an inversion point, the inversion point defining an opening and dividing the braided structure into an outer region and an inner region, and
wherein moving the outer sheath distally relative to the outer shaft causes the inner region of the braided structure to contact and envelop the occluder in the collapsed delivery state as the outer sheath moves distally relative to the fixed shaft.

29. The method of claim 26, further comprising:
actuating the third rotatable actuator of the handle to rotate the inner shaft to decouple the distal region of the inner shaft from the proximal distal end of the occluder;
actuating the fourth rotatable actuator of the handle to rotate the outer shaft to decouple the distal region of the outer shaft from the proximal end of the occluder; and
removing the outer sheath and the inner and outer shafts from the patient.

30. The method of claim 29, wherein actuating the fourth rotatable actuator of the handle comprises rotating a sun gear and a transmission shaft coupled thereto, the transmission shaft extending through a frame of the first slidable actuator and comprising a longitudinally extending track, and
wherein rotation of the transmission shaft causes rotation of a connector within the frame via one or more pins of connector extending through the longitudinally extending track of the transmission shaft, the connector coupled to the proximal region of the outer shaft.

\* \* \* \* \*